(12) United States Patent
Hoffstetter

(10) Patent No.: US 11,759,402 B2
(45) Date of Patent: Sep. 19, 2023

(54) ENTERAL FEEDING SYSTEMS AND METHODS

(71) Applicant: Generica Medical International, Inc., La Verne, CA (US)

(72) Inventor: Leonard P. Hoffstetter, La Verne, CA (US)

(73) Assignee: Generica Medical International, Inc., La Verne, CA (US)

( * ) Notice: Subject to any disclaimer, the term of this patent is extended or adjusted under 35 U.S.C. 154(b) by 953 days.

(21) Appl. No.: 16/455,759

(22) Filed: Jun. 28, 2019

(65) Prior Publication Data
US 2020/0000682 A1    Jan. 2, 2020

Related U.S. Application Data

(60) Provisional application No. 62/692,052, filed on Jun. 29, 2018.

(51) Int. Cl.
*A61J 15/00*    (2006.01)

(52) U.S. Cl.
CPC ....... *A61J 15/0076* (2015.05); *A61J 15/0015* (2013.01); *A61J 15/0092* (2013.01); *A61J 15/0088* (2015.05)

(58) Field of Classification Search
CPC .............. A61J 15/0076; A61J 15/0015; A61J 15/0088; A61M 2039/085; A61M 5/14232
See application file for complete search history.

(56) References Cited

U.S. PATENT DOCUMENTS

| 5,092,847 A | 3/1992 | Pozzo |
| 5,242,389 A | 9/1993 | Schrader |
| 5,399,159 A | 3/1995 | Chin |
| 5,507,300 A | 4/1996 | Mukai |
| 5,584,671 A * | 12/1996 | Schweitzer, Jr. ..... A61M 5/142 604/151 |

(Continued)

FOREIGN PATENT DOCUMENTS

| WO | 2011025588 A1 | 3/2011 |
| WO | 2016018930 A1 | 2/2016 |
| WO | WO-2017134657 A1 * | 8/2017 ............... A61L 2/18 |

OTHER PUBLICATIONS

International Search Repon for PCT/US119/39644, dated Oct. 18, 2019.

(Continued)

*Primary Examiner* — James D Ponton
*Assistant Examiner* — Neeraja Gollamudi
(74) *Attorney, Agent, or Firm* — Novel IP

(57) ABSTRACT

The present specification is directed to systems, devices, and methods of portable enteral pump systems for feeding and/or flushing an ambulatory patient. Embodiments provide an enteral pumping device that may be loaded by a patient from a front and a top side of the pumping device and is therefore more convenient to use. Further, embodiments incorporate a single rotor pump for dual-use purposes of feeding nutrients and flushing fluids to the patient. A pinch valve is placed between the parallel sides of the two tubes to cut off fluid flow when required. At least one sensor is also placed between the rotor pump and an outlet. The sensors are used to detect occlusions and the type of disposables used, among other purposes.

20 Claims, 33 Drawing Sheets

(56) References Cited

U.S. PATENT DOCUMENTS

| | | |
|---|---|---|
| 5,807,333 A * | 9/1998 | Osborne ........... A61M 5/14232 604/151 |
| 6,045,536 A | 4/2000 | Meier |
| 6,458,106 B1 | 10/2002 | Meier |
| 7,070,587 B2 | 7/2006 | Meier |
| 7,080,672 B2 | 7/2006 | Fournie |
| 7,092,797 B2 | 8/2006 | Gaines |
| 7,282,044 B2 | 10/2007 | Hudson |
| 7,344,547 B2 | 3/2008 | Piskun |
| 7,402,320 B2 | 7/2008 | Mirizzi |
| 7,447,566 B2 | 11/2008 | Knauper |
| 7,462,170 B2 | 12/2008 | Fournie |
| 7,537,579 B2 | 5/2009 | Price |
| 7,608,059 B2 | 10/2009 | Harr |
| 7,611,502 B2 | 11/2009 | Daly |
| 7,621,869 B2 | 11/2009 | Ratnakar |
| 7,722,573 B2 | 5/2010 | Harr |
| 7,753,881 B2 | 7/2010 | Fournie |
| 7,753,883 B2 | 7/2010 | Fournie |
| 7,758,551 B2 | 7/2010 | Wiesner |
| 7,763,005 B2 | 7/2010 | Knauper |
| 7,794,423 B2 | 9/2010 | Gaines |
| 7,843,328 B2 | 11/2010 | Knauper |
| 7,846,131 B2 | 12/2010 | Hudson |
| 7,862,535 B2 | 1/2011 | Gaines |
| 7,887,553 B2 | 2/2011 | Lehman |
| 7,896,859 B2 | 3/2011 | Daly |
| 7,927,304 B2 | 4/2011 | Hudson |
| 7,955,317 B2 | 6/2011 | Fournie |
| 7,998,109 B2 | 8/2011 | Gaines |
| 8,034,028 B2 | 10/2011 | Fournie |
| 8,052,656 B2 | 11/2011 | Dorsey |
| 8,062,247 B2 | 11/2011 | Abe |
| 8,187,523 B2 | 5/2012 | Zucchi |
| 8,357,136 B2 | 1/2013 | Daly |
| 8,361,024 B2 | 1/2013 | Fournie |
| 8,449,501 B2 | 5/2013 | Sacchetti |
| 8,491,544 B2 | 7/2013 | Anderson |
| 8,561,614 B2 | 10/2013 | Martens |
| 8,585,584 B2 | 11/2013 | Ratnakar |
| 8,608,995 B2 | 12/2013 | Sansoucy |
| 8,684,979 B2 | 4/2014 | Deighan |
| 8,715,168 B2 | 5/2014 | Ratnakar |
| 8,715,705 B2 | 5/2014 | Maguire |
| 8,777,930 B2 | 7/2014 | Swisher |
| 8,795,225 B2 | 8/2014 | Lewis |
| D717,340 S | 11/2014 | Allyn |
| 8,882,725 B2 | 11/2014 | Davis |
| 8,951,232 B2 | 2/2015 | Fitzgerald |
| 9,198,835 B2 | 12/2015 | Swisher |
| 9,233,053 B2 | 1/2016 | Sacchetti |
| 9,402,789 B2 | 8/2016 | Knauper |
| 9,433,339 B2 | 9/2016 | Allyn |
| 9,517,184 B2 | 12/2016 | Branconier |
| 9,538,908 B2 | 1/2017 | Allyn |
| 9,585,813 B2 | 3/2017 | Dorsey |
| D785,162 S | 4/2017 | Swisher |
| 9,629,521 B2 | 4/2017 | Ratnakar |
| 9,642,777 B2 | 5/2017 | Lewis |
| 9,699,816 B2 | 7/2017 | Harr |
| 9,710,610 B2 | 7/2017 | Flynn |
| 9,820,916 B2 | 11/2017 | Boulanger |
| 9,852,263 B2 | 12/2017 | Harr |
| 9,993,392 B2 | 6/2018 | Sacchetti |
| 10,406,076 B2 | 9/2019 | Sacchetti |
| 10,426,709 B2 | 10/2019 | Harr |
| 11,510,556 B2 | 11/2022 | Ratnakar |
| 11,606,497 B2 | 3/2023 | Ratnakar |
| 11,653,816 B2 | 5/2023 | Ratnakar |
| 2003/0212381 A1 | 11/2003 | Mark |
| 2007/0208307 A1 | 9/2007 | Knauper |
| 2008/0275298 A1 | 11/2008 | Ratnakar |
| 2009/0023998 A1 | 1/2009 | Ratnakar |
| 2010/0082011 A1 * | 4/2010 | Lewis ................. A61J 15/0026 604/67 |
| 2011/0021979 A1 * | 1/2011 | Hudson ............. A61M 5/14232 604/67 |
| 2011/0160530 A1 | 6/2011 | Ratnakar |
| 2014/0107418 A1 | 4/2014 | Ratnakar |
| 2015/0065988 A1 | 3/2015 | Holderle |
| 2015/0164308 A1 | 6/2015 | Ratnakar |
| 2015/0342835 A1 * | 12/2015 | Gaines ............... F16K 37/0075 702/183 |
| 2016/0006943 A1 | 1/2016 | Ratnakar |
| 2016/0045399 A1 | 2/2016 | Wiesner |
| 2017/0120039 A1 | 5/2017 | Childs |
| 2018/0147123 A1 | 5/2018 | Sacchetti |

OTHER PUBLICATIONS

Kangaroo TM Operating Manual, Epump Enteral Feed and Flush Pump with Pole Clamp, Programmable, Covidien, 2012.

* cited by examiner

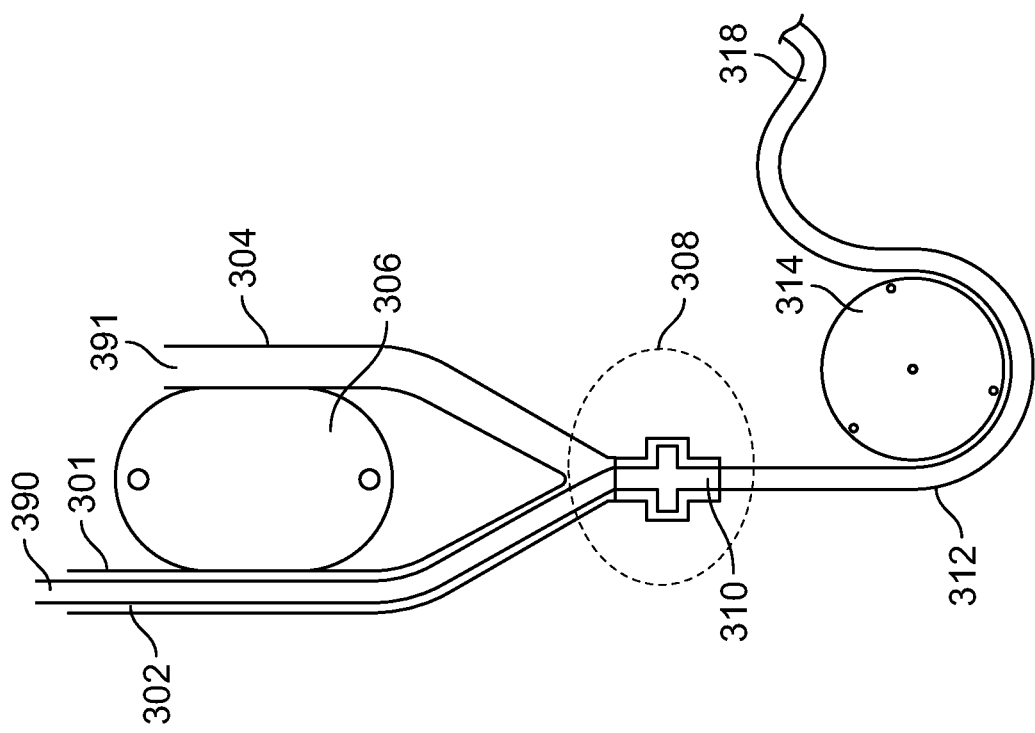

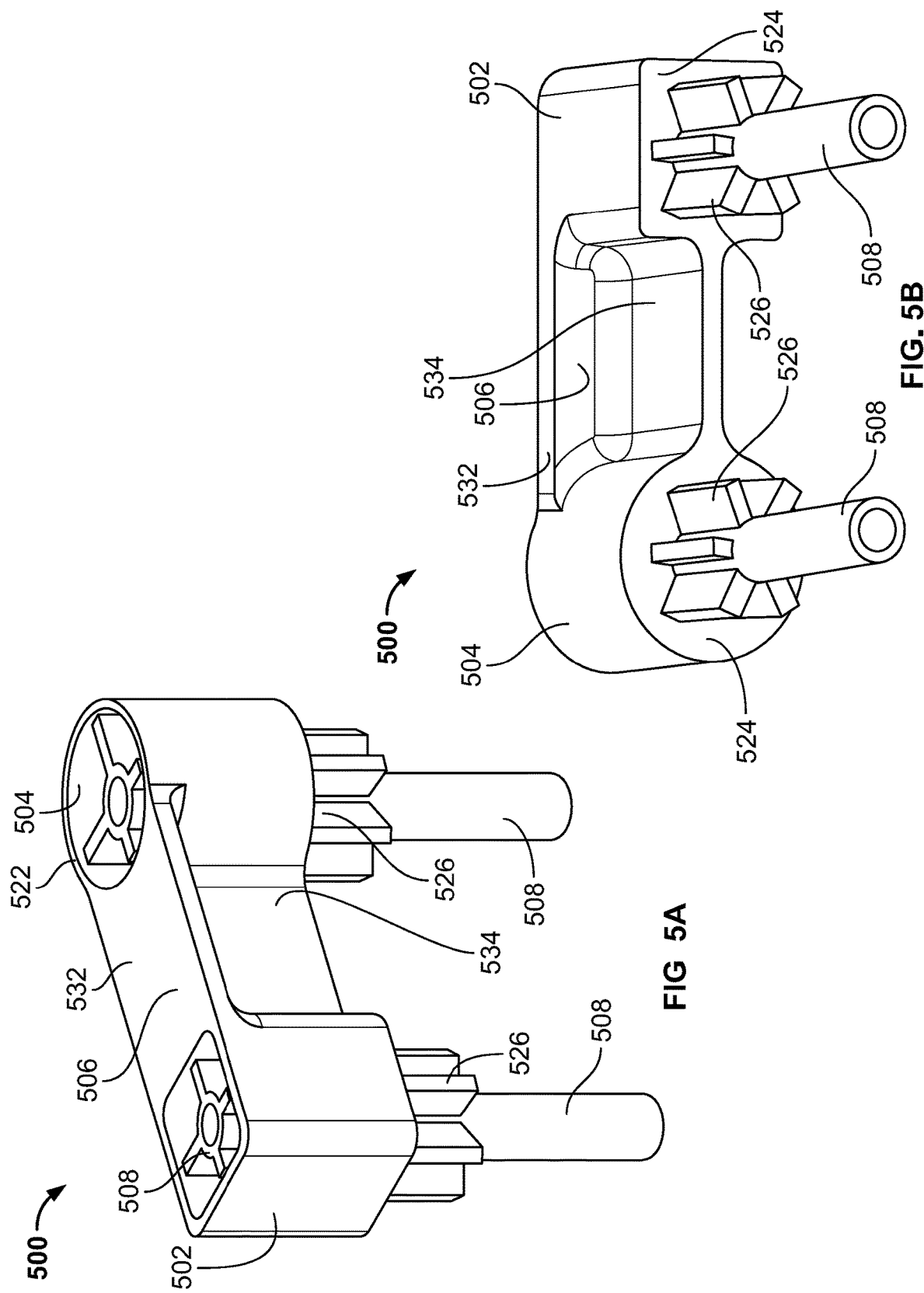

Concept Features

1. Tube wrap / hand grip
2. Pole clamp
   - Adjustable
   - Serves as cord retainer
3. Removable base
   - Battery cover
   - Cord retainer
   - Transformer retainer
4. Cord wrap
   - With retainer ridges
   - Two protrusions from back with transformer pocket between
5. Carry handle
6. Transformer storage pocket
7. Angled base

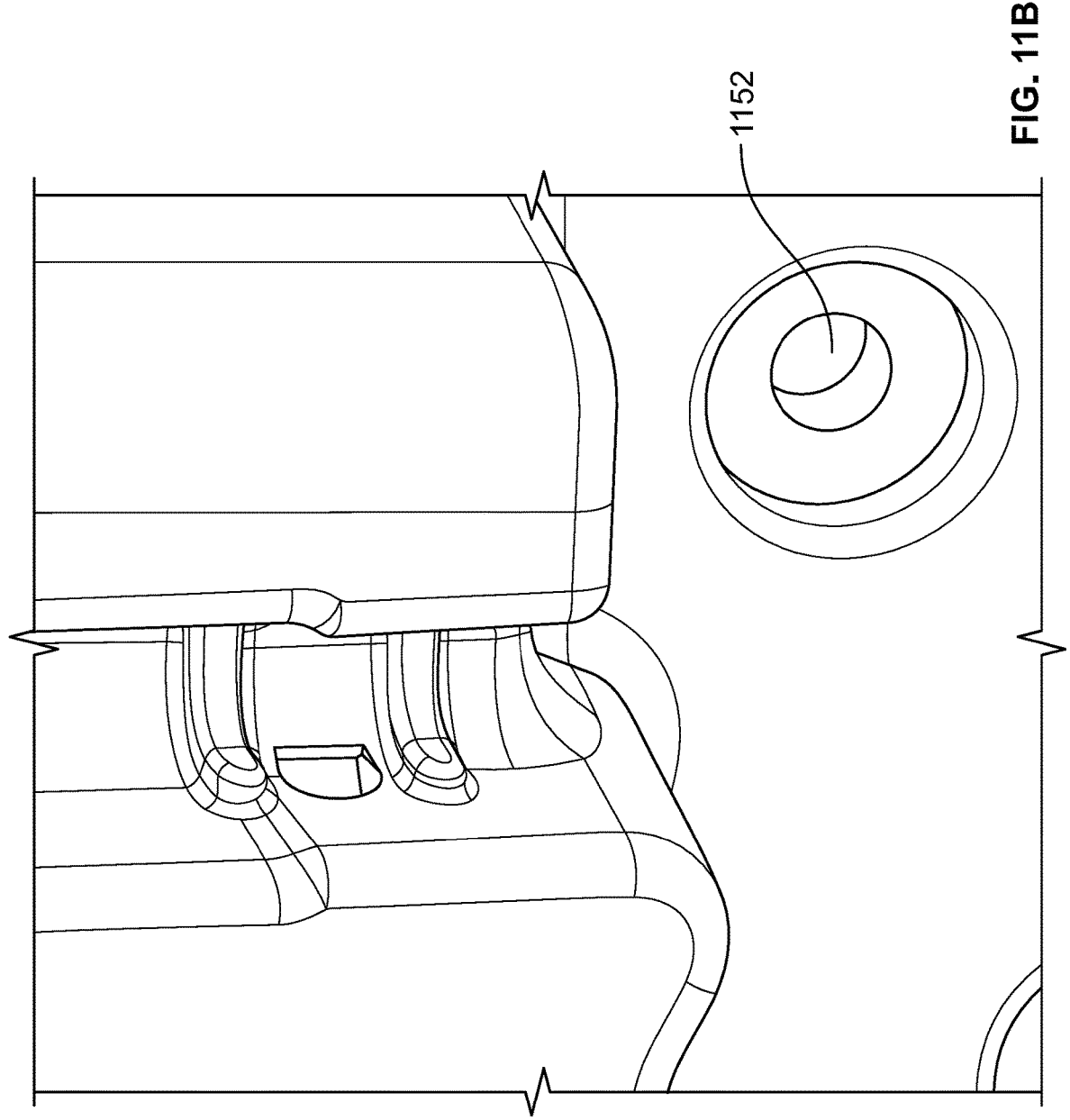

ENTERAL FEEDING SYSTEMS AND METHODS

CROSS-REFERENCE

The present specification relies on U.S. Patent Provisional Application No. 62/692,052, entitled "Enteral Feeding Systems and Methods", and filed on Jun. 29, 2018, for priority which is herein incorporated by reference in its entirety.

FIELD

The present specification relates to enteral feeding and flushing devices, and specifically relates to easy to use connectors that can be used for enteral feeding and/or for feeding and flushing.

BACKGROUND

Enteral feeding devices have been used for many years to enhance nutritional intake for pediatric as well as adult populations. Enteral feeding devices are increasingly being used in hospital and home environments. There is a growing need to provide for the controlled delivery of food or fluids to a patient in a mobile/ambulatory environment. The accuracy, safety, and consistency with which enteral feed pump systems dispense nutritional formula are important determinants of their use and acceptability.

Rotary and peristaltic pump delivery mechanisms are most commonly used in enteral devices. Pump mechanisms are incorporated in portable, mostly compact, ambulatory enteral devices. Different systems provide varying levels of accuracy and reliability while providing patients with mobility. Most ambulatory devices currently offer a feeding mechanism, but may also offer a flushing mechanism in addition to a feeding mechanism. The flushing mechanism is used for withdrawing substances from a patient's stomach. The feeding and flushing channels are tubes that comprise a flexible plastic material which comes in various diameters depending upon the size of the patient and the nature of the substance to be passed through the tube. During the course of feeding and flushing, the patient may temporarily detach one or more components of the enteral devices. Some of the components are disposable and may be replaced over a period of time. The disposable components pose a risk of contamination and infection, and need to be handled with caution.

Dual use portable enteral devices, which provide for feeding as well as flushing, are more complicated in their design relative to single-use (feeding only) devices. FIG. 1 illustrates an exemplary prior art dual-use enteral system 100. System 100 uses two separate pumps 102 and 104, one each for feeding and flushing. However, system 100 is a heavy, bulky, expensive, and difficult to use system. The two rotor pumps 102 and 104 and the disposable set within system 100, requires two silicone/PVC tubing sets 106 and 108 that are connected downstream.

FIG. 2 illustrates another exemplary prior art dual-use enteral system 200, which uses a single pump 202 for feeding as well as flushing. An outlet tube 204 is on the top and two inlets 206 and 208 are seen on the bottom. However, existing dual-use devices with a single pump are difficult to use for several reasons. First, the disposable tubing sets are difficult to mount and typically located on the side of the device which, in a clinical setting, may be challenging to reach since users are required to open a side of the box of system 200 to get access to its disposable components. Second, the configuration of the disposable tubing sets are unwieldly and, for some users, a challenge to mount.

Portable enteral devices need to be light-weight, compact, accurate, reliable, and easy-to-use. Devices are also needed that provide single or dual-use enteral mechanisms that use a single pump, enable easy access to its disposable components, are cost-effective, and are accurate. Finally, it would be desirable to have disposable tubing sets that are simple to handle and mount.

SUMMARY

The following embodiments and aspects thereof are described and illustrated in conjunction with systems, tools and methods, which are meant to be exemplary and illustrative, not limiting in scope.

The present specification discloses an enteral feeding system, comprising: a tubing set comprising two parallel tube segments attached to a Y-connector, an outlet tube segment attached to a base of the Y-connector, a first rigid component attached to the inlets of the two parallel tube segments, and a second rigid component attached to an outlet of the outlet tube segment; and an enteral feeding device comprising: a housing having a front surface; two vertical parallel channels on the front surface, wherein each of the two vertical parallel channels are configured to receive one of the two parallel tube segments; a pinch valve extending outwards from the front surface and positioned between the two parallel channels, wherein the pinch valve rotates to overlap at least partially with at least one of the two parallel channels; a rotary pump extending outwards from the front surface, wherein the rotary pump is configured to receive the outlet tube segment; a display positioned on the front surface, wherein the display is configured to present a user interface; and a first component receiver positioned at the top of the housing and configured to receive the first rigid component; and a second component receiver configured to receive the second rigid component.

Optionally, the housing further comprises a handle. The handle may be configured on a side surface or top surface of the housing.

Optionally, the tubing set further comprises a third rigid component in physical communication with the Y connector. The enteral feeding device may further comprise a third component receiver configured to receive the third rigid component. Optionally, each of the first component receiver, the second component receiver, and the third component receiver are configured to detachably receive, in a friction fit, the first rigid component, second rigid component, and third rigid component.

Optionally, the enteral feeding system comprises a first sensor positioned within one of the two parallel channels and a second sensor positioned within one of the two parallel channels. The first sensor and the second sensor may be optical sensors.

The present specification also discloses a disposable, molded tubing set configured for use in an enteral feeding system, comprising: a first tube segment having a first inlet and a first outlet and a second tube segment having a second inlet and a second outlet, wherein the first tube segment and second tube segment are configured to be parallel to each other and wherein the first inlet and the second inlet are connected to a first attachment component; a Y connector having a first Y connector inlet, a second Y connector inlet and a Y connector outlet, wherein the first outlet is connected to the first Y connector inlet and the second outlet is connected to the second Y connector inlet; and a third tube segment having a third inlet and a third outlet; wherein the third inlet is connected to the Y connector outlet and wherein the third outlet is connected to a second attachment component.

Optionally, the first tube segment and second tube segment comprise material having a first durometer value. The third tube segment may comprise material having a second durometer value, wherein the first durometer value is less than the second durometer value. Optionally, the disposable, molded tubing set further comprises a third attachment component in physical communication with the Y-connector, wherein the first attachment component, the second attachment component, and the third attachment component comprise material having a durometer value that is greater than the first durometer value or second durometer value.

Optionally, the first attachment component comprises two channels connected to each other by a bridge member.

The present specification also discloses a method of mounting a disposable feeding tube component on to an enteral device, wherein the disposable feeding component comprises at least one feeding tube with an inlet and a first attachment member and comprises an outlet tube with an outlet and a second attachment member, wherein the at least one feeding tube is connected to the outlet tube through a Y-shaped connector, and wherein the enteral device comprises at least one channel configured to receive the at least one feeding tube, a pinch valve to control the flow through the at least one feeding tube, a rotary pump, and an outlet channel configured to receive the outlet tube, the method comprising: securely connecting the at least one feeding tube to the enteral device using the first attachment member; routing the at least one feeding tube through the at least one channel to a side of the pinch valve of the enteral device; routing the outlet tube around the rotary pump; and securely connecting the outlet tube to the enteral device using the second attachment member.

Optionally, the method further comprises, using sensors positioned in the enteral device, determining whether the disposable feeding tube component is properly mounted on the enteral device. Determining whether the disposable feeding tube component is properly mounted on the enteral device may comprise determining a level of tension in the disposable feeding tube component. Determining whether the disposable feeding tube component is properly mounted on the enteral device may comprise determining if the disposable feeding tube component is authorized.

Optionally, the method further comprises, using sensors positioned in the enteral device, determining whether the disposable feeding tube component comprises occlusions.

Optionally, the method further comprises securely connecting the Y-shaped connector to the enteral device using a third attachment member.

Optionally, securely connecting the first attachment member or second attachment member comprises using friction-fit attachment receivers positioned on the enteral device.

Optionally, the method further comprises, using sensors positioned in the enteral device, identifying a type of the disposable feeding tube component.

Optionally, the method further comprises, using sensors positioned in the enteral device, identifying one of a single use disposable feeding tube component for feeding purposes or a dual use disposable feeding tube component for feeding and flushing purposes.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 3A illustrates a mounting configuration of a dual-use feeding and flushing tubing set in accordance with some embodiments of the present specification;

FIG. 3B illustrates a view of the valve shown in FIG. 3A, in accordance with some embodiments of the present specification;

FIG. 5A illustrates a front perspective view of an attachment portion used for attaching the disposable component to an enteral device in accordance with some embodiments of the present specification;

FIG. 5B illustrates a bottom perspective view of the attachment portion of FIG. 5A used for attaching the disposable component to an enteral device in accordance with some embodiments of the present specification;

FIG. 11B illustrates a close view of a slot for positioning an optical sensor, in accordance with some embodiments of the present specification;

DETAILED DESCRIPTION

Figure 1:
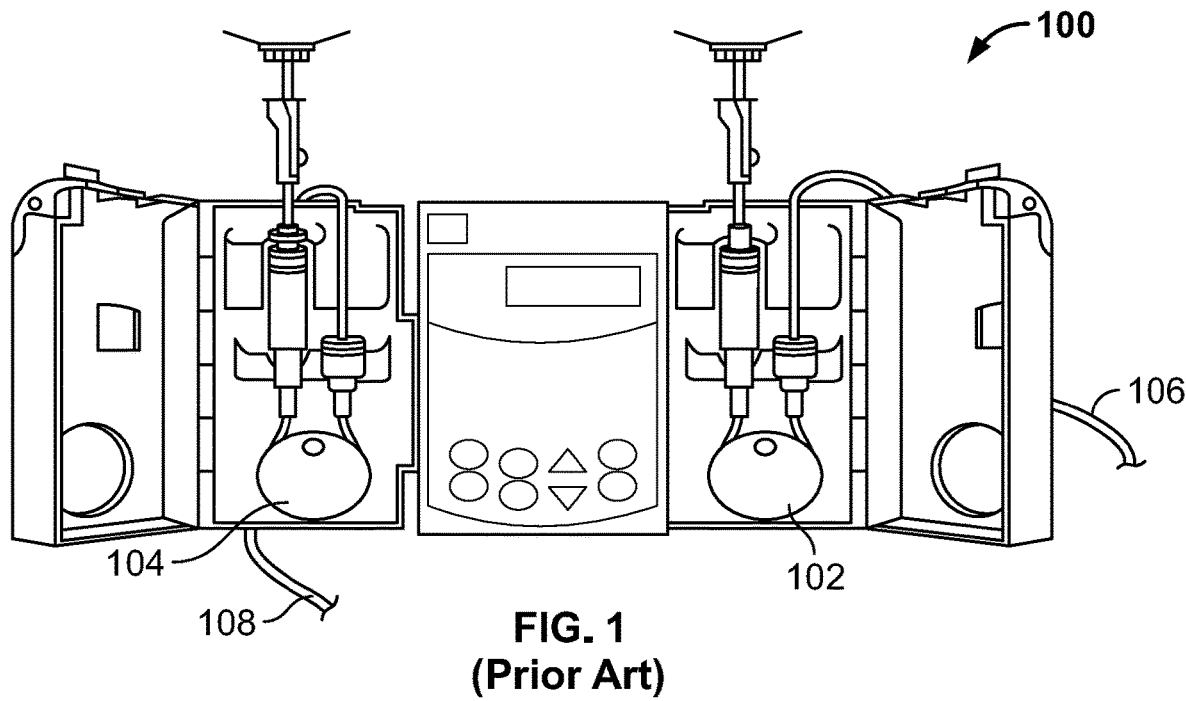
FIG. 1 is an exemplary enteral device of a prior art system.
Figure 2:
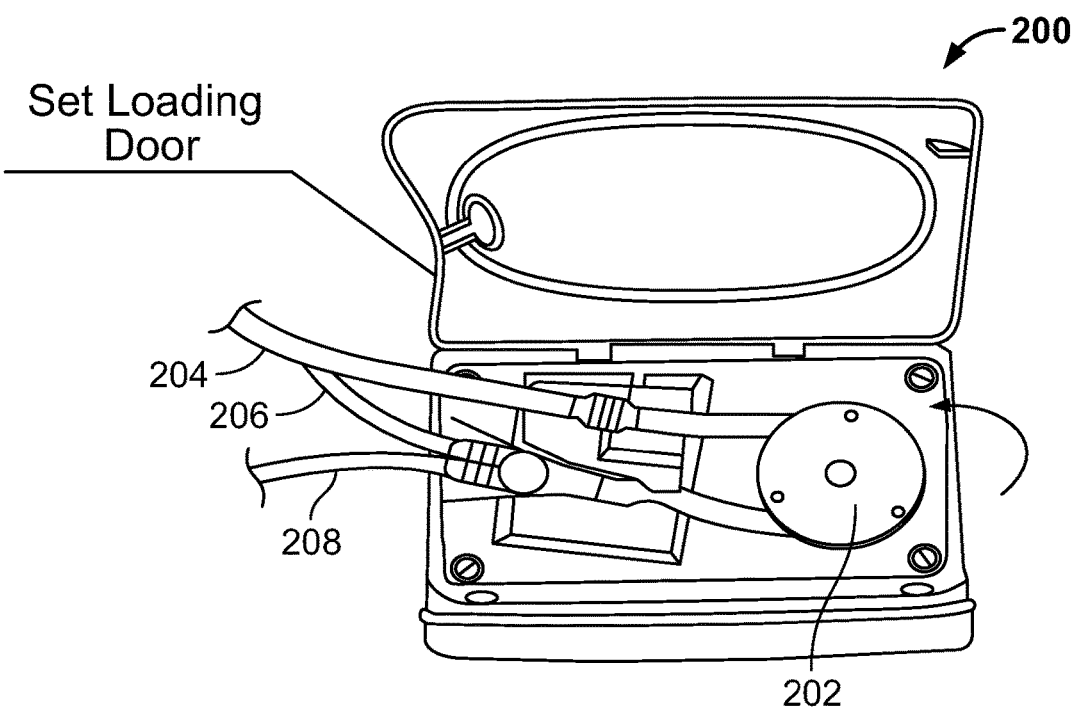
FIG. 2 is another exemplary enteral device of a prior art system.

The present specification relates to methods and systems for using portable enteral devices for feeding and/or flushing an ambulatory patient. Embodiments of the present specification provide an enteral pumping device that may be loaded by a patient from a front and a top side of the pumping device, and is therefore convenient to use. Further, embodiments of the present specification incorporate a single rotor pump for dual-use purposes of feeding nutrients to the patient, and flushing substances from the patient's stomach. A set of disposable component of the device include two prongs/tubes. A pinch valve is placed between the parallel sides of the two tubes to cut off fluid flow when required. Optionally, although preferably, the pinch valve extends outward from the front surface face of the enteral feeding pump system and is not encased or otherwise covered by a housing. In embodiments, the tubes are always pinched, unless specifically indicated otherwise by the user, to avoid free flow. The two parallel tubes merge at their ends on one side into a Y-shaped connector that connects them through a rotor pump, and through an outlet channel to an outlet. Sensors are placed below the pinch valve but above the Y-shaped connector along each prong of the disposable set. At least one sensor is also placed between the rotor pump and the outlet. The sensors are used to detect occlusions and the type of disposables used, among other purposes. At least three connectors are provided to attach the disposable component to the enteral device in a convenient manner.

Embodiments of the present specification provide a portable enteral pump system that is ergonomic and easy to use by a patient as well as by a medical personnel. In some embodiments, a side or front of the system has a little protrusion, similar to a hook, on which a nurse may hang a bag to store a syringe. Additionally, in some embodiments, a back side of the device may include a storage space for its cord and transformer, ergonomic handles, and is designed to provide ease of handling and storage.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

Disposable Component

FIG. 3A illustrates a mounting configuration of a disposable component for dual-use feeding and flushing configuration for use in an enteral pump system in accordance with some embodiments of the present specification. The enteral pump system may also be referred to as the enteral device, for purposes of the present specification. A disposable tubing set 301 is configured for mounting onto a complimentary enteral pump system relative to an enteral pump system's pinch valve 306 and a pump 314. The disposable tubing set 301 comprises two parallel tube segments, or prongs, 302 and 304, that are configured to receive fluids through their respective inlets, 390 and 391, for feeding and flushing. Prongs 302 and 304 merge into a Y-shaped connector 308 at ends opposite to their inlets. Prongs 302 and 304, each merge into one of the two arms at the top of the Y-shaped connector 308. An outlet pipe 312 extends out from the third, bottom arm of the Y-shaped connector 308 towards an outlet 318. Preferably the prongs 302, 304, Y-shaped connector 308, and outlet tubing or pipe 312 constitute a single molded, monolithic component.

Y-shaped connector 308 may include external protrusions 310 at its center or positioned towards a bottom central portion of the connector 308. FIG. 3B illustrates an exploded view of external protrusions 310 configured on, or within, a surface of the Y-shaped connector 308. In one embodiment, a pair of protrusions 310, extending outwards from the Y-shaped body of connector 308 are configured similar to wings. The wings may be used for a snap/friction-fit attachment with the body of the enteral pump system. Connector 308 may be pressed against a specified location on the enteral pump system to attach it with the system. Attaching the disposable tube set 301 using the Y-shaped connector 308 with the aid of protrusions 310, provides greater structural integrity to the tube set 301. It is critical that the tubing set 301 is under the right amount of tension so that it does not slip or move while it is attached to the enteral pump system, but is also not under so much tension that it becomes difficult for the valve 306 to occlude it or for the pump 314 to act on the fluid in the tubing 301.

FIG. 3A illustrates embodiment of the disposable component 301 that is for dual-use purposes of feeding and flushing, and therefore includes two prongs 302 and 304. In an alternative embodiment, the disposable component 301 is configured for single-use of just feeding, wherein it includes a single prong—either 302 or 304—for the purpose. The single prong is connected to one of the two arms at the top of the Y-shaped connector 308, for the purpose of feeding. Preferably the prong 302 or 304, Y-shaped connector 308, and outlet tubing or pipe 312 constitute a single molded, monolithic component with the absent prong being replaced by a closed or capped portion of the Y-shaped connector 308.

In embodiments, the tubing for the two prongs 302, 304 and for the outlet pipe 312 are designed to be optimally compliant. If not compliant enough, pinch valve 306 placed on the enteral pump system, between the parallel portions of prongs 302 and 304, in order to cut-off fluids flowing through them by moving from side to side, will not be able to pinch the tubing closed. On the other hand, if the tubing is too compliant, the tubing may slip relative to the pump 314 and, therefore, fluid or food delivery becomes inaccurate. In some embodiments, the prongs 302 and 304 between the top portion of the disposable component and the Y-connector 308, have a greater degree of compliance compared to silicone but a lower degree of compliance compared to PVC tubing.

The outlet pipe 312 portion below the Y-connector 308 may be as compliant as silicone, and may be made using silicone in an embodiment. Accordingly, in embodiments, the disposable component comprising two prongs 302, 304 attached to a Y connector, and the outlet pipe 312 have two different degrees of compliance or durometer ranges, with the compliance of the prongs 302, 304 being greater than the compliance of the outlet pipe/tube 312 or, stated differently, with the durometer of the prongs 302, 304 being less than the durometer of the outlet pipe/tube 312.

In other embodiments, the disposable component comprising two prongs 302, 304 attached to a Y connector, and the outlet pipe 312 may have the same or equal or substantially equal degrees of compliance or durometer ranges, with the compliance of the prongs 302, 304 being the same or equal or substantially equal to the compliance of the outlet pipe/tube 312.

In embodiments, the tubing may be made of polyorganosiloxane and amorphous silica having a specific gravity in a range of 1.05 g/cm$^3$ to 1.3 g/cm$^3$, and more particularly in a range of 1.11 g/cm$^3$ to 1.18 g/cm$^3$.

In some embodiments, the disposable component comprising two prongs 302, 304 attached to a Y connector, and the outlet pipe 312 comprise plastic portions, each having different degrees of compliance. Therefore, in some embodiments, the two prongs 302, 304 attached to a Y connector have one Shore A durometer value, while the outlet pipe 312 has a different Shore A durometer value. In some embodiments, each of the two prongs 302, 304 attached to a Y connector and the outlet pipe 312, has a different Shore A durometer value. In all embodiments, preferably the durometer values of the two prongs 302, 304 are lower than the durometer value of the outlet pipe 312.

FIG. 4 illustrates an isometric view of a disposable component 400 based on the mounting configuration illustrated in FIG. 3A, in accordance with some exemplary embodiments of the present specification. Disposable component 400 can be removably positioned within an enteral pump system. Disposable component 400 includes two elongated tubing segments, or prongs, 402 and 404 that are configured to receive fluid for feeding and flushing purposes. The two prongs 402 and 404 merge together by connecting with two arms at the top of a Y-shaped connector 408. An outlet pipe 412 extends out from the third arm at the bottom of the Y-shaped connector 408 towards an outlet 418.

Disposable component 400 has at least three positions/points of rigid snap attachment for attaching with the enteral pump system—one at a top 416 that also connects the two inlets of prongs 402 and 404 with a bridge-like structure, another at the Y-shaped connector 408 between a pinch valve and a pump (not shown), and a third at outlet 418. The points of rigid attachment enable a user to securely attach disposable component 400 to the enteral device. The rigid attachment points ensure the right amount of tension/slack on the tubing of the prongs 402, 404 and the outlet pipe 412, so that the pump, when it operates, will cause a predictable amount of fluid/food to flow. In an exemplary embodiment, an enteral device programmed with a feed rate of 100 ml per hour may reach that feed rate within at least +/−10 ml error rate, a 90% accuracy rate, or 10% error rate, and preferably a feed rate with at least a +/−5 ml error rate, a 95% accuracy rate, or a 5% error rate. Positioning of the rigid attachment points enables greater accuracy and a lower error in delivery of feeding and flushing fluids. In the absence of the right tension on the tubing set, the pump rotor may slip and the amount of flow through the tubes of the disposable components may become highly variable. In embodiments, each of the points of rigid snap attachment for attaching with the enteral pump system—one at top 416 that connects the two inlets of prongs 402 and 404 with a bridge-like structure, the Y-shaped connector 408 between the pinch valve and the pump, and the third connector at outlet 418, are manufactured using materials that are the hardest, and have the highest durometer values than the prongs 402, 404, or the outlet pipe 412.

In one embodiment, a pair of protrusions (not shown), extending outwards from the Y-shaped body of connector 408 are configured similar to wings. The wings may be used for a snap/friction-fit attachment with the body of the enteral pump system. Connector 408 may be pressed against a specified location on the enteral pump system to attach it with the system. Attaching the disposable tube set of the disposable component 400, using the Y-shaped connector 408 with the aid of protrusions, provides greater structural integrity to the tube set. It is critical that the tubing set is under the right amount of tension so that it does not slip or move while it is attached to the enteral pump system, but is also not under so much tension that it becomes difficult for the pinch valve to occlude it or for the pump to act on the fluid in the tubing.

The third area of attachment may be along with outlet 418, which could be snap-fit with a complimentary structure configured on the surface of the enteral device. Outlet pipe 412 may comprise a PVC tube that is guided along the surface of the rotor pump to insure there is no bending of pipe 412.

Figure 4A:
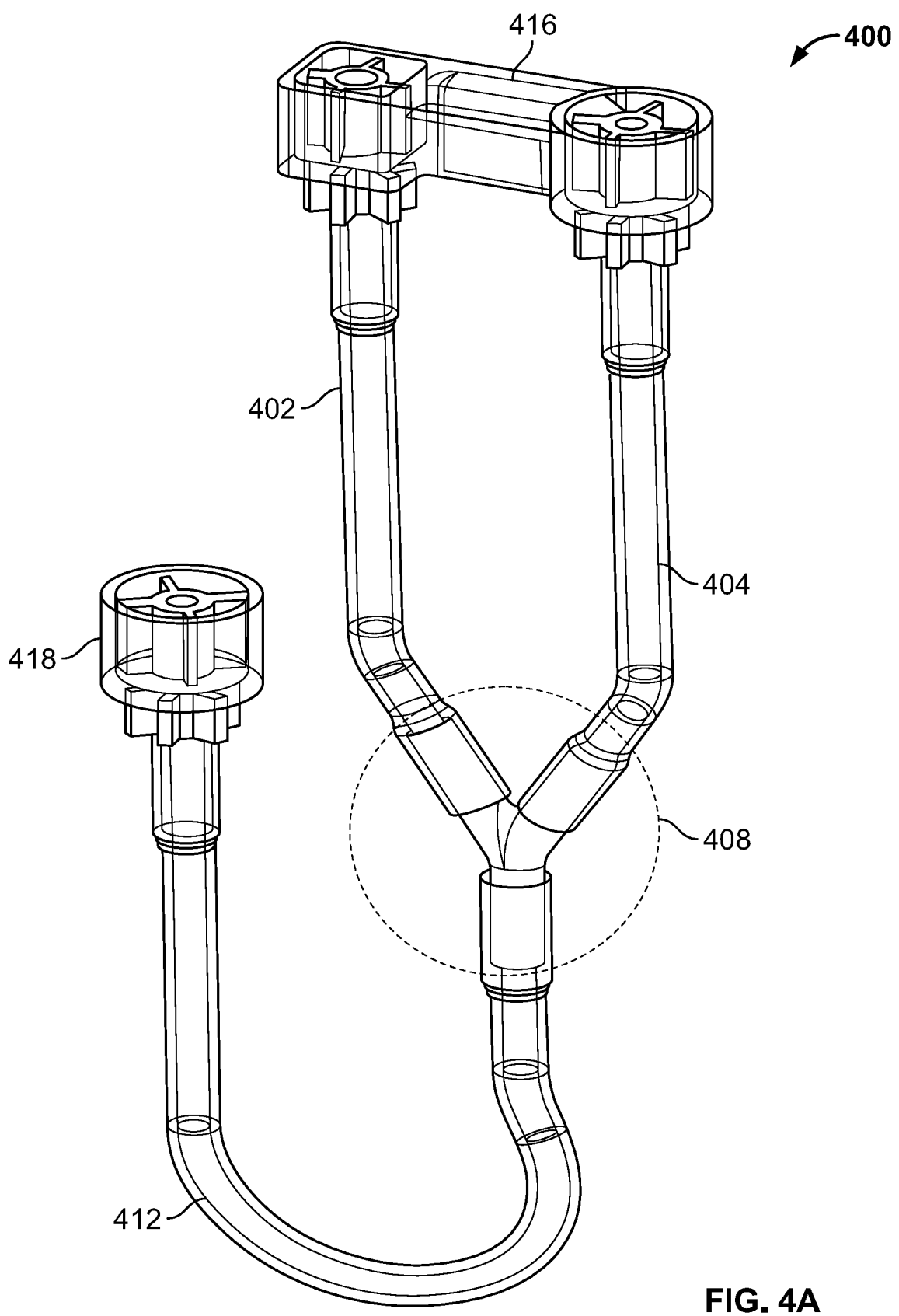
FIG. 4A illustrates an isometric view of a disposable component based on the mounting configuration illustrated in FIG. 3A, in accordance with some exemplary embodiments of the present specification.

FIG. 4A illustrates an embodiment of disposable component 400 that is for dual-use purposes of feeding and flushing, and therefore includes two prongs 402 and 404. In an alternative embodiment, disposable component 400 is configured for single-use of just feeding, wherein it includes a single prong—either 402 or 404—for the purpose.

Figure 4C:
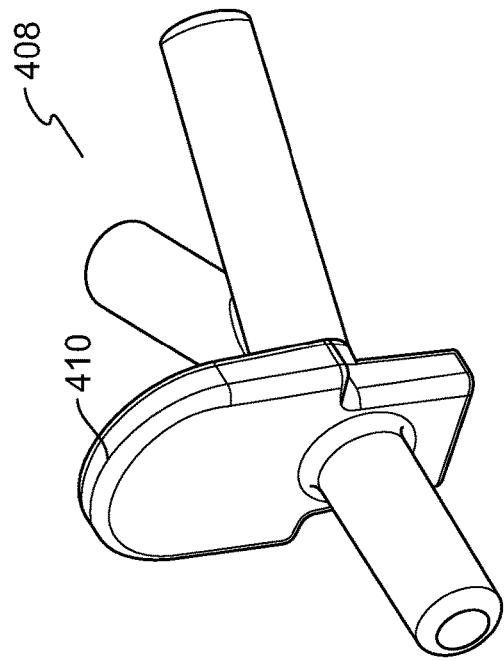
FIG. 4C illustrates a perspective drawing of the Y-shaped connector of FIG. 4B, in accordance with an embodiment of the present specification.
Figure 4D:
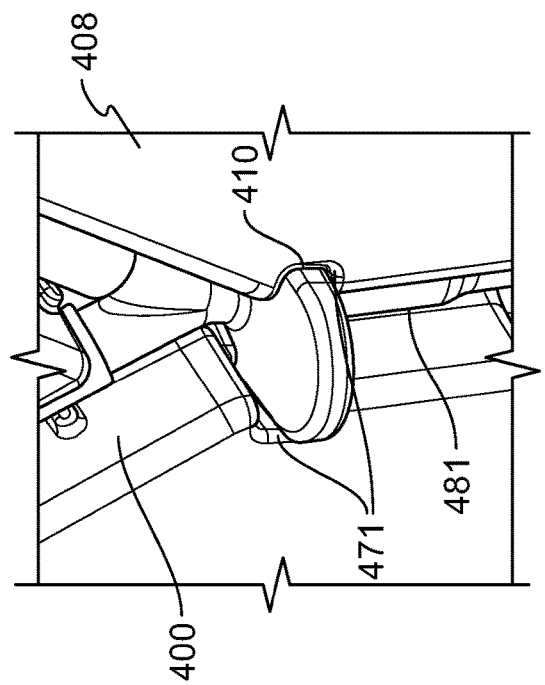
FIG. 4D illustrates another view of the Y-shaped connector of FIG. 4B that is attached to the disposable component 400 and positioned in the device, in accordance with an embodiments of the present specification.
Figure 4B:
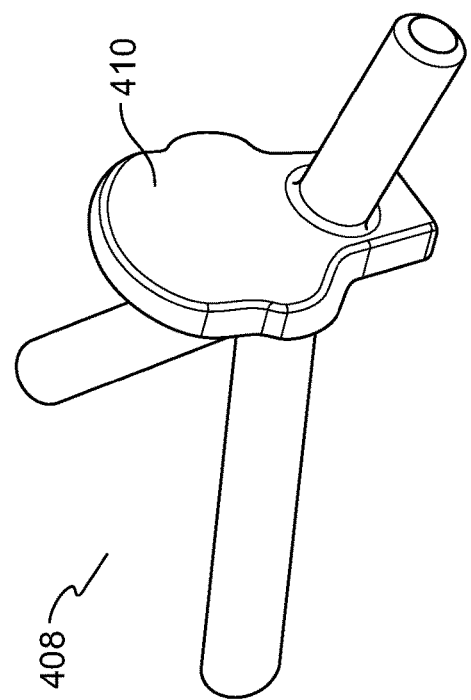
FIG. 4B illustrates a perspective view of an exemplary Y-shaped connector with a grasping tab, in accordance with an embodiment of the present specification.

FIG. 4B illustrates a perspective view of an exemplary Y-shaped connector 408, in accordance with an embodiment of the present specification. FIG. 4C illustrates a perspective drawing of the Y-shaped connector 408 of FIG. 4B, in accordance with an embodiment of the present specification. FIG. 4D illustrates another view of the Y-shaped connector 408 of FIG. 4B that is positioned within the disposable component 400 and attached to the feeding system, in accordance with an embodiments of the present specification. Referring simultaneously to FIGS. 4B, 4C, and 4D, Y-shaped connector 408 may include an external protrusion 410, also referred to as a grasping tab, at its center and protruding outwards in the form of a flat disc with a curved front surface that provides an ergonomic means to hold the connector. In some embodiments, the flat horizontal surface with the curved edge extends frontwards up to a length of approximately 0.25 inches. Protrusion 410 is an alternative embodiment to protrusion 310 of FIG. 3B and may be used in a similar manner and is similarly positioned towards a bottom central portion of connector 408. Protrusion 410 may be used for a snap/friction-fit attachment and/or detachment with/from the body of the enteral pump system 400. Connector 408 may be pressed against a specified location on the enteral pump system 400 to attach it with the system. Attaching the disposable tube set using the Y-shaped connector 408 with the aid of protrusion 410, provides greater structural integrity to the tube set. Protrusion 410 also allows for better retention and is little longer to assist with getting tubing around the bend to avoid dragging. It should also be appreciated that the enteral pump system 400 comprises a groove or channel 481 to receive the disposable tube set that extends substantially vertically across the face of the enteral pump system 400 and further comprises grooves 471 extending horizontally off of groove or channel 481 configured to receive the side edges of protrusion 410.

Figure 5C:
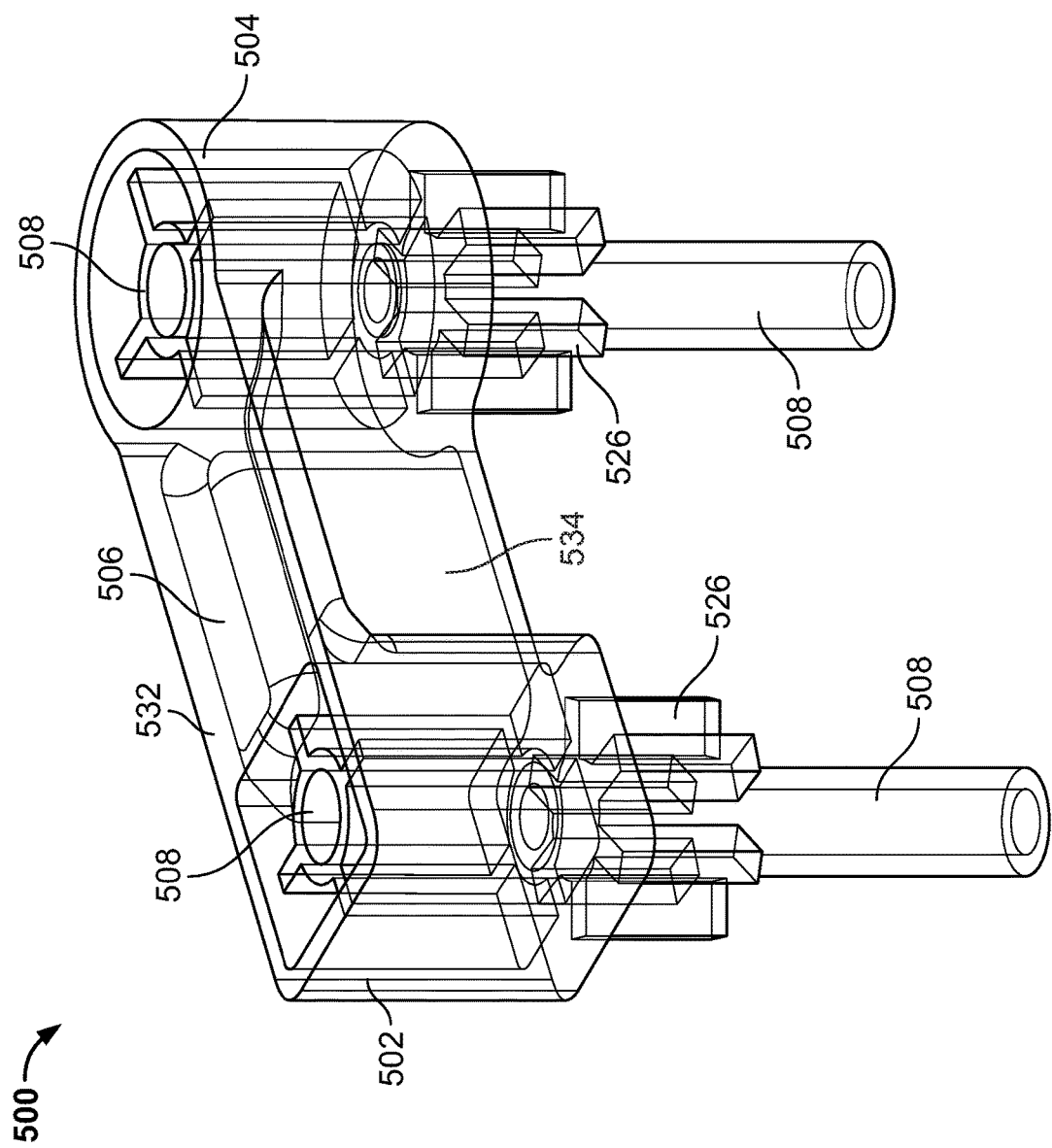
FIG. 5C illustrates a front perspective isometric view of the attachment portion of FIG. 5A used for attaching the disposable component to an enteral device in accordance with some embodiments of the present specification.
Figure 5D:
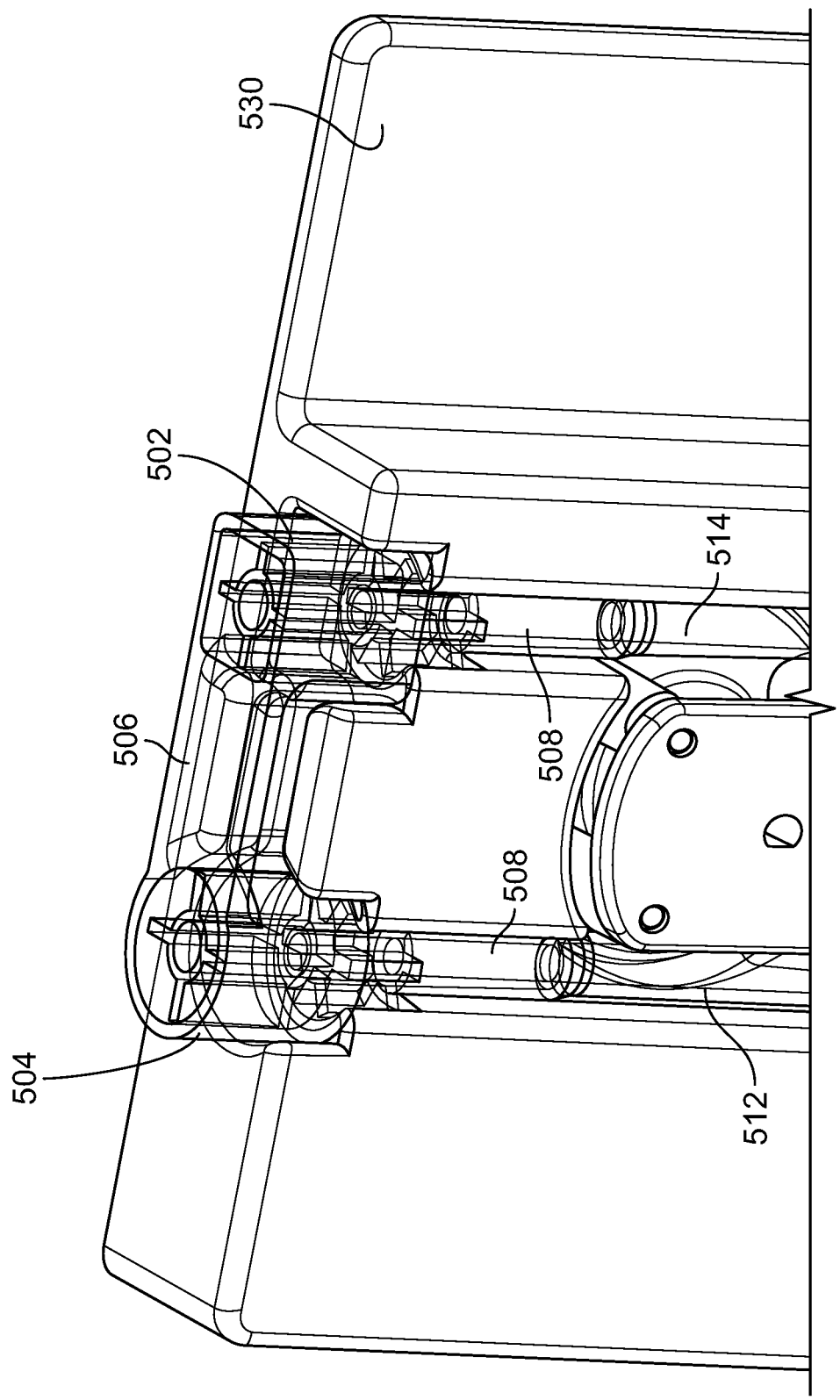
FIG. 5D illustrates a front perspective isometric view of the attachment portion of FIG. 5A attached to an enteral device in accordance with some embodiments of the present specification.
Figure 5F:
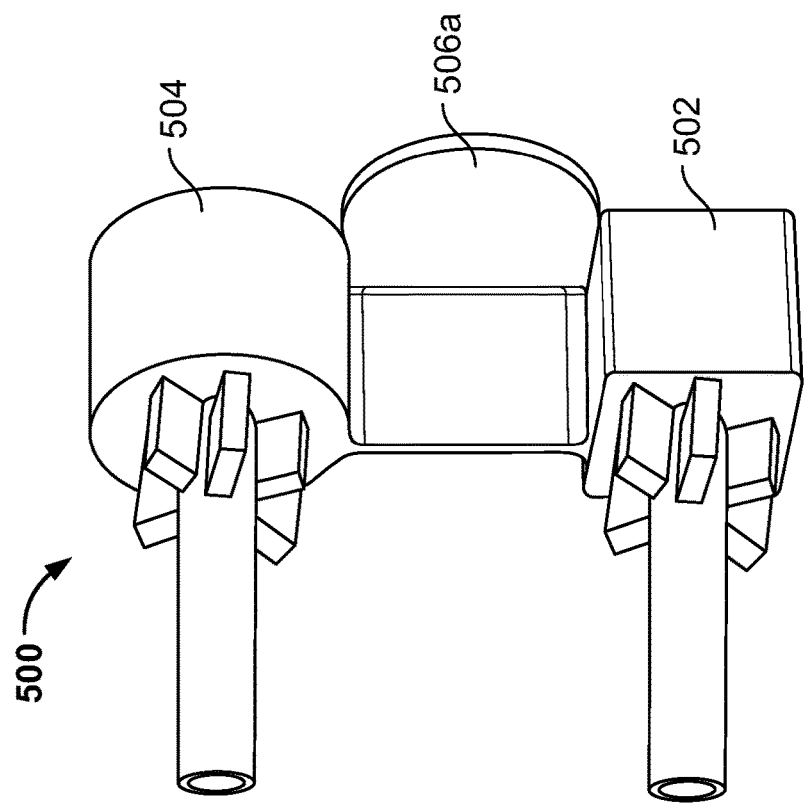
FIG. 5F illustrates a bottom perspective view of an attachment portion, in accordance with the alternative embodiment of FIG. 5E of the present specification.
Figure 5E:
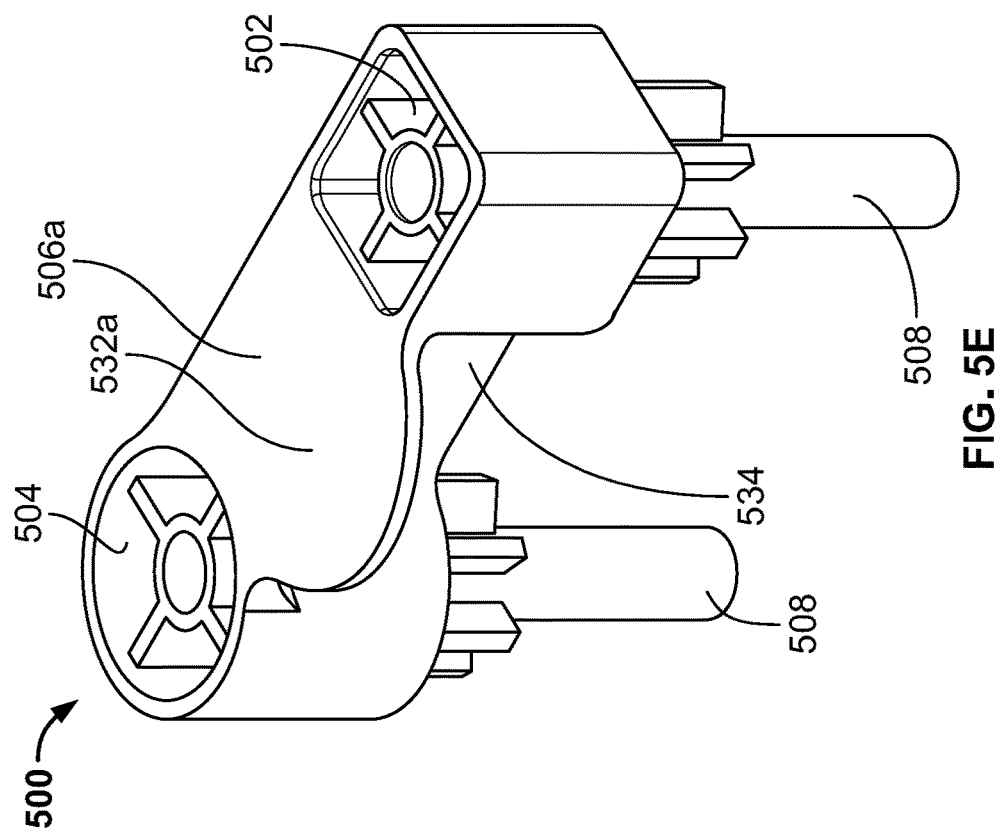
FIG. 5E illustrates a top perspective view of an attachment portion, in accordance with an alternative embodiment of the present specification.

FIG. 5A illustrates a front perspective view of an attachment portion 500 used for attaching the disposable component to an enteral device at the top of the prongs, in accordance with some embodiments of the present specification. FIG. 5B illustrates a bottom perspective view of the attachment portion of FIG. 5A used for attaching the disposable component to an enteral device at the top of the prongs, in accordance with some embodiments of the present specification. FIG. 5C illustrates a front perspective isometric view of the attachment portion of FIG. 5A used for attaching the disposable component to an enteral device at the top of the prongs, in accordance with some embodiments of the present specification. FIG. 5D illustrates a front perspective isometric view of the attachment portion of FIG. 5A attached to an enteral device at the top of the prongs, in accordance with some embodiments of the present specification. FIG. 5E illustrates a top perspective view of an attachment portion, in accordance with an alternative embodiment of the present specification. FIG. 5F illustrates a bottom perspective view of an attachment portion, in accordance with the alternative embodiment of FIG. 5E of the present specification. Referring simultaneously to FIGS. 5A, 5B, 5C, 5D, 5E, and 5F, an attachment portion 500 is also used as a cartridge connecting device, in addition to its use as a rigid attachment system for attaching a disposable component, such as the ones shown in FIGS. 3A and 4A, to an enteral device 530. Attachment portion 500 comprises two parts 502 and 504 combined to each other with a bridge-like structure 506. Embodiments of FIGS. 5E and 5F illustrate an alternative configuration of bridge-like structure 506a, which has a smooth curved edge protruding frontwards. In some embodiments, the curved edge extends frontwards by approximately 0.25 inches and enables users to manipulate positioning of attachment portion 500 into the enteral device 530. The attachment portion 500 is made of a material with a higher durometer range (less compliant) than the prongs 302, 304 or outlet tubing/pipe 312, thereby enabling a solid, rigid attachment to the enteral feeding device.

In one embodiment a first portion 502 is square-shaped and a second portion 504 is circular-shaped. In an alternative embodiment, the shape of first portion 502 is circular and second portion 504 is square. In other embodiments, shapes of first and second portions 502 and 504 are different from each other. In yet other embodiments, shapes of first and second portions 502 and 504 are similar, but they are of different colors. Various shapes of first and second portions 502 and 504 may include one or more of circular, square, rectangular, triangular, or any other shape. Different shapes and/or colors of the two portions 502 and 504 enable a user to distinguish the portion used to connect a food bag from the portion used to connect a bag of fluids. Portions 502 and 504 are hollow. Within each hollow portion 502 and 504, is a conduit 508. Conduits 508 are preferably circular, rigid, elongated tube-like structures. Each conduit 508 is centrally positioned within its corresponding portion 502 and 504. In some embodiments, conduit 508 is connected to the internal walls of the hollow of its corresponding portion 502/504. In some embodiments, conduit 508 is connected on at least one side, two sides, three sides, four sides, or with a flat circular disc-shaped structure around a circumference of conduit 508. The illustration shows each conduit 508 is joined from its outer circumference to the internal hollow wall of its corresponding portion 502/504, on four sides. In embodiments, the hollow tubular length of each portion 502/504 is shorter relative to tubular length of its conduit 508. In embodiments, conduits 508 within each portion 502 and 504 are of identical length. Conduit 508 extends from within a top opening of portion 502/504, along the internal length of portion 502/504 and further outwards from bottom of portions 502/504. Bottom extended length of conduit 508 is configured to receive and connect with a prong 512 or 514 of the disposable component. Each conduit 508 leads to respective food or fluid bag and enables movement of their contents into the respective food or fluid prong 512/514.

In some embodiments, a top side 522 of each portion 502 and 504 is open such that its corresponding conduit 508 can be seen from the top along with the connections that attach conduit 508 to its portion. In some embodiments, a bottom side 524 of portions 502 and 504 is closed around the outer surface of conduit 508, thus allowing only conduit 508 to pass through the bottom while sealing the area around it. In some embodiments, a circular corrugated gear-like structure 526 is configured surrounding conduit 508 and extending from bottom side 524 to a portion of conduit 508, along the length of conduit 508 that extends towards prongs 512 and 514. In alternative embodiments, structure 526 has a smooth surface and not a corrugated surface. In other embodiments, structure 526 is of any other shape. Structure 526 may be used for snap-fit attachment with the body of the enteral device. For this purpose, a corresponding recess in the body of the enteral device is configured in a complimentary shape to that of structure 526 to receive structure 526 for attachment.

Bridge 506/506a connects the two portions 502 and 504. A flat horizontal rectangular plate 532 joins one side of portion 502 to a side of portion 504 at the top side of bridge 506. In FIGS. 5E and 5F, a flat horizontal plate 532a with a curved frontal edge joins one side of portion 502 to a side of portion 504 at the top side of bridge 506a. Beneath plate 532/532a, a vertical plate 534 extends along the lengths of portions 502 and 504. Vertical plate 534 is continuously perpendicular to a rear horizontal edge of plate 532/532a. An L-shaped space is therefore available at the bottom side of plate 532/532a, which may be used to attach the disposable component to the enteral device at the top of the prongs. This L-shaped recess may be received by a complimentary structure configured within the enteral device. Bridge 506/506a also provides a means for the user to hold the attachment and push it in place into the enteral device or remove it from its place of attachment with the enteral device. While the figures illustrate two embodiments for connecting the portions 502 and 504, and attaching them to the enteral device, other design/configurations of the attachment portion are also possible. In some exemplary embodiments, bridge 506 includes a handle at the top, or a tab that protrudes outward and may be grabbed, or any other configuration that enables the user to handle the attachment to and removal of the disposable component from the enteral device.

Enteral Pump System

Figure 6:
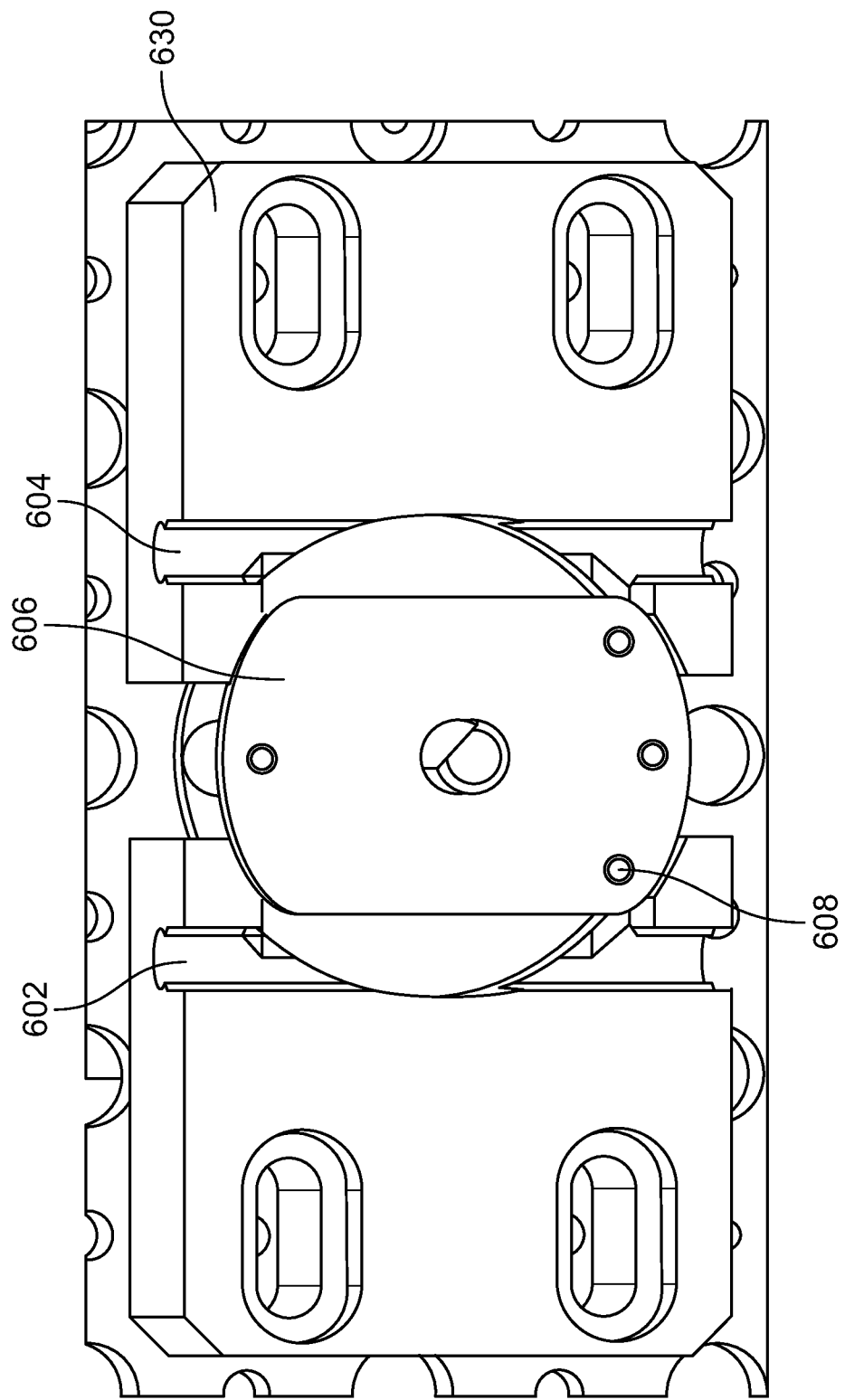
FIG. 6 illustrates a front view of a rotating pinch valve position set within an enteral device, in accordance with some exemplary embodiments of the present specification.

Referring again to FIG. 3A, the two parallel tube segments 302 and 304 are vertically aligned parallel to each other on opposing sides of the pinch valve 306. During operation, pinch valve 306 rotates clockwise and/or counterclockwise to cut-off fluid flow from one or both tube segments 302 and 304. Vertically, pinch valve 306 is placed between the inlets of prongs 302 and 304 along the parallel portions of prongs 302 and 304, and above Y-connector 308. FIG. 6 illustrates a front view of a rotating pinch valve 606 position set within an enteral device 630, in accordance with some exemplary embodiments of the present specification. In operation, pinch valve 606 rotates clockwise such that a pin 608 rotates towards the left side on to a channel 602, which is configured to position a tube/prong from an inlet. Therefore, by rotating clockwise, pin 608 of pinch valve 606 introduces a pinching effect to obstruct fluid/feed flow within the tube/prong positioned within channel 602. Similarly, by rotating in a counter-clockwise direction pin 608 of pinch valve 606 introduces a pinching effect to obstruct fluid/feed flow within the tube/prong positioned within a channel 604. Pin 608 forces the tube together and creates a seal that is equivalent to the tube's permeability. As a result of the pinching action, contents of the corresponding tube/prong are isolated from the remaining path of the tube/prong.

Referring again to FIG. 3A, at least two sensors are placed on either sides of the prongs 302 and 304 below pinch valve 306 and Y-connector 308. Single peristaltic rotor pump 314 is configured between connector 308, along path of the outlet pipe 312, and outlet 318. Action of the pump 314 operates to cause fluid to flow through tubing 312. In embodiments, outlet pipe is in physical communication with at least a portion of the circumference of the pump 314. Pinch valve 306 and pump 314 are fixed on the enteral pump system.

Figure 7A:
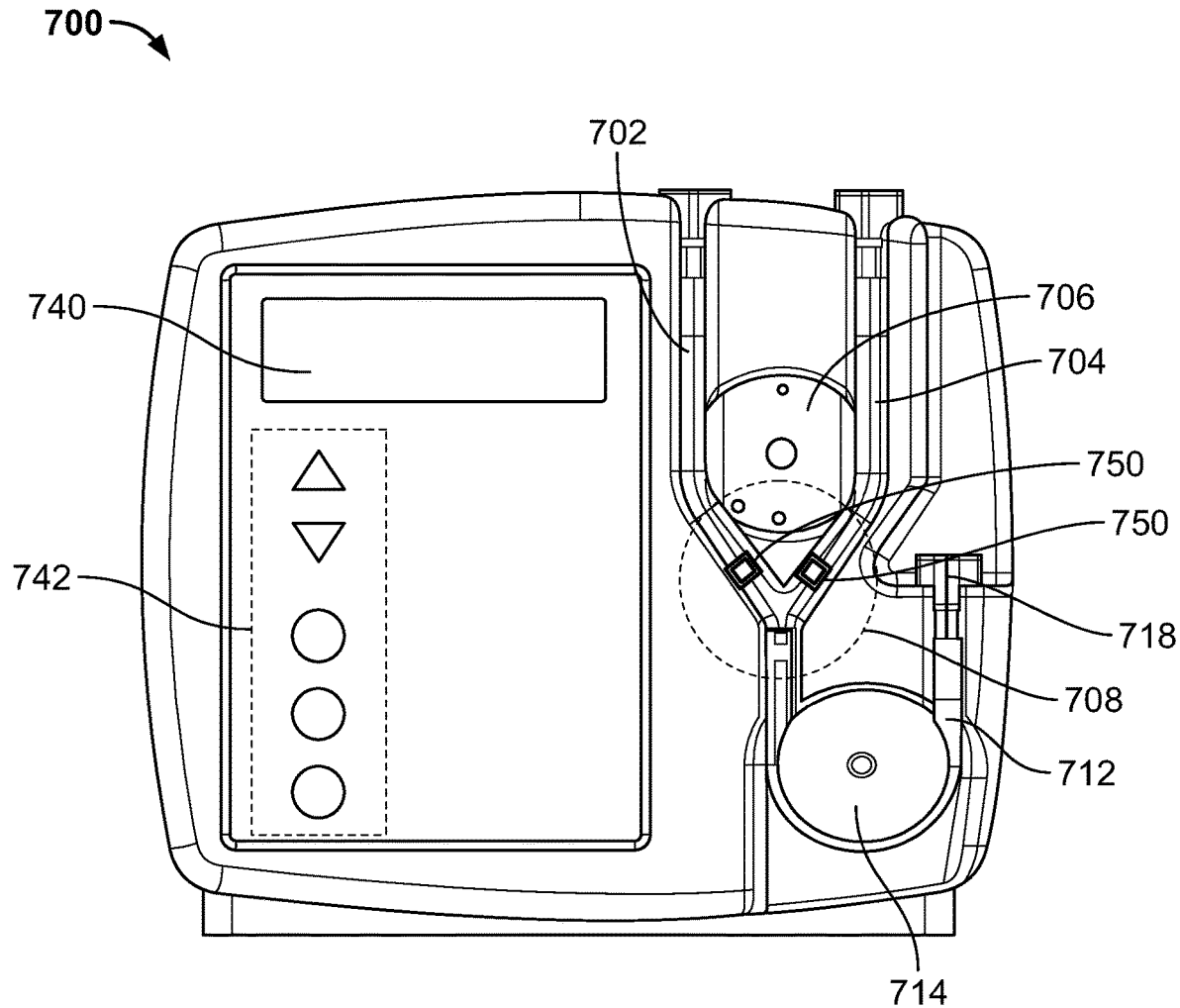
FIG. 7A illustrates a front view of an enteral device with a mounted disposable component and a first set of highlighted sensor positions in accordance with embodiments of the present specification.

FIG. 7A illustrates an enteral pump system 700 with a disposable component in accordance with embodiments of the present specification. Enteral pump system 700, also termed herein as enteral device 700, uses an enteral feeding set that may be used to deliver enteral formula and fluids to a patient. Enteral device 700 is portable and may be used with convenience by an ambulatory patient. In embodiments, device 700 enables a user to load the disposable component from a front side, which is the side that faces a user. The disposable component comprises two prongs 702 and 704 configured for dual use of feeding and flushing; a Y-shaped connector 708 connecting the two prongs 702 and 704 to an outlet pipe 712 that is also a part of the disposable component. Additionally, the disposable component incorporates a snap-fit connector 716 at the top, a friction connector behind the Y-shaped connector 708, and another snap-fit connector (outlet) 718 at the outlet of outlet pipe 712. Connectors 708, 716, and 718 provide points of attachment to engage the disposable component with the body of the enteral device 700. A pinch valve 706 is positioned between the parallel portions of the two prongs 702 and 704. During operation, pinch valve 706 moves from side to side to cut-off fluid flow. A rotor pump 714 is positioned such that outlet pipe 712 is guided along the surface of rotor pump 714 to ensure there is no bending. In embodiments, a display 740 is incorporated on one side of the enteral pump system 700. One or more buttons 742 may also be provided near display 740 to enable the user to interface with the enteral pump system 700. In some embodiments, primary text displayed on display 740 may be a minimum of 0.6 inches in height. Primary text may include a setting number or value being adjusted (Dose, Rate, Time). Primary text may also include all alarm or error messages. Secondary text may including label and may be a minimum of 0.3 inches in height. In some embodiments, the display may have a minimum contrast of 4:1 in brightness of the characters to the background when active. In some embodiments in accordance with the present specification, display 740 integrated within the enteral device 700 is viewed from a vertical angle ranging from −30 degrees to +30 degrees. Controls/button 742 for the display may be operated from an angle of approach of + or −30 degrees from vertical.

In embodiments, optical sensors are provided below pinch valve 706, but above Y-shaped connector 708 along each prong 702 and 704 of the disposable component. FIG. 7A illustrates the position of the optical sensors within squares 750 shown in the figure. In an embodiment, the optical sensors are at the position of the squares and are located in the enteral pump system 700 behind the tubing set comprising the two prongs 702 and 704. In embodiments, an optical sensor is also provided between rotor pump 714 and outlet 718. In alternative embodiments, other types of non-invasive sensors may be used in place of or in addition to the optical sensors.

The sensors are configured to detect occlusions and also detect the type of disposable component used. For example, if all three sensors are activated/triggered, they would indicate use of a dual-mode disposable set meant for feeding and flushing. However, if only two of the three sensors are activated/triggered, then they would indicate the single-mode meant for feeding purposes. In some embodiments, data from the three different sensors are received by a controller and then processed to determine the presence of two prongs or one prong. If two prongs, then the enteral pump system 700 is identified to be in one mode. If one prong, then the enteral pump system 700 is identified to be in the other mode. The sensors also detect whether the two prongs 702, 704, and the outlet channel 712—the three legs of the disposable component are installed properly. In case the patient is unable to attach them properly, the sensors may trigger one or more alarms, visual and/or auditory, which indicate the need to attach the disposable component properly. The location of the sensor that is triggered may indicate the part of the disposable component that requires further attention or adjustment to achieve proper attachment with the enteral device 700. The sensors may further detect motion of rotor pump 714. Additionally, the sensors help avoid false occlusion alarms by having at least two independent methods of detection. It should be appreciated that the sensors are configured to generate a signal indicative of the presence of a tube segment or indicative of the presence of a specific type of tube segment and transmit the signal to a controller or processor located in the enteral feeding device. The controller or processor is configured to then process the signal to determine the presence of the tube segment or the presence of the specific type of tube segment.

Additionally, the sensors may be used to detect an occlusion in the tubing. In a first method of detecting occlusion, optical sensors may use Infra-Red (IR) optical through beam technology with discrete LED/photo-transistor pairs. The LED current may be controlled by a Microprocessor Control Unit (MCU) embedded within device 700. The optical sensors transmit a signal through each prong 702 and 704, one of which is a tube for feed and the other is a tube for fluids such as water. A sensor on either side of each prong 702 and 704, positioned between the pinch valve 706 and the Y-shaped connector 708, detect through the prongs 702 and 704. If, once the pinch valve 706 is closed, the optical sensors detect a significant change in an optical signal, its corresponding tube (prong 702 or prong 704) is considered void and it may be concluded that a downstream occlusion does not exist. If however, while the pinch valve 706 is closed, the optical sensors detect no change in optical signal in either tube, the tube where no change is detected may be interpreted to have full or partial downstream occlusion. In some embodiments, the tubes (prongs 702 and 704) are manufactured using silicone. In certain embodiments, the signal may change over a course of time, indicating partial occlusion. The occlusion may be thereafter corrected by interrupting the normal pumping cycle.

Figure 7B:
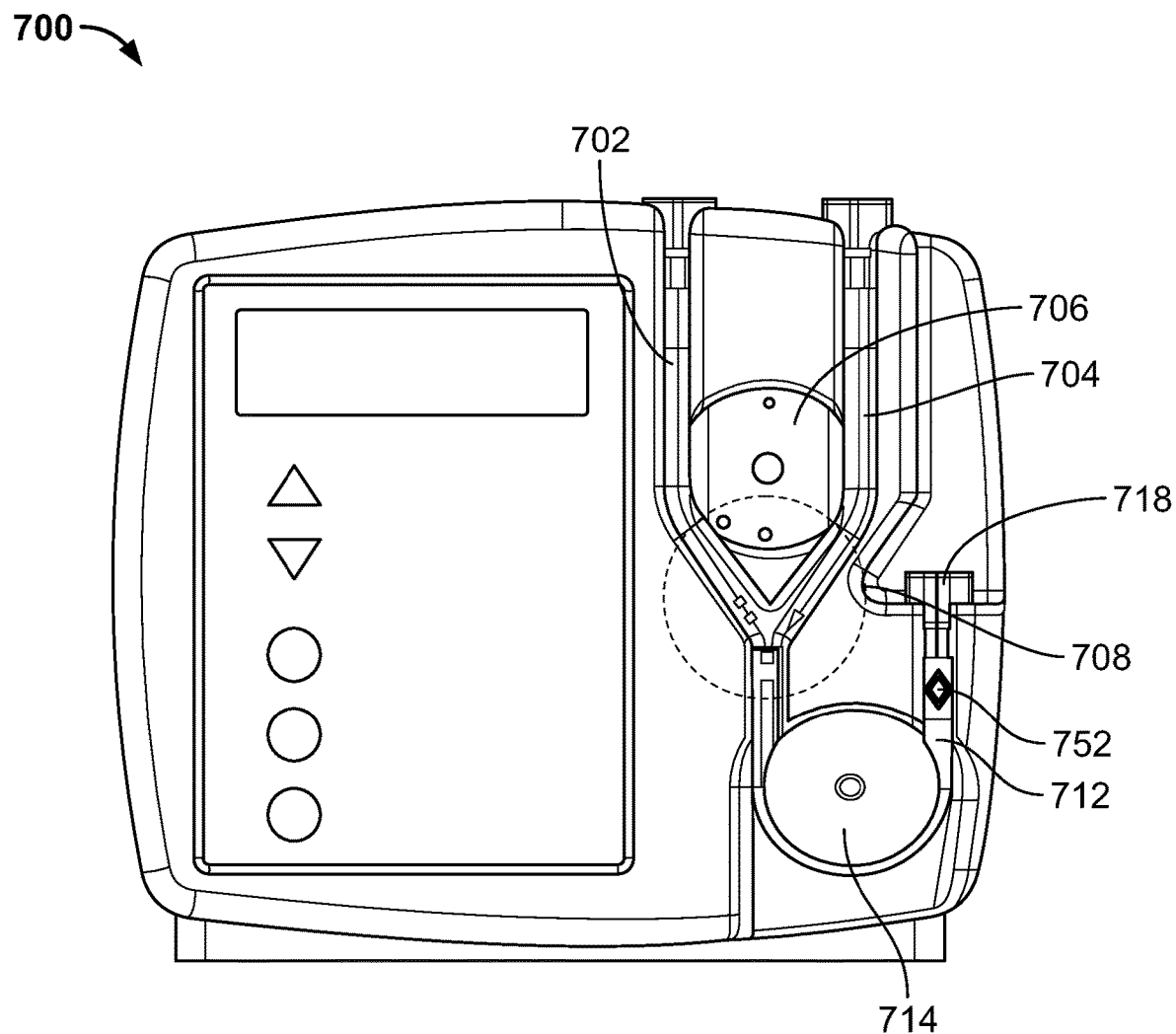
FIG. 7B illustrates a front view of an enteral device with a mounted disposable component and a second highlighted sensor position in accordance with embodiments of the present specification.

FIG. 7B illustrates enteral device 700 of FIG. 7A that is used to detect occlusion according to another method in accordance with some embodiments of the present specification. A third optical sensor 752, positioned next to outlet channel 712 and between the rotor pump 714 and the output connector 718, detects through channel 718. Optical signal decreases as pressure builds in output channel 712, indicating occlusion. The optical signal may be weaker than the signals detected for occlusion in the first method comprising two sensors and explained in context of FIG. 7A, however, the signal detected by the third optical sensor may respond faster.

In preferred embodiments, the first and the second methods of FIG. 7A and FIG. 7B are combined in order to use all three sensors simultaneously to detect occlusion with fewer false positives. Presence of feed set disposable component may be detected using the optical sensors. Low current or light intensity condition may indicate presence of the tube used for feeding. Alternatively, low current or light intensity may be used to detect an empty tube as opposed to containing water in the tube meant for fluids. In an embodiment, high current condition may indicate an empty tube as opposed to a feed tube filled with formula/food.

In some embodiments, the sensors are additionally used to detect an empty enteral device 700, where the disposable component has not been attached. In some embodiments, an empty disposable component is detected when air in the tube is sensed by a dramatic increase in the feed sense signal and a decrease in the water/fluid sense signal.

Figure 8:
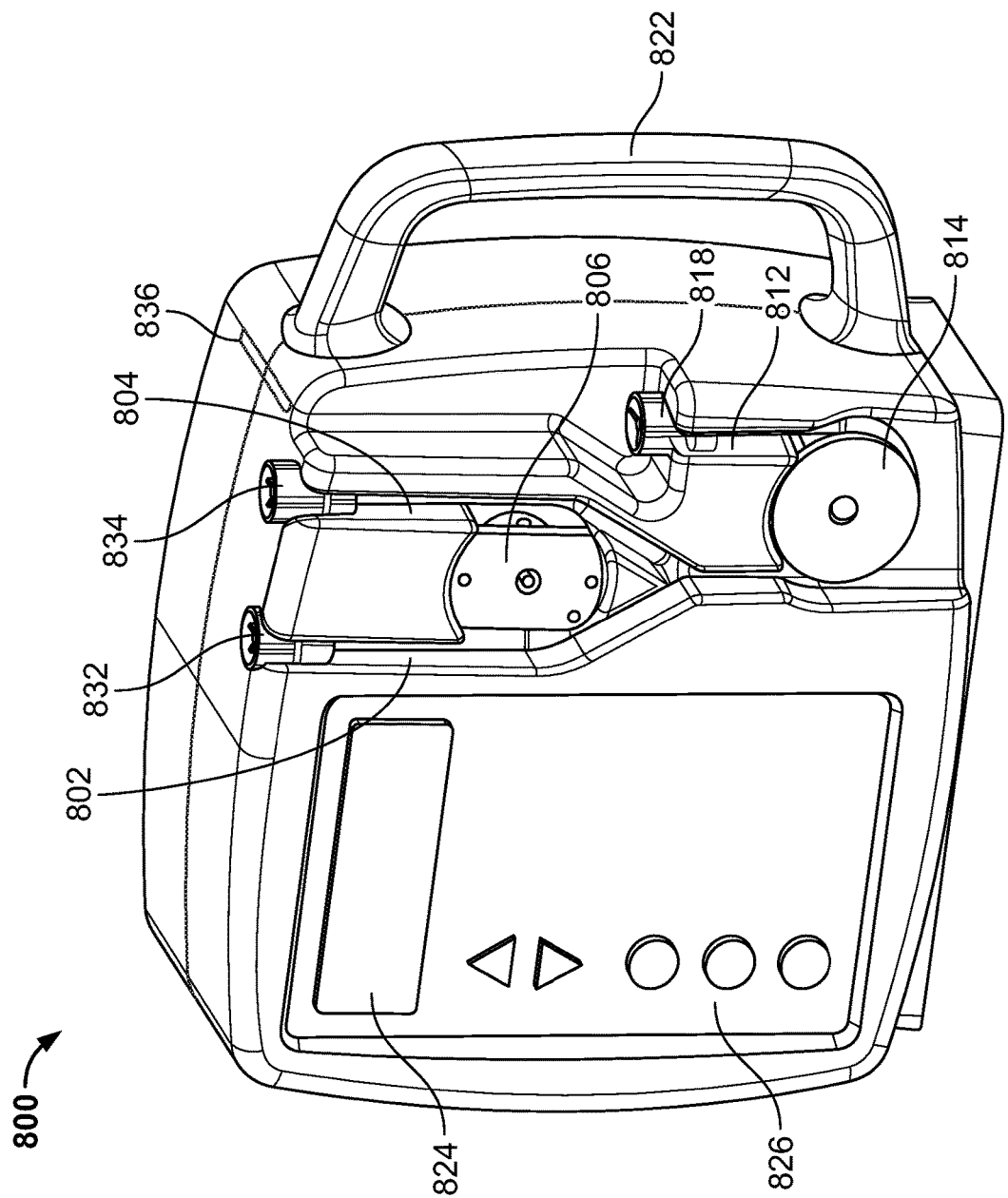
FIG. 8 illustrates front perspective view of an enteral device with a raised handle, in accordance with some embodiments of the present specification.

FIG. 8 illustrates front perspective view of an enteral device 800 with a raised handle 802, in accordance with some embodiments of the present specification. Device 800 is in the form of a housing. A front surface of the housing comprises parallel channels 802 and 804, a pinch valve 806, an outlet channel 812, a rotary pump 814, and a user interface, among other components. Device 800 comprises parallel vertical channels 802 and 804 configured to receive feed and flush pipes/prongs of a disposable feeding tube component such as the one described in context of FIG. 4. An inlet channel 832 is configured at the inlet position of channel 802 to receive the inlet of one of the pipes used for feeding or flushing. Similarly, another inlet channel 834 is configured at the inlet position of channel 804 to receive the inlet of the other of the pipes used for flushing or feeding. While mounting a disposable component, a bridge connector between the two inlets of the prongs may be snap-fitted on to channels 832 and 834. A pinch valve 806 extends out from the front face of device 800 between the parallel channels 802 and 804. Pinch valve 806 is configured to overlap partially with at least of the channels 802 and 804, when operated. Pinch valve 806 is configured to control flow through the tubes mounted onto the channels 802 and 804. Below the pinch valve 806, the two parallel channels 802 and 804 merge into the two top arms of a Y-shape. At this juncture, the disposable component comprising a Y-shaped connector may be attached using a friction-fit attachment method. The merged channels form a single outlet channel 812, which curves around a pump 814 towards another opening 818 at the exit of outlet channel 812 and configured to receive a connector of the disposable component which contains the outlet.

Pump 814 is configured to provide data to a controller, which the controller uses to control the operation of the pinch valve 806. Channel 812 is configured to receive an outlet pipe of the disposable component. Opening 818 may be configured to receive the outlet connector using a friction-fit attachment. Optionally, although preferably, the pump 814 extends outward from the front surface face of the enteral feeding pump system 800 and is not encased or otherwise covered by a housing. Pump 814 may be a rotary pump and is configured to control the passage of feed and/or fluids through the disposable components' prongs and outlet pipe. by controlling the pinch valve 806 via a controller.

In embodiments, optical sensors are provided below pinch valve 806, but above Y-shaped portion along each channel 802 and 804 of the disposable component. FIG. 7A illustrates the position of the optical sensors 750 within squares shown in the figure. In an embodiment, the optical sensors are at the position of the squares, and are located in the enteral pump system 700/800 behind the tubing set comprising the two prongs 702 and 704. In embodiments, an optical sensor is also provided between rotor pump 814 and opening 818 at the end of outlet channel 812. In alternative embodiments, other types of non-invasive sensors may be used in place of or in addition to the optical sensors. The sensors detect occlusions and also detect the type of disposable component used.

A handle 822 is an attachment on a side of a body of the device 800, connected at two ends of the side surface of device 800. The two connected ends are joined perpendicularly by a straight or a slightly curved structure such that a user may fold in their fingers to grasp handle 802, within the space between the side surface and the straight/slightly curved structure, for holding, moving or lifting device 800.

A user interface comprising a display 824 and one or more controls 826 may be provided on one side of the front face of device 800.

Figure 9A:
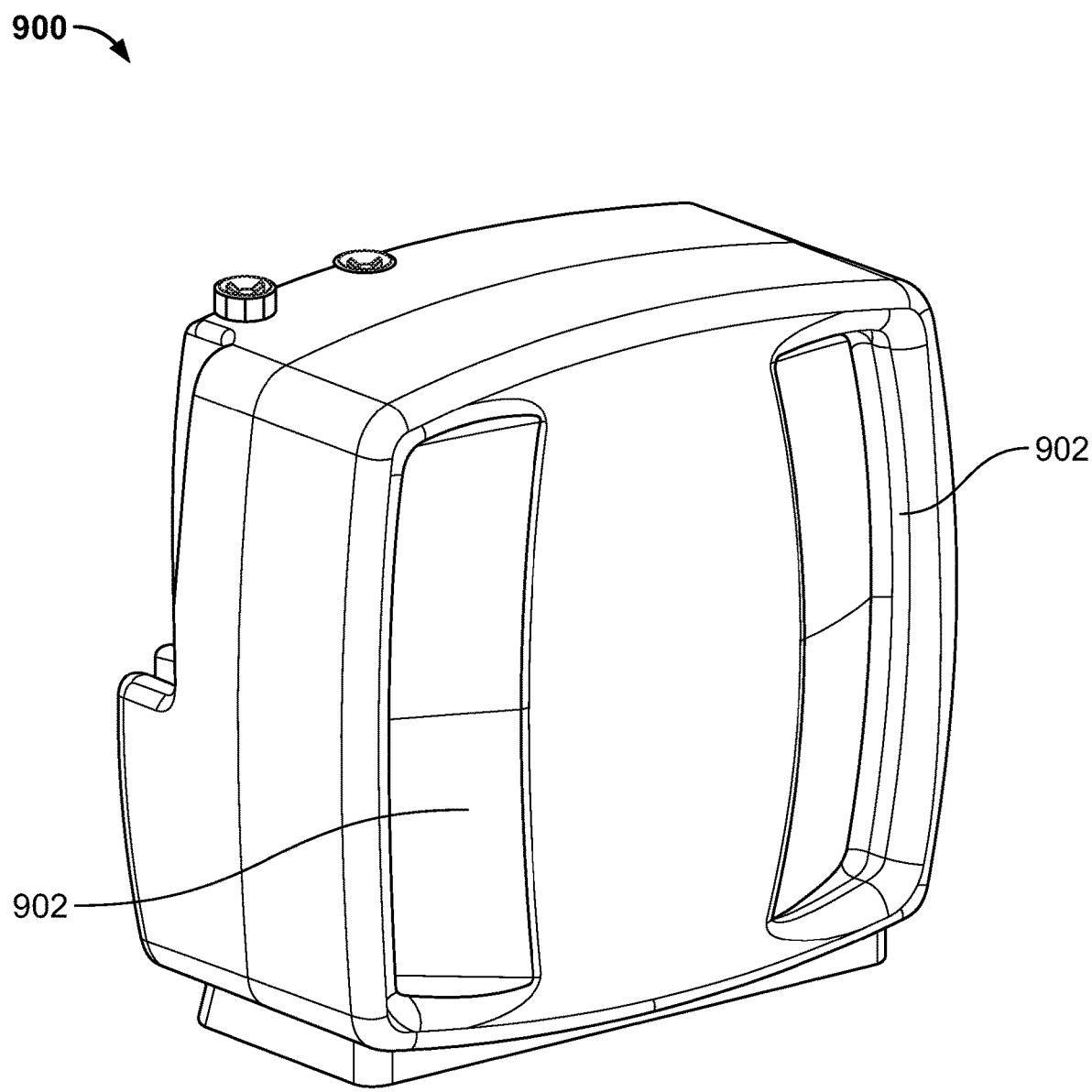
FIG. 9A illustrates a back perspective view of an enteral device with recesses to grip device, in accordance with some embodiments of the present specification.
Figure 9B:
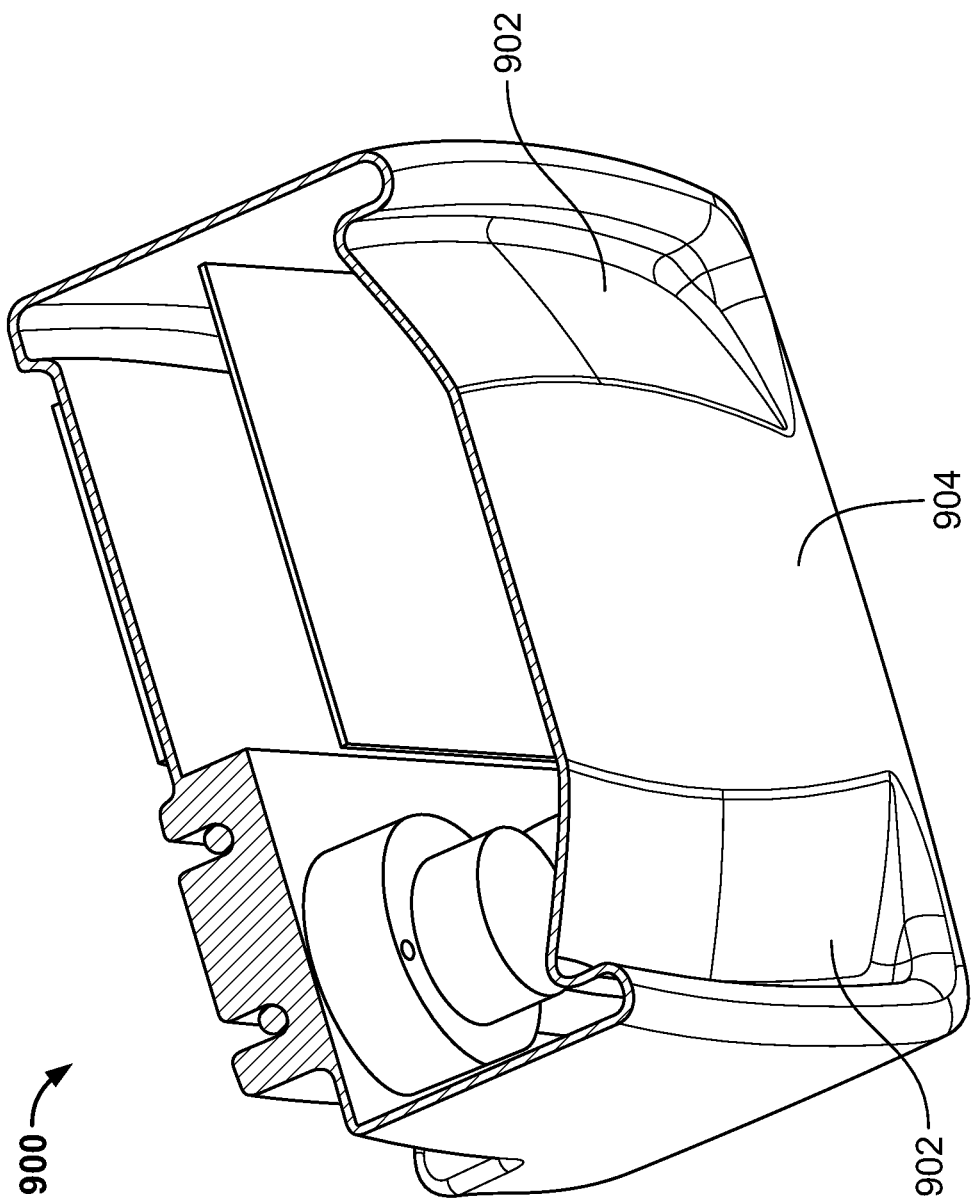
FIG. 9B illustrates a bottom cross-section of the back perspective view of the enteral device with recesses, in accordance with some embodiments of the present specification.
Figure 9C:
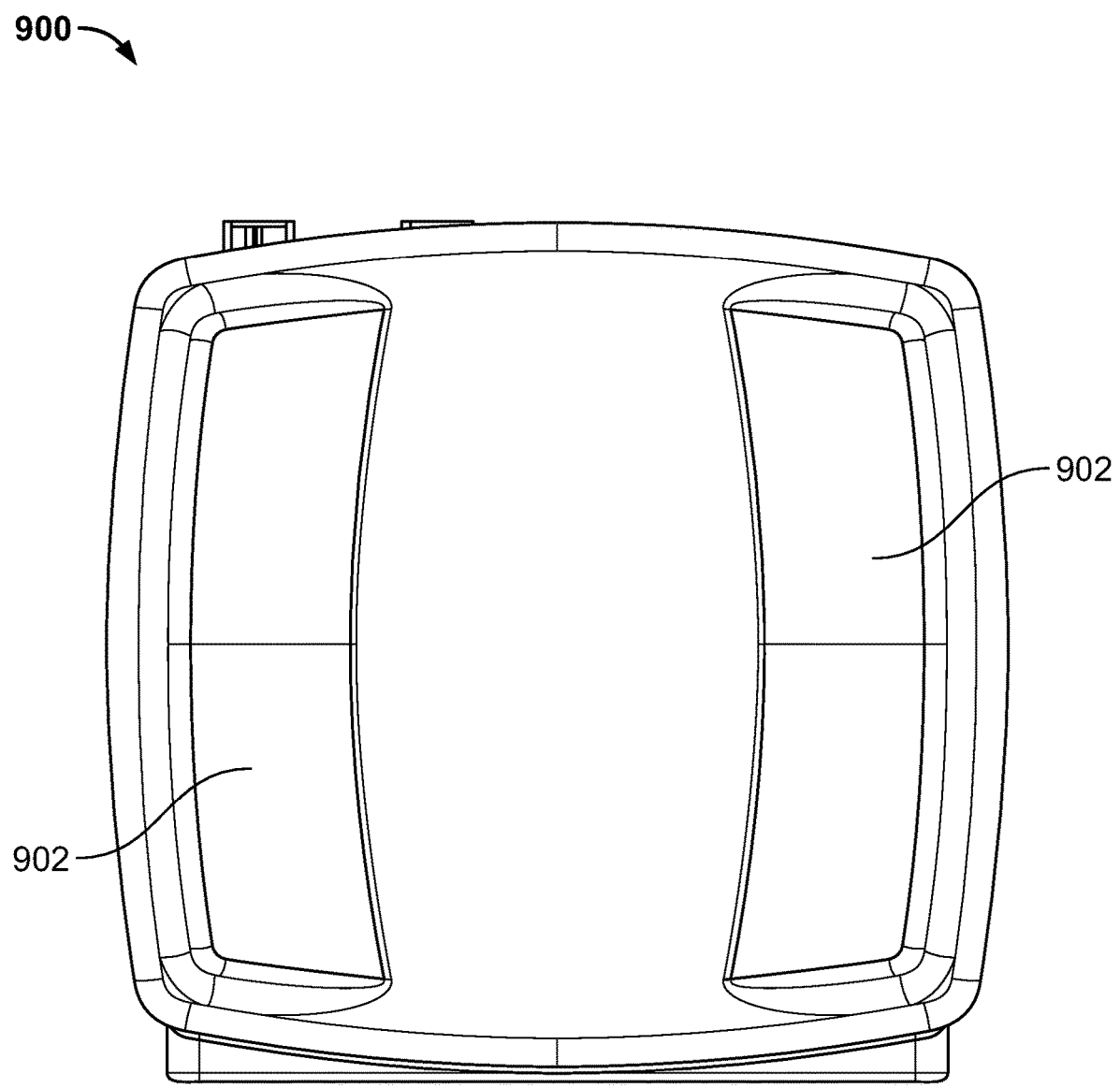
FIG. 9C illustrates a back view of the enteral device with recesses, in accordance with some embodiments of the present specification.

FIG. 9A illustrates a back perspective view of an enteral device 900 with recesses 902 to grip device 900, in accordance with some embodiments of the present specification. FIG. 9B illustrates a bottom cross-section of the back perspective view of the enteral device 900 with recesses 902, in accordance with some embodiments of the present specification. FIG. 9C illustrates a back view of the enteral device 900 with recesses 902, in accordance with some embodiments of the present specification. Referring simultaneously to FIGS. 9A, 9B, and 9C, a back surface 904 of device 900 has a curvilinear surface with vertically elongated recesses 902 at its two opposite sides. In embodiments, back surface 904 is the surface opposite to a front side/surface of device 900, where the front side comprises a user-interface and a place to position disposable component for enteral feeding. In some embodiments, each recess 902 has a slanting surface that slants from towards the centre of surface 904 inwards towards the edge of surface 904, such that the surface of the recess along and near the centre of surface 904 is at level with surface 904, and its other side along an edge of surface 904 is at a depth inwards from surface 904. Recesses 902 may provide users a place to position their fingers while gripping device 900, for holding, moving, or lifting device 900.

Figure 10C:
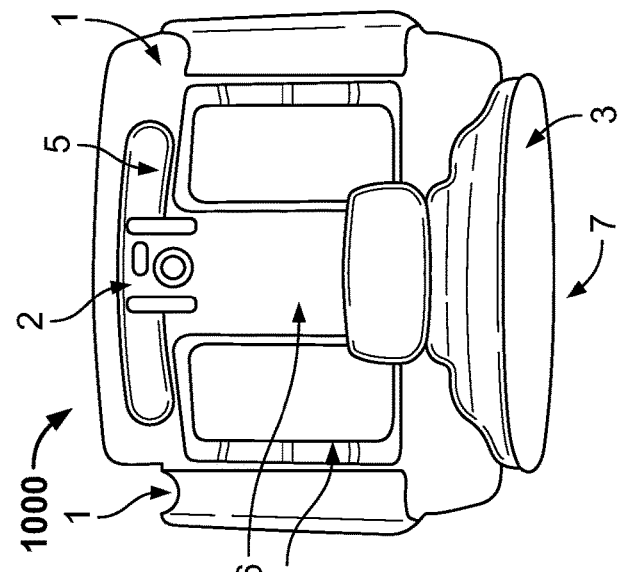
FIG. 10C illustrates a back view of the enteral device of FIG. 10A, in accordance with some embodiments of the present specification.
Figure 10B:
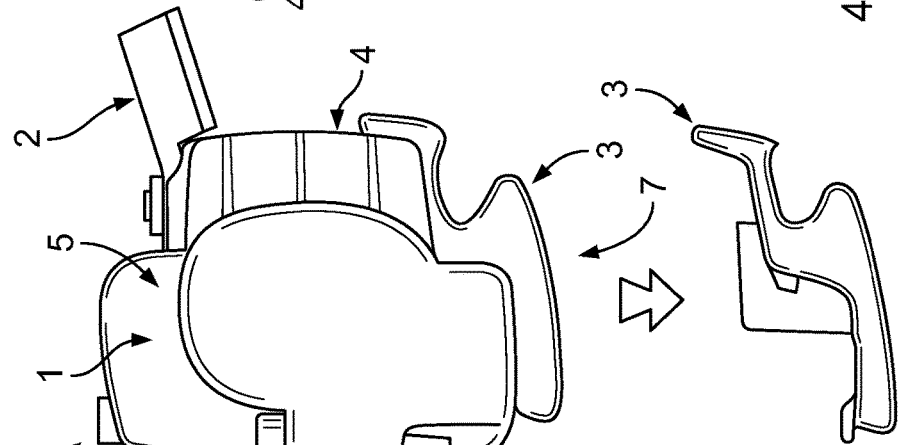
FIG. 10B illustrates a side view of the enteral device of FIG. 10A in accordance with some embodiments of the present specification.
Figure 10A:
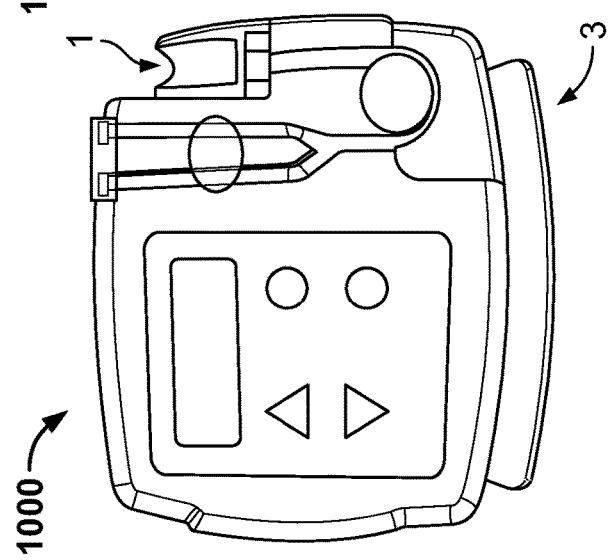
FIG. 10A illustrates a front view of an enteral device, in accordance with some embodiments of the present specification.

FIG. 10A illustrates a front view of an enteral device 1000, in accordance with some embodiments of the present specification. FIG. 10B illustrates a side of the enteral device 1000, in accordance with some embodiments of the present specification. FIG. 10C illustrates a back view of the enteral device 1000, in accordance with some embodiments of the present specification. Referring simultaneously to FIGS. 10A, 10B, and 10C, a curved surface 1 on a side of device 1000 provides a surface used to wrap an enteral tube extending from the device to the patient. Curved surface 1 may start from the portion of device 1000 where an outlet connector ends, extend from the end of outlet connector, curve around in circular trajectory and end near a bottom surface of a back side of device 1000. In some embodiments, curved surface 1, when viewed from side of device 1000, follows the curvature of the device and is intended to provide a pathway for the tubing to avoid having it become entangled.

In addition to curved surface 1, an indent 5 is provided in the form of a horizontally elongated recess at the top of a back side of device 1000, for holding and/or gripping. A pole clamp 2 may be provided at a centre of the top indent 5 on the back side of device 1000. The pole clamp 2 may be adjustable and may also serve as a cord retainer. In some embodiments in accordance with the present specification, the pole clamp 2 integrated with the enteral device is non-detachable, and which enables attaching the pump to a standard IV pole. A removable base 3 may be provided at the bottom base of device 1000. The removable base 3 provides a cover for a battery embedded within device 1000, and may be removed to access the battery. The base 3 may additionally provide an angled base for enabling device 1000 to stand and balance in an upright position when placed on a flat horizontal surface. A recess towards the back side of the base 3 may be used to retain a cord connected to device 1000. Also, above the recess, a horizontally elongated strip may be configured to hold a transformer of device 1000. Another pair of recesses 4 formed by wing-like structures that stretch vertically along two sides of the back surface of device 1000. The recesses encompass a storage pocket 6 from two opposite sides, where in the pocket the transformer may be stored.

Figure 11A:
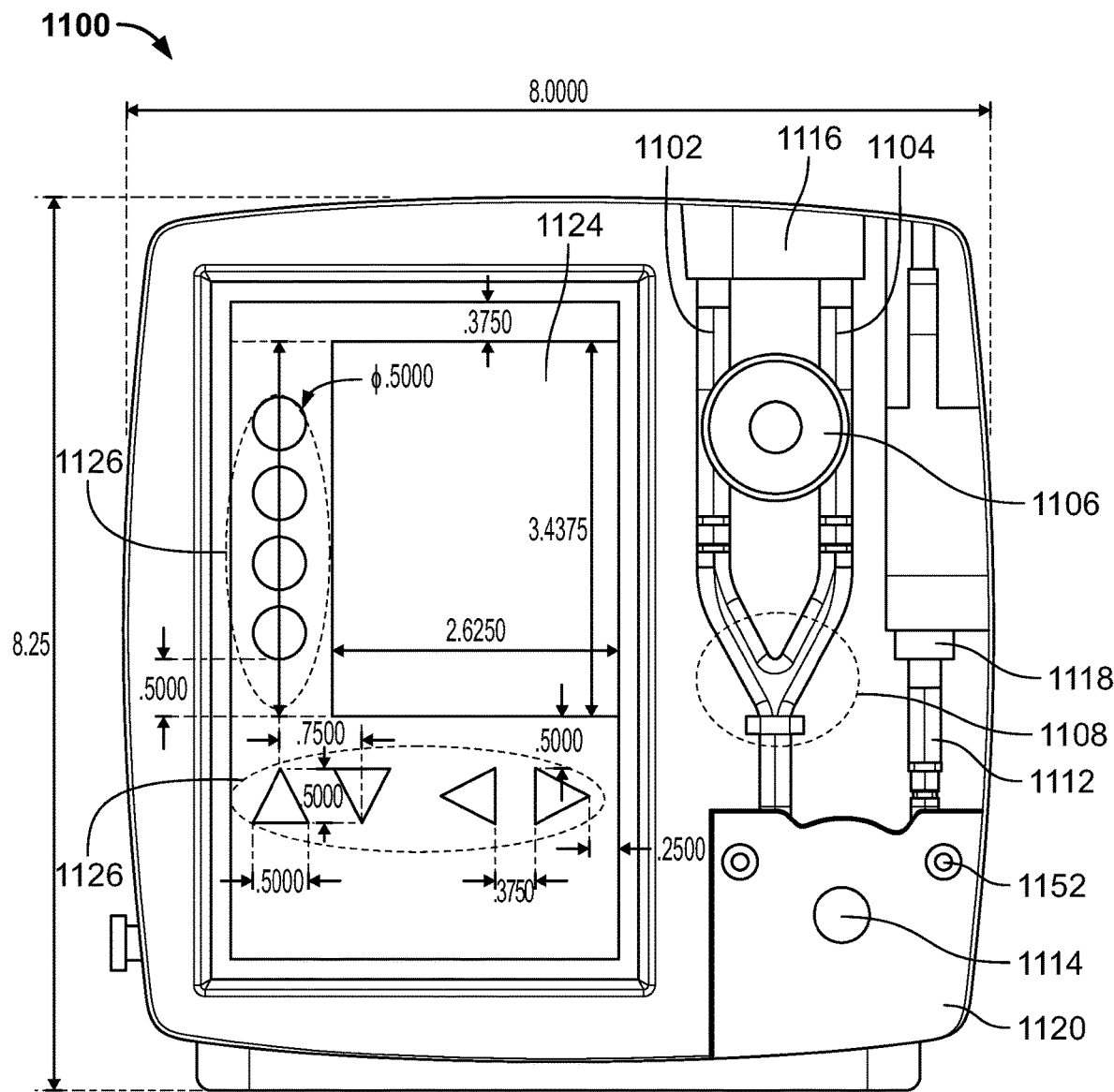
FIG. 11A illustrates a front perspective view of an enteral device, in accordance with some embodiments of the present specification.

FIG. 11A illustrates a front view of an enteral device 1100, in accordance with some embodiments of the present specification. Device 1100 is in the form of a front face of a housing. The front surface of the housing comprises parallel channels 1102 and 1104, a pinch valve 1106, an outlet channel 1112, a rotary pump 1114, and a user interface, among other components. In some embodiments, and as seen in FIG. 11A, a flat plate 1120 is fixed above rotary pump 1114 in order to cover and protect pump 1114. Device 1100 comprises parallel vertical channels 1102 and 1104 configured to receive feed and flush pipes/prongs of a disposable feeding tube component such as the one described in context of FIG. 4. A recess 1116 is configured to receive a connector that bridges inlet channels used for feeding or flushing. Recess 1116 receives the connector, such as connector 416 described in context of FIG. 4, for the placement of inlet channels of the pipes used for flushing or feeding. While mounting a disposable component, the bridge connector between the two inlets of the prongs may be snap-fitted on to recess 1116. A pinch valve 1106 extends out from the front face of device 1100 between the parallel channels 1102 and 1104. Pinch valve 1106 is configured to overlap at least partially with the channels 1102 and 1104, when operated. Pinch valve 1106 is configured to control flow through the tubes mounted onto the channels 1102 and 1104. Below the pinch valve 1106, the two parallel channels 1102 and 1104 merge into the two top arms of a Y-shape. At this juncture, the disposable component comprising a Y-shaped connector may be attached using a friction-fit attachment method. The merged channels, form a single outlet channel 1112, which curves around pump 1114 towards another opening 1118 at the exit of outlet channel 1112 and configured to receive a connector of the disposable component which contains the outlet. Pump 1114 is configured to control the operation of the pinch valve 1106. Channel 1112 is configured to receive an outlet pipe of the disposable component. Opening 1118 may be configured to receive the outlet connector using a friction-fit attachment. Pump 1114 extends outwards from the front face of device 1100. Pump 1114 may be a rotary pump and is configured to control the passage of feed and/or fluids through the disposable components' prongs and outlet pipe, by controlling the pinch valve 1106.

In embodiments, optical sensors are provided below pinch valve 1106, but above Y-shaped portion along each channel 1102 and 1104 of the disposable component. In embodiments, an optical sensor is also provided between rotor pump 1114 and opening 1118 at the end of outlet channel 1112. In embodiments, a sensor slot 1152 is configured on enteral device 1100 close to the channel extending between rotor pump 1114 and opening 1118. Slot 1152 is configured to position the optical sensor at this location. FIG. 11B illustrates a close view of slot 1152. In alternative embodiments, other types of non-invasive sensors may be used in place of or in addition to the optical sensors. The sensors detect occlusions and also detect the type of disposable component used.

A user interface comprising a display 1124 and one or more controls 1126 may be provided on one side of the front face of device 1100. In some embodiments, display 1124 and controls 1126 are provided on one half of the front surface of device 1100. FIG. 11 illustrates display 1124 and controls 1126 configured on the left half surface of device 1100. In an embodiment, a width of device 1100 is approximately 8 centimetres (cm), and a length of approximately 8.25 cm. Rectangular display 1124 may spread over a length of approximately 3.4 cm and a width of 2.6 cm. Circular buttons for controls 1126 may be provided on a side, such as the left side, of display 1124. In one embodiment, the circular buttons are positioned in a linear vertical arrangement along the length of display 1124. In an embodiment, each circular button has a diameter of 0.5 cm. Another set of controls 1126 may be provided in the form of triangular buttons arranged below the circular buttons and display 1124, along a width of display 1124. The triangular buttons may be used to control the movement of a pointer or of the screen seen on display 1124, in a direction indicated by the arrow of the corresponding triangular button. Display 1124 displays text and/or graphics corresponding to the operation of device 1100. Controls 1126 enable user/operator to browse through and possibly select options displayed on display 1124.

Figure 12:
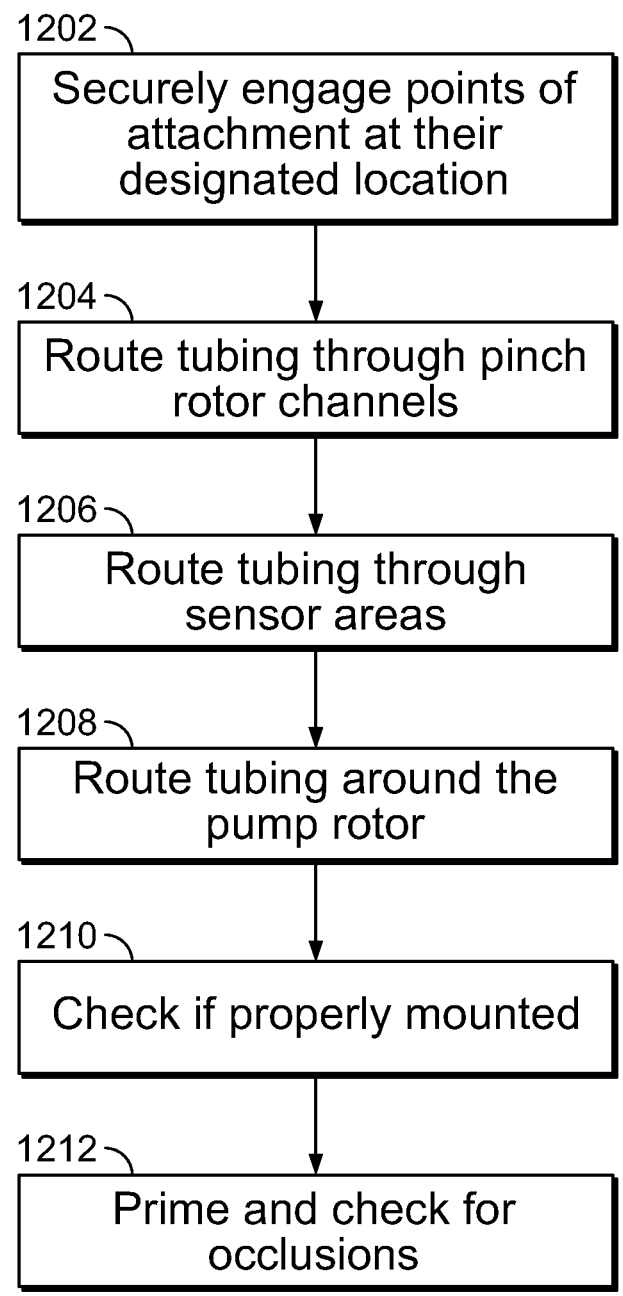
FIG. 12 is a flow chart illustrating exemplary steps of loading the disposable component of the feeding set into the enteral pump system, in accordance with some embodiments of the present specification.

Mounting the Disposable Component on to Enteral Pump System and Operating the System Embodiments of the enteral pump configurations in accordance with the present specification are used to supply nutrients into the gastro-intestinal system of a user. FIG. 12 is a flow chart illustrating exemplary steps of mounting the disposable component of a tubing set into an enteral pump system, in accordance with some embodiments of the present specification. In various embodiments, the feeding set, in accordance with the embodiments of the present specification, may be mounted on a pole or on a table. At 1202, while loading the feeding set (for either single or dual use), one or more points of attachment are securely connected or engaged at their designated locations. In some embodiments, a power cord attached to the device is plugged into a 120V power supply. At 1204, tubing is routed through the vertical pinch valve channels on the enteral pump system to insure proper flow control. At 1206, tubing is routed in sensor areas for proper sensing of tubing and liquid presence. The sensor areas comprise sensors located within the enteral pump system, and described subsequently in context of FIGS. 7A and 7C. At 1208, the tubing is routed around the pump rotor to ensure no free flow is possible and that pumping will move fluid properly.

At 1210, once the tubing set is mounted, then the system checks to determine if the tubing set is properly mounted. In one embodiment, proper mounting is checked by performing a check on the tension and stability of the tubing set by measuring tubing compliance using the pinch valve or rotor pump. In some embodiments, the system also checks if the tubing set is authorized. In one embodiment, a sensor is used to check a special code printed or embedded in the tubing set to determine whether it is authorized. In embodiments, the type of feed set (single use or dual use) is identified either automatically by the controller through the use of sensors, or manually indicated to the controller by the user. In an embodiment, the user indicates the type of feed set by selecting an option through the user-interface provided with the enteral pump system.

At 1212, the system is operated to prime the tubing set and check for occlusions. The feed set disposable component is checked for occlusions that may have occurred due to engagement of the points of attachment or due to routing of the tubes. The priming operation is performed using the sensors and while controlling the rotors. In some embodiments, at least three modes of priming are available. In a first mode, automated priming is performed. During automated priming, flush and fills to the Y-shaped connector are selected automatically from the flush side for feed and flush feed sets. Additionally, the automated mode selects feed and pumps feeding solution to within a foot of the patient tube for the approved feed sets. In a second mode, a 'top-off priming' operation is performed, wherein the controller sends a message to operator with the option to pump more feeding solution under the operator's control. In the second mode, the operator is provided manual control and is enabled to completely fill the patient tubing under observation. In a third mode, manual priming operation is provided. In this mode, the control system interacts with messages and sensors to lead the operator through priming of flush and feed. In embodiments of the third mode, the operator controls the amount of pumping through direct observations of liquids in feed set tubing.

In various embodiments, the enteral pump system of the present specification either automatically detects the presence of a single tube for feeding only or dual tubes for feeding and flushing. In some embodiments the user may be able to manually program the enteral pump system for single or dual use. A graphical user interface (GUI) may be provided with a display and controls for the user to view and control the operation of the enteral pump system. In embodiments, the enteral pump system of the present specification incorporates a microprocessor control unit (controller) to control the functioning of the system. The controller may provide appropriate messages, prompts, alarms, and information to the user for smooth operation of the system. In some embodiments, the controller facilitates proper loading of either the single-use or the dual-use disposable components of the feeding sets into the enteral pump system and, as previously discussed above, enables the control, timing of activation, timing of deactivation, and/or speed of operation of the sensors, pinch valve, and rotary pump.

Embodiments of the present specification provide messages and controls to facilitate properly loading either single-use (Feed only) or dual-use (Feed and Flush) feeding sets onto an enteral device. The loading sequence is also described in context of FIG. 12. In some embodiments, proper loading involves securely engaging connectors in the designated pump seating areas; correctly routing tubing through the pinch rotor channels to insure proper flow control; routing tubing in sensor areas for proper sensing of tubing and liquid presence; routing the tubing around the pump rotor to ensure no free flow is possible and that pumping will move fluid properly; and ensuring that no occlusions occur due to connector placement or tubing routing.

In some embodiments, the loading process includes the identification of the feed set type either by operator input or by the sensors placed within the enteral device. At the completion of loading, the control system shall identify any free flow hazard (improper loading) and notify the operator with a Free Flow alarm.

Embodiments of the present specification provide messages and controls to fill the loaded feed set tubing with available flush and feed solutions provided that the feeding set has been installed prior to feeding. Alternatively, messages and controls to fill the loaded feed set tubing with available flush and feed solutions are provided during the feeding operation when feeding is interrupted by a feeding set change.

Embodiments of a pump control in accordance with the present specification provide a sequence of messages and controls to enter all required parameters for feeding into the pump settings. In some embodiments, the control sequence performs a few checks on entered settings. The checks may include, but are not limited to, verifying that inputs do not exceed the specification range for the setting; verifying that the settings match the feed set installed, verifying that all appropriate settings are entered; for feeding, verifying the feeding volume, and the feeding rate; and for feeding and flushing (dual-use), verifying feeding volume, feeding rate, flush volume, and flush interval. In addition, the pump controller may ensure that a complete set of settings is entered by clearing old settings, if any, and raising an alarm if more than a pre-defined period of time elapses in any part of the setting sequence. In one embodiment, the pre-defined period of time is 2.5 minutes. In some embodiments, the operator is offered an option of keeping the existing settings instead of entering new settings to the pump. Before offering the "keep settings" option, the controller will verify that the settings in the pump are complete and that each setting is within bounds for its function.

Embodiments of a pump control in accordance with the present specification provide a sequence of messages and controls to run the pump according to the prevailing settings. In some embodiments, the control sequence performs a few checks for operation. Embodiments of the checks that are performed include, but are not limited to, verifying that the correct feed set is installed; verifying that the feed set tubing remains in place to prevent free flow; verifying that there are no occlusions to flow; and verifying that the feed/flush bags are not empty. In embodiments, a visual feedback is provided to the operator about the function.

Embodiments of a pump control in accordance with the present specification provide a sequence of messages and controls to stop the pump either temporarily or until further operator action. In one embodiment, this mode is termed as 'Hold' mode. The 'Hold' mode may be implemented to allow alarm mute and pumping hold during operator correction of alarm conditions including occlusion clearance and bag refill. A 'Hold' of more than a pre-defined period of time, such as for example 2.5 minutes, may cause an audible alarm. Resumption from a hold condition will proceed with checks from the run procedure described above.

In some embodiments, a 'Halt' mode may be commanded by the operator through a front panel operation. The 'Halt' mode may require either prolonged application of a control or by a sequence of two controls to confirm that such a mode has been enabled. The 'Halt' condition may stop pumping and requires all checks for the run procedure to resume functioning.

Embodiments of a pump control in accordance with the present specification provide a sequence of messages and controls to set date and time used by the pump controller for logging events and to adjust volume of the alarms.

Embodiments of the pump control in accordance with the present specification maintains a history of daily feeding doses delivered in a pre-defined historical period. In one embodiment, history of daily feeding doses delivered in the past 72 hours is maintained. In embodiments, the history file can be reset to erase all records. The pump controller may provide a sequence of messages and controls to view the history records and to erase all history records.

After proper installation of a feed set, priming of the feed set tubing, and initiation of a feeding, the pinch rotor moves to select feeding solution and the pump rotor moves intermittently as dictated by a selected feed rate. The user interface displays an amount of volume delivered with numbers or quantity that increments to show how much formula has been delivered. During flush operations, the pump rotor turns intermittently. The amount of volume delivered increments to show how much water has been delivered. Once the feeding cycle finishes, such as when a daily dose has been reached, a final flush clears the lines to prevent feeding formula from clogging the lines.

After proper installation of a feed set, priming of the feed set tubing, and initiation of a feeding, or feed and flush program, the pump may sense the absence of fluid in the feed tubing or flush tubing (if installed) above the pump rotor, pause pumping, and generate an alarm if the sensed signal persists for a predefined period of time, such as for 5 seconds. The alarm shall indicate lack of flow and may not diagnose bag empty or upstream occlusion. In such a scenario, restarting the pump may initiate a new check cycle and may re-sense the condition if it has not been rectified.

After proper installation of a feed set, priming of the feed set tubing, and initiation of a feeding or feed and flush program, the pump may sense occlusion in the tubing downstream from the rotor and generate an 'Occlusion Alarm'. In some embodiments, the alarm may be muted for a pre-defined period of time, such as for example 2.5 minutes. Expiration of the mute period or an operator signal may cause the occlusion check cycle to be repeated. If the occlusion is still present, the alarm will resound. Holding or halting the pump may clear the alarm. The occlusion test may repeat when the pump is restarted and periodically during operation.

When the pump is operating on battery alone with no AC connection, the battery output may be monitored. Battery depletion beyond the power needed to operate the pump may cause an alarm to be generated and result in a message indicating low battery, to be displayed. Connecting the AC power or replacing the battery may cancel the alarm.

After the pump is activated, tubing must be present between the pinch rotor and the Y-shaped connector (for dual-use) or half-Y-shaped connector (for single-use) and downstream of the pump rotor, or a Free Flow Alarm may be generated. The audible alarm and accompanying message indicates that the feed set was not properly installed or has become dislodged. In the case where the controller detects the alarm and that the feed set was not properly installed or has become dislodged, pump operation is held. The alarm may be muted for a pre-defined period of time, such as for example 2.5 minutes, while the condition is corrected. After the pre-defined time period, the alarm may resound if the feed set is not properly installed at that time. After correcting the condition, the operator may resume operation of the pump and cancel the alarm.

Any failure of the pump or components to respond to a commanded action (programmed or manually entered) may result in an audible alarm with display of an appropriate message.

At any time during feeding or flush operation, the pump can be paused by simply pressing a 'pause' button. On selecting the option to 'pause', the pump rotor stops. If feeding is not resumed within a specified amount of time, an alarm may sound. In some embodiments, this time is of about 2.5 minutes. While the pump is paused, the feeding setup may be edited and the history of feeding sessions may be reviewed.

Some embodiments of the present specification may incorporate the following parameters for operation of the enteral device in accordance with the present specification.

Feeding volume range: The pump may deliver a daily (24 hr.) dose of 50 ml. to 3000 ml. of feeding solution per the programmed setting.

Feeding volume resolution: The daily feeding dose shall have a setting resolution of approximately 1 ml.

Feeding volume accuracy: The accuracy of the feeding volume delivered to a patient may be +/−10% measured on a 300 ml volume delivered in a 1 hour period.

Feeding rate range: The feeding rate may be programmable from 10 to 300 ml/hr.

Feeding rate resolution: The feeding rate may be programmable with 1 ml/hr. resolution.

Flush volume range: The flush volume delivered during any flush cycle may be set from 10 ml to 500 ml.

Flush volume resolution: The flush volume may be programmable with 1 ml resolution.

Flush volume accuracy: The pump may deliver the flush volume +/−10% as measured at 300 ml.

Minimum alarm volume: The alarm signal may have a minimum volume of 50 dB when measure from 10 feet away from the pump.

Flush interval: Flush operations interrupt feeding with a cycle that delivers the programmed flush volume at the programmed flush rate periodically throughout the feeding cycle (until stopped or feeding daily dose is delivered). The interval between flush cycles may be programmable from 1-24 hours. A single flush of 50 ml may be delivered at the end of the feeding cycle.

Flush interval resolution: The flush interval may be set in 1 hour increments.

Battery life: A fully charged battery may operate the pump for 8 hours at a continuous feed rate of 300 ml/hr. without connection of the AC power supply.

Battery recharge: When connected to AC power a battery discharged to the alarm limit may recharge to >90% capacity within 12 hours.

Operating voltage: The AC-DC power supply may provide adequate pump power when the mains voltage is between 100 and 240 VAC.

Operating frequency: The AC-DC power supply may provide adequate pump power when the mains frequency is between 48 and 62 Hz.

Display size: The primary text displayed on the screen may be a minimum of 0.6 inches in height. Primary text includes the setting number or value being adjusted (Dose, Rate, Time). Primary text also includes all alarm or error messages. Secondary text including labels may be a minimum of 0.3 inches in height.

Display contrast: The display may have a minimum contrast of 4:1 in brightness of the characters to the background when active.

Unit lifetime: The projected service life of the pump (not including feeding sets or the battery) may be 10 years or greater.

In some embodiments in accordance with the present specification, the system is further designed to prevent free-flow. Free flow may be defined as any flow of fluids when the pump rotor is not turning. Therefore, the flow of either feeding solution or water to the patient is prevented when a feeding set is improperly installed.

In some embodiments in accordance with the present specification, the pump is designed to retain the previous programming including, time, date, feeding dose, feeding rate, flush volume, flush rate, and flush interval when powered or unpowered until manually reset by the operator.

In some embodiments in accordance with the present specification, the pump battery is easily replaceable, such as by using ordinary household tools.

In some embodiments in accordance with the present specification, the system does not require calibration.

In some embodiments in accordance with the present specification, the power cord used with the device is not removable. Additionally, a cord storage space is configured for winding the cord with the body of the enteral device.

In some embodiments in accordance with the present specification, the pole clamp integrated with the enteral device is non-detachable, and which enables attaching the pump to a standard IV pole.

In some embodiments in accordance with the present specification, a display integrated within the enteral device is viewed from a vertical angle ranging from −30 degrees to +30 degrees. Controls for the display may be operated from an angle of approach of + or −30 degrees from vertical.

In some embodiments in accordance with the present specification, the enteral device is configured with depressions in the rear of the pump enclosure along either side and along the back, to serve as handles while mounting or programming the pump.

In some embodiments in accordance with the present specification, the enteral device is configured to incorporate a method for reloading software or replacing existing software with revised software under control of a qualified maintenance technician.

In some embodiments in accordance with the present specification, the enteral device is configured to mute any alarm for a pre-defined period of time.

User Interface (UI)

In one embodiment, the UI of the enteral pump system in accordance with the present specification, uses a graphical monochrome display in a menu driven interface. In another embodiment, the UI of the enteral pump system in accordance with the present specification, uses an LCD character display and case labelled LEDs for the interface. In embodiments, UI of the present specification has buttons for input from a user. In embodiments, the graphical UI utilizes low power, has a high contrast, has low or no viewing angle restrictions, and is a completely graphical display. In an embodiment, E paper, also known as E Ink, is used for the graphical display. E Paper is a low power device. Also, it only draws power when it is updated and can hold an image indefinitely without power. It does not utilize backlighting and does not require power to display an image. Because of this, it has battery consumption advantage. In addition, a logo or other informative images can be displayed when the system is off or in a power saving standby mode. Additionally, the E Paper display has a high contrast image. E Paper can be read in sunlight. Further, E Paper has no viewing angle restrictions. The E Paper display is also complete graphical. E Paper can display many different and large fonts. The larger fonts for portions of the UI can be visible at a greater distance than other types of display. This allows for quick status checks while the device is in operation. Bold characters can be used and non-alphanumeric symbols can be displayed enhancing the information displayed. In embodiments using E paper, diagram images may also be rendered on the interface.

Figure 13A:
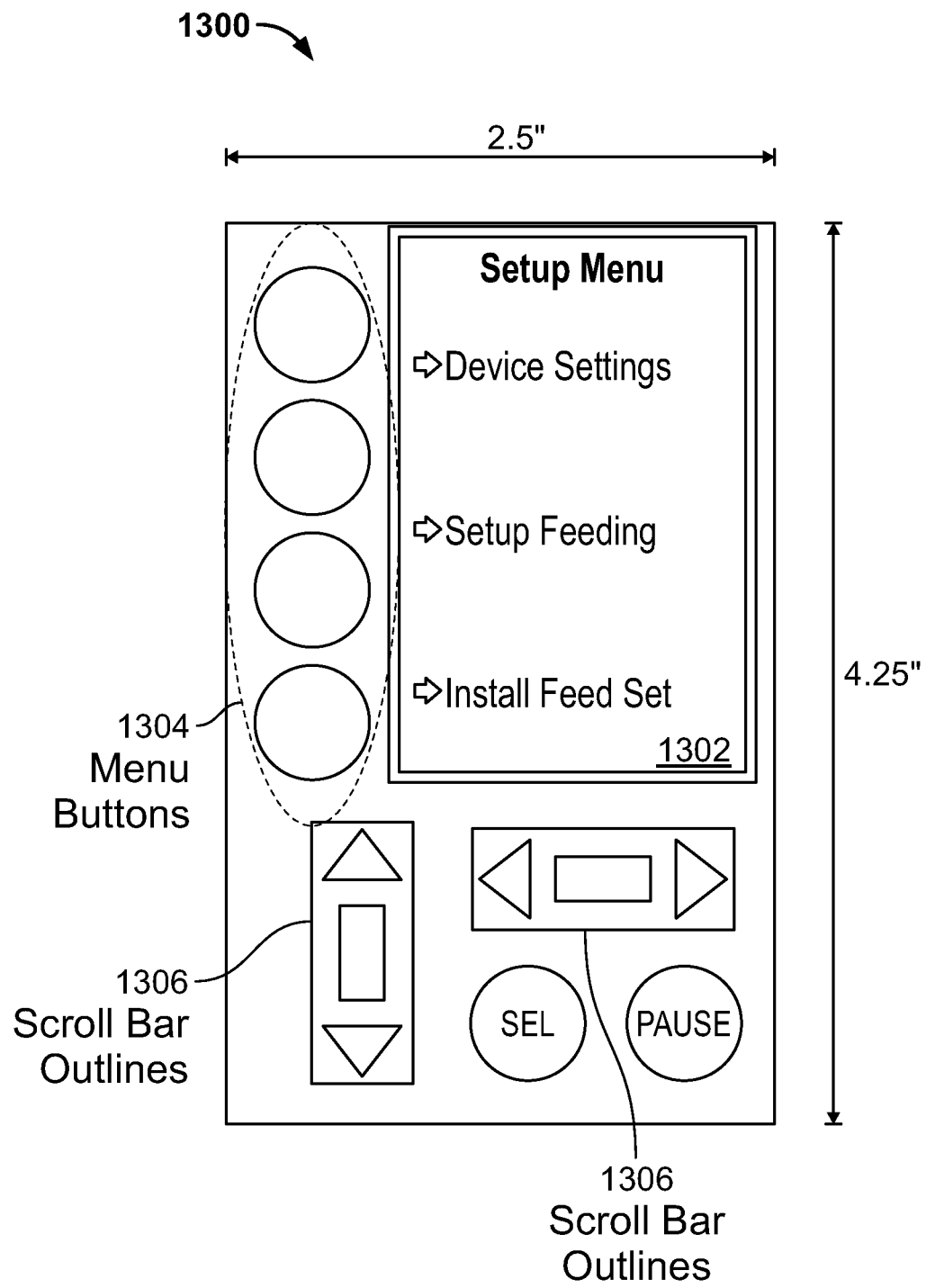
FIG. 13A illustrates an exemplary User Interface (UI) displaying an initial setup menu, in accordance with some embodiments of the present specification.

FIG. 13A illustrates an exemplary UI 1300 displaying an initial setup menu, in accordance with some embodiments of the present specification. In an embodiment, menu is displayed on a display 1302 immediately after powering up or starting the enteral pump system in accordance with the present specification. In one embodiment, UI 1300 has a length of approximately 4.25 inches, and a width of 2.5 inches. In embodiments, UI 1300 has a graphical display 1302 with menu choices for the user at start-up. A vertical array of menu buttons 1304 is on the left of display 1302. In some embodiments, the menu choices on display 1302 are positioned to be associated with a corresponding button in the array 1304. In some embodiments, below the buttons array 1304 and display 1302, are at least one or more scroll bars where the user can scroll left to right horizontally or up and down vertically by swiping a finger across the scroll area. Scroll bar outlines 1306 show an exemplary electronic feature supporting these scroll bars. In one embodiment, a silk screen is provided for scrolling purposes.

In addition, in some embodiments, two more buttons are configured on the UI 1300. A 'select' button 1308 is used to select and execute a menu option on which the user may have reached through scrolling. A 'pause' button 1310 may be of red colour, or any other contrasting colour such as a colour close to red. Button 1310 may be used to pause the functioning of the enteral pump system in accordance with embodiments of the present specification.

In some embodiments, all the buttons and scroll bar features of UI 1300 are achieved by case silk-screening. In some embodiments, the buttons and the scroll bars are facilitated by CapSense® circuitry, achieved by special etch geometry on a circuit board (FR4) under a plastic shield (maybe the plastic case). The user may merely touch an area of the shield and the button press is determined by the change in capacitance due to the presence of the user's figure.

Figure 13B:
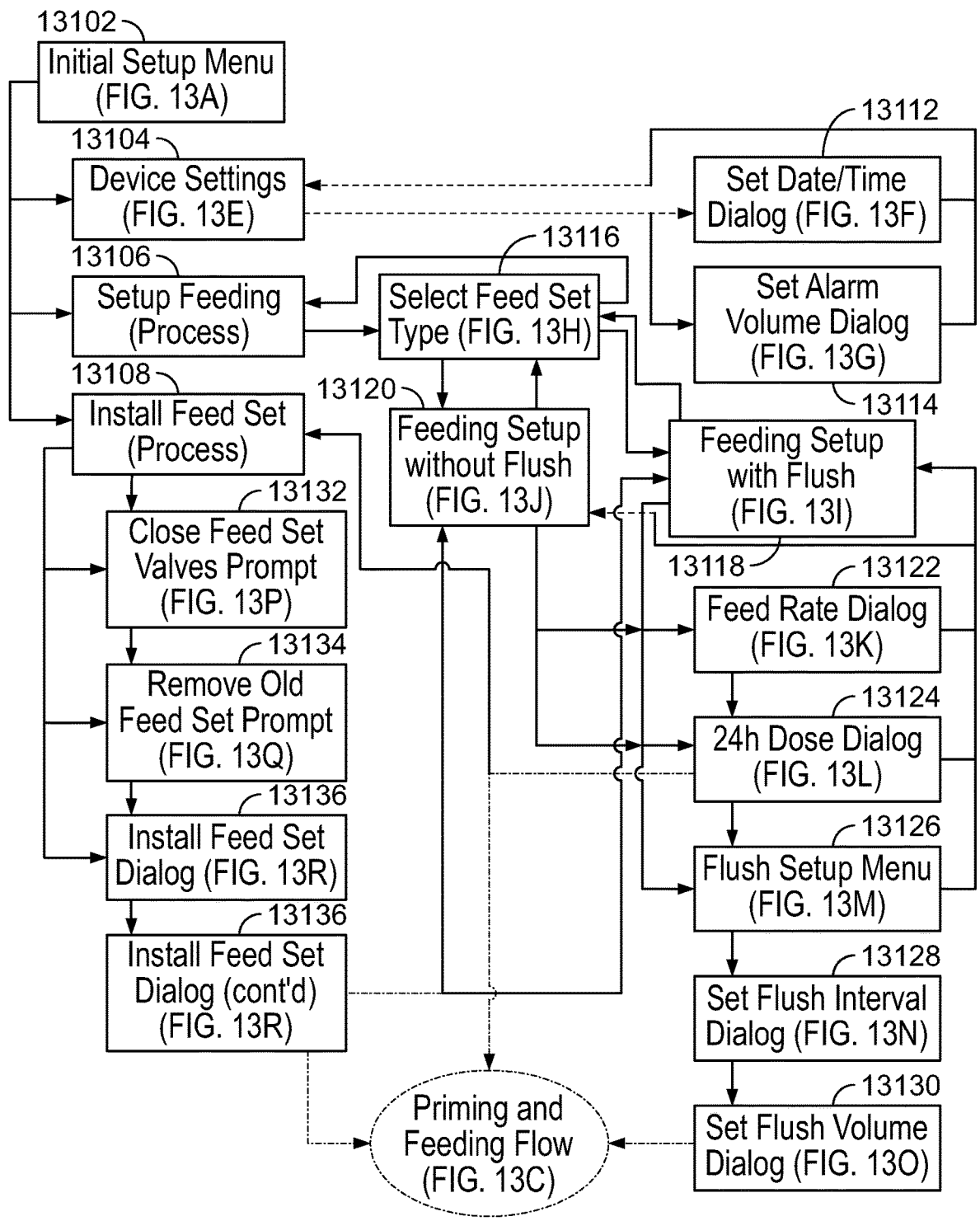
FIG. 13B illustrates an exemplary flow of communication between various menus, dialogs, and prompts displayed by the UI of FIG. 13A, in accordance with an embodiment of the present specification.

FIG. 13B illustrates an exemplary flow of communication between various menus, dialogs, and prompts displayed by UI 1300, in accordance with an embodiment of the present specification. The various UI scenarios stated in FIG. 13B are now subsequently described in detail and with reference to corresponding figures illustrating their exemplary display seen on UI 1300.

Figure 13C:
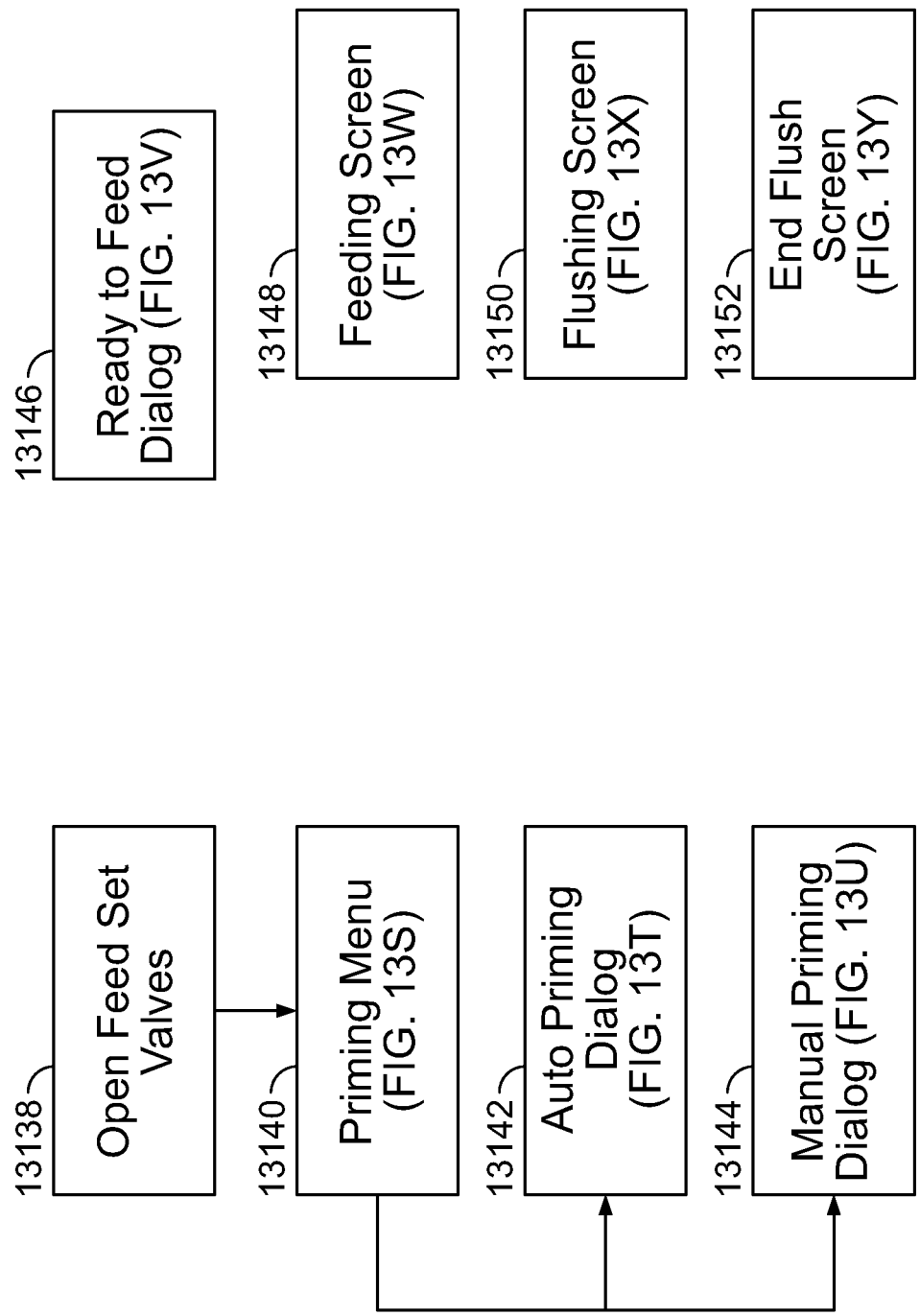
FIG. 13C illustrates an exemplary flow of communication between various menus, dialogs and prompts displayed by the UI of FIG. 13A for priming and while performing the feeding or feeding and flushing functions, in accordance with an embodiment of the present specification.

FIG. 13C illustrates an exemplary flow of communication between various menus, dialogs and prompts displayed by the UI 1300 for priming and while performing the feeding or feeding and flushing functions, in accordance with an embodiment of the present specification. The various UI scenarios stated in FIG. 13C are subsequently described in detail and with reference to corresponding figures illustrating their exemplary display seen on UI 1300.

At 13102, FIG. 13A illustrates an exemplary UI 1300 displaying an initial setup menu, in accordance with some embodiments of the present specification. From 13102, a user may navigate to 13104 (FIG. 13D), 13106, or 13108.

Figure 13E:
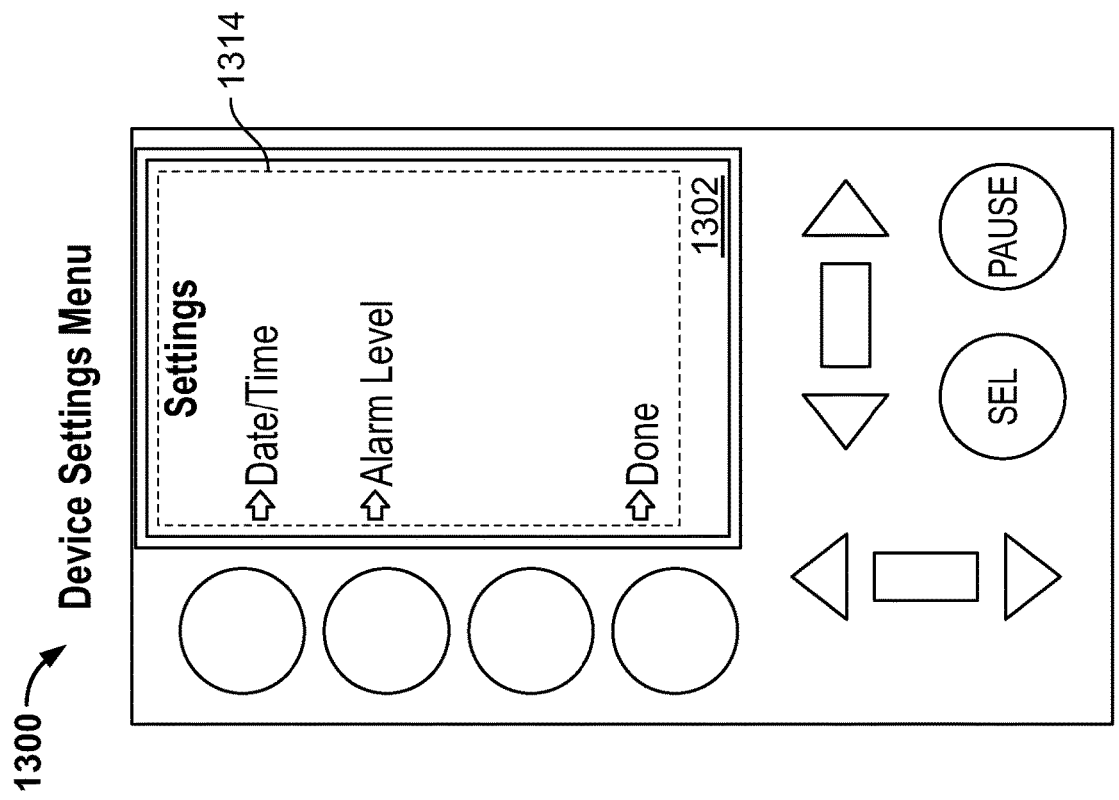
FIG. 13E illustrates a device settings menu within the display in accordance with an embodiment of the present specification.
Figure 13D:
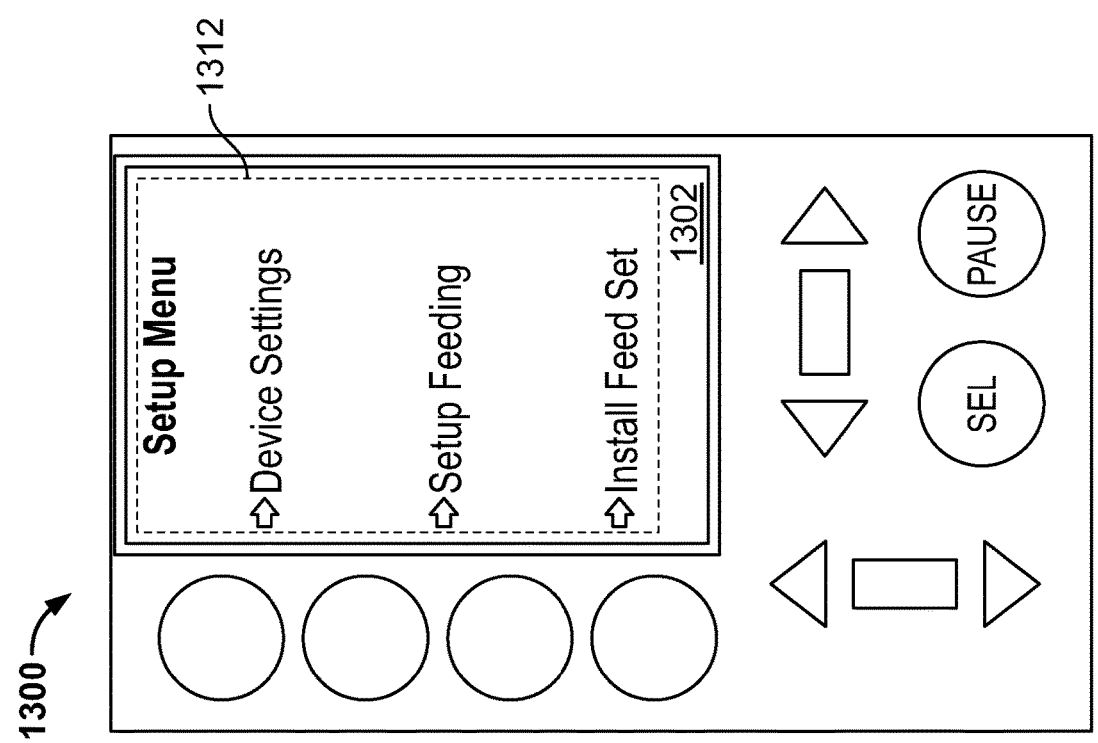
FIG. 13D illustrates an initial setup menu within the display in accordance with an embodiment of the present specification.

Referring to FIG. 13D, an initial setup menu 1313 is illustrated within display 1302 in accordance with an embodiment of the present specification. In some embodiments, there are multiple uses for the Initial Setup Menu 1312. The first is to enter the 'Device Settings Menu', at 13104. The second is for 'Setup Feeding' quantities and feature, at 13106. The third, at 13108, allows the user to bypass device settings and feeding programming to be performed later. The user can jump to the 'Install Feed Set' dialog.

Device Settings Menu 13104

This menu may allow the user to specify the date/time and other device options of the Enteral Feeding Pump. The feature may be expanded as new options are defined.

Setup Feeding 13106

The Setup Feeding dialog may allow the user to specify rate and total dose quantities, in addition to other parameters of the patient feeding. This dialog may also allow the user to choose the feed set type.

Install Feed Set Dialog 13108

The install Feed Set dialog may provide an overview of the installation process. It is intended to provide a quick check list for the user. If feed set is already present in the mechanism, it is assumed to be from a prior use. In the case, the mechanism may make it difficult to remove the feed set, a dialog for the removal is provided.

If no feed set is present, the normal Install Feed Set dialog is entered.

At 13104, referring to FIG. 13E, a device settings menu 1314 is illustrated within display 1302 in accordance with an embodiment of the present specification. In some embodiments, a first use case for menu 1314 is to adjust the real-time clock's date and time. The date and time may be used for the time stamp of a History Log maintained by the enteral pump system. A second use case may be to enable the user to specify an alarm volume level. Pressing the menu buttons to the left of the display will initiate the corresponding dialog. Once the action of pressing is done, menu 1314 option of 'Done' may return the display 1302 to the Setup Menu 1312.

Figure 13G:
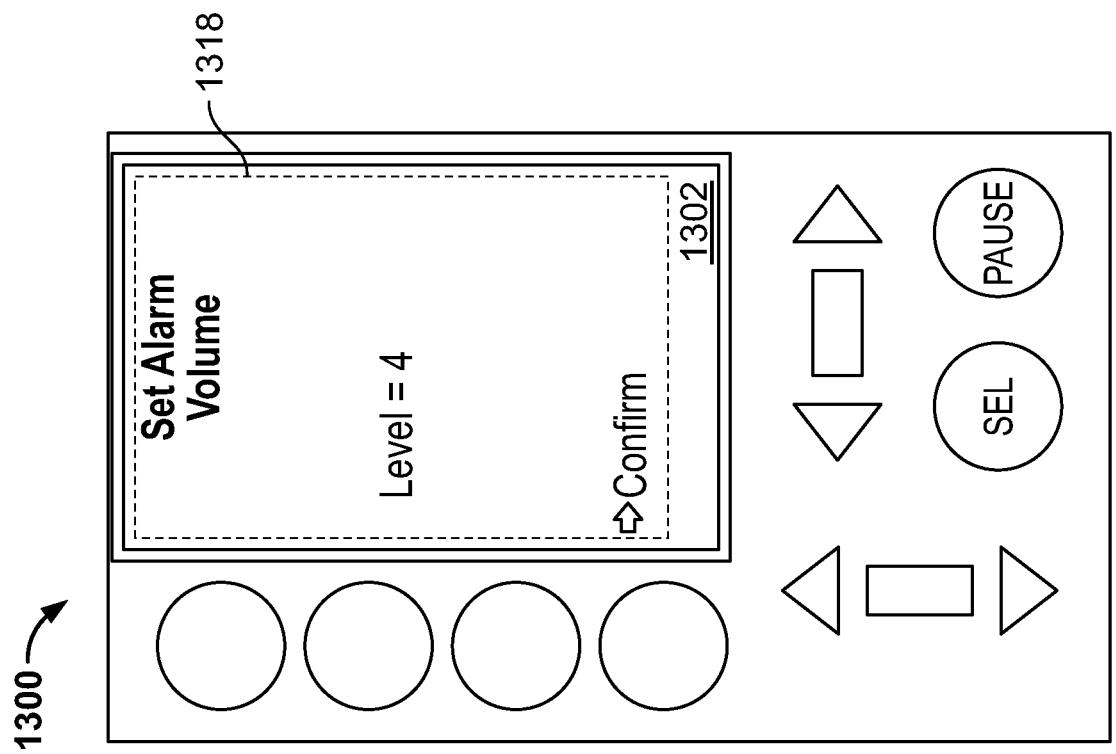
FIG. 13G illustrates an alarm volume setup menu within the display in accordance with an embodiment of the present specification.
Figure 13F:
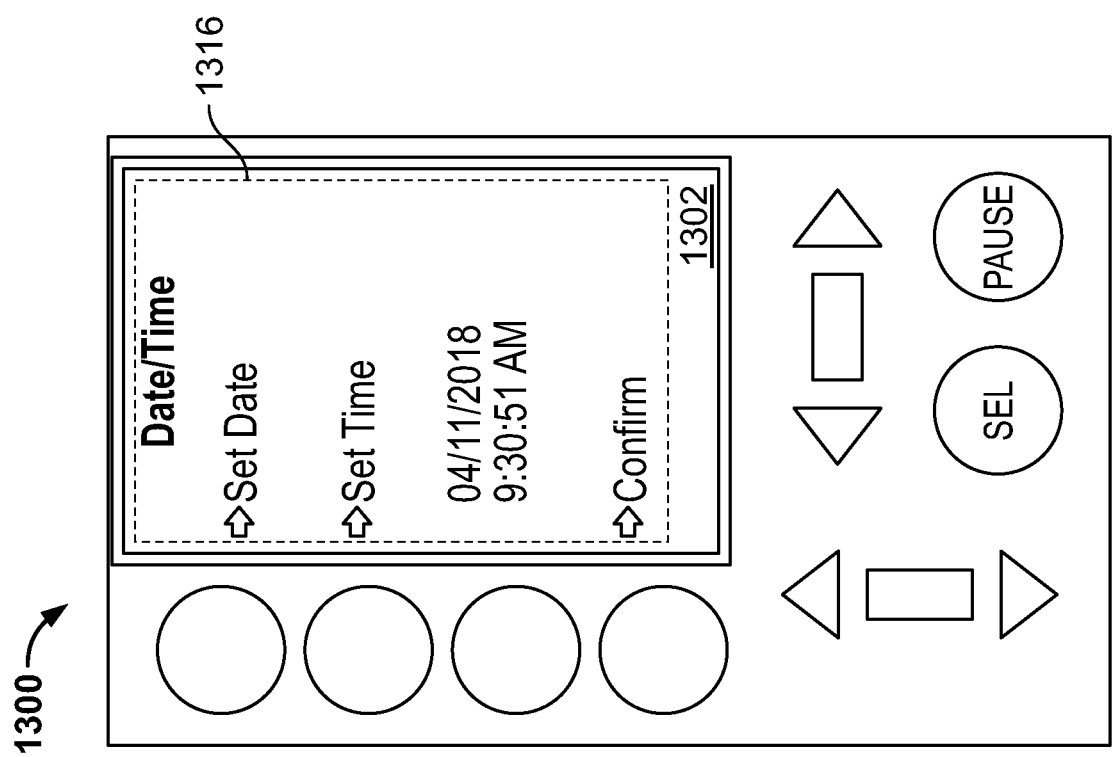
FIG. 13F illustrates a date and time setup menu within the display in accordance with an embodiment of the present specification.

At 13112, referring to FIG. 13F, a date and time setup menu 1316 is illustrated within display 1302 in accordance with an embodiment of the present specification. Pressing the menu buttons to the left of the display 1302 will initiate the corresponding dialog.

Set Date Dialog

The user may adjust the month digit(s), each day digit and the years digits using the up/down scroll bar. The month may be chosen in the range 01 to 12 and may roll up or down depending on the scroll direction. Each day and year digit can be chosen and adjusted separately. The ranges for each may conform to the ranges of the standard calendar. These digits may also roll in value depending on the up/down scroll direction. The user can select which digit to adjust by using the left/right scroll bar. The display may indicate which digit is adjusted by blinking the active digit. Moving off the digit to the next implies that the previously active digit value has been selected. Pressing the "SEL" button may also enable the user to finish the adjustment of a digit and the next to the right digit will become the active digit. If the right most year digit was active, the month value will then be active (i.e. wrap around). When using the left/right scroll bar the active digit may also wrap around depending on the direction.

Selecting "Set Time" may complete the date adjustment function.

Set Time Dialog

When the user enters the Set Time dialog the real-time clock may stop and the time display may stop updating. The clock may not restart while in the dialog unless the Set Date mode is entered. The user may adjust the hour digits, the minute digits and the second digit by using the up/down scroll bar. In addition, the user may set the AM/PM indication also using the up/down scroll bar. In one embodiment, the range for the digits of hours is 1 to 12. In one embodiment, the range of the leftmost digits for minutes and seconds is 0 to 5. In one embodiment, the range of the rightmost digit for minutes and seconds is 0 to 9. The digits may roll in value depending on the up/down scroll direction. The user may select which digit to adjust by using the left/right scroll bar. The display may indicate which digit is adjusted by blinking the active digit. Moving off the digit to the next implies that the previously active digit value has been selected. Like the digits, the AM/PM indicator may be selected to adjust.

Pressing the "SEL" button may also enable the user to finish the adjustment of a digit and the next to the right digit may become the active digit. If the right most seconds digit was active, the hour value will then be active (i.e. wrap around). When using the left/right scroll bar the active digit will also wrap around depending on the direction.

Selecting "Set Time" may complete the time adjustment function.

Pressing "Confirm"

Pressing "Confirm" may complete both date and time adjustment functions. The display may return to the previous Settings Menu 1314. When done the real-time clock may restart at the adjusted setting.

At 13114, referring to FIG. 13G, an alarm volume setup menu 1318 is illustrated within display 1302 in accordance with an embodiment of the present specification. This dialog may enable the user to set a desired alarm tone volume level using the up/down scroll bar. The alarm volume level setting may be in the range of 1 to 5. In an embodiment, the value selected is displayed as a single digit. By pressing "Confirm", the user may confirm the volume level that is desired. Subsequently, display 1302 may return to the previous Settings Menu 1314.

Figures 13H, 13I:
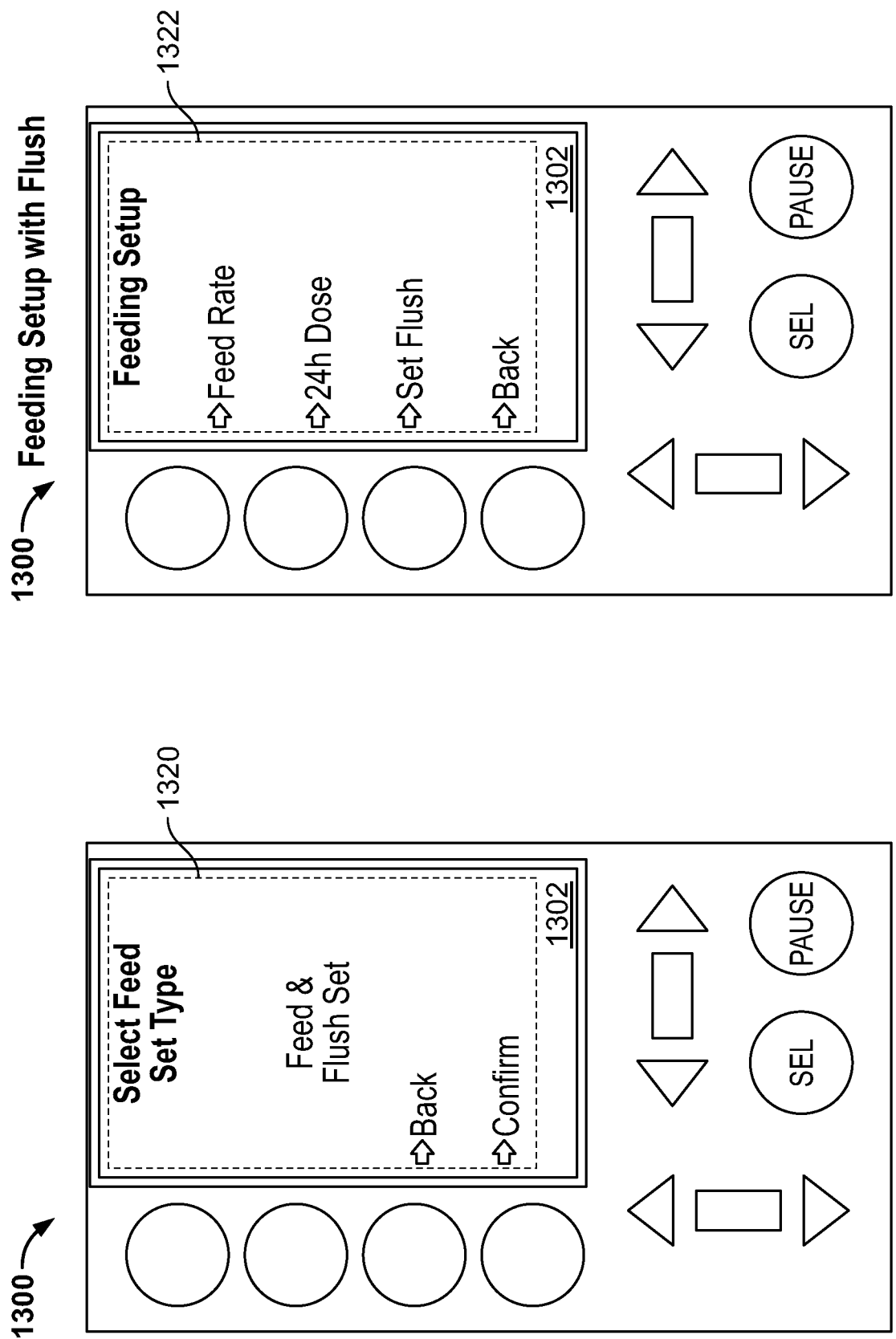
FIG. 13H illustrates a feed type selection setup menu within the display in accordance with an embodiment of the present specification.
FIG. 13I illustrates a feeding setup with flush menu within the display in accordance with an embodiment of the present specification.

At 13116, referring to FIG. 13H, feed type selection setup menu 1320 is illustrated within display 1302 in accordance with an embodiment of the present specification. When the user invokes the 'Setup Feeding' from previous menu 1312 or 'Change Feeding' (after the initial setup), the 'Select Feed Set' dialog is invoked. The user specifies the type of feed set from two choices. Initially the dialog may display one of two feed set types—"Feed Only Set" or "Feed & Flush Set". The user may change the selection using the up/down scroll bar or the "SEL" button. The user may confirm the feed set type selected by pressing "Confirm". Pressing "Back" may display the previous Setup Menu. By pressing "Confirm", the user may confirm the feed set type desired. Depending on the type selected, the next screen of the feeding setup dialog will be displayed.

At 13118, referring to FIG. 13I, a feeding setup with flush menu 1322 is illustrated within display 1302 in accordance with an embodiment of the present specification. In some embodiments, there are three use cases for the 'Feeding Setup with Flush' Menu 1322. The user may specify a feed rate, the total volume in a 24 hour period (Dose), and set the flush protocol. Pressing the corresponding menu button will invoke the appropriate dialog for each. Pressing "Back" may display the previous Feeding Setup menu 1320.

Figure 13K:
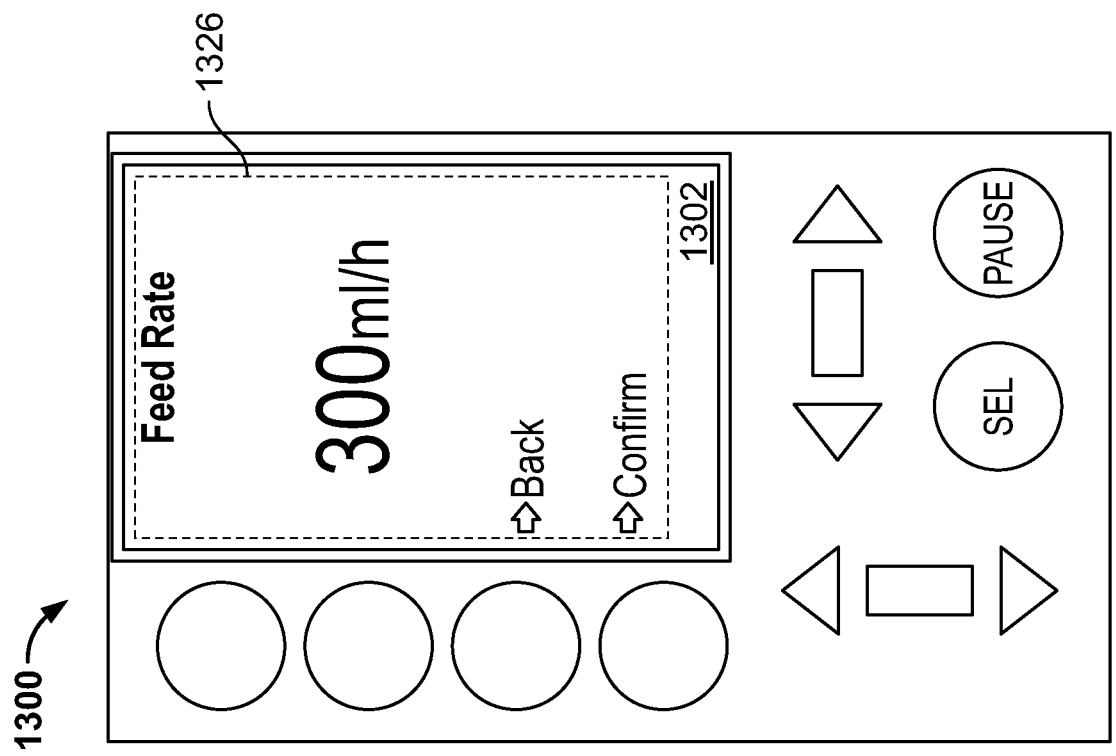
FIG. 13K illustrates a feed rate menu within the display in accordance with an embodiment of the present specification.
Figure 13J:
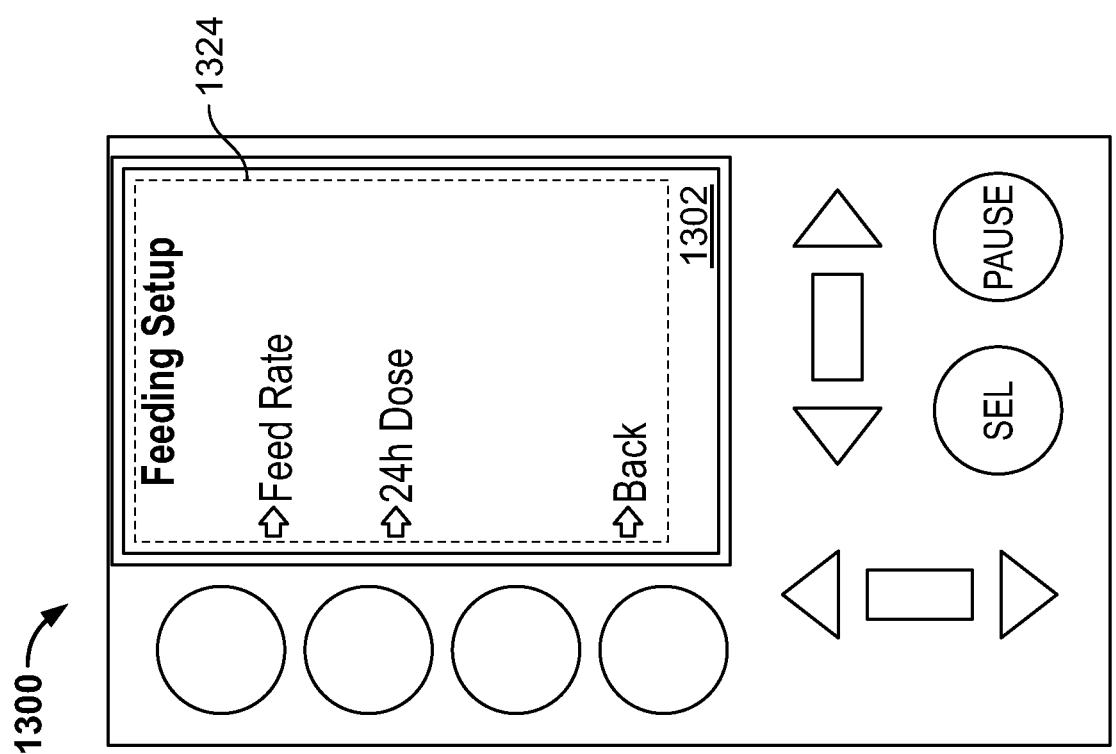
FIG. 13J illustrates a feeding setup without flush menu within the display in accordance with an embodiment of the present specification.

At 13120, referring to FIG. 13J, a feeding setup without flush menu 1324 is illustrated within display 1302 in accordance with an embodiment of the present specification. In some embodiments, there are two use cases for Feeding Setup without Flush Menu 1324. The user may specify a Feed Rate and a total volume in a 24 hour period (Dose). Pressing the corresponding menu button may invoke the appropriate dialog for each. Pressing "Back" may display the previous Feeding Setup menu 1320.

At 13122, referring to FIG. 13K, a feed rate menu 1326 is illustrated within display 1302 in accordance with an embodiment of the present specification. In some embodiments, the user may specify the desired feed rate. In an embodiment, the user specifies the feed rate in the range of 10 ml/h to 300 ml/h in units of 1 ml/h. Initially, leading zeros may be displayed and will replace leading spaces to show three digits of feed rate to adjust. The user may adjust each digit of the feed rate using the up/down scroll bar. Each digit may be set in the range of 0 to 9 except for the leftmost digit, which can be set in the range of 0 to 3. The digits may roll up or down depending if scrolling up or down. The adjusted digits may remain in the valid range and will automatically adjust to the maximum or minimum when those limits are exceeded.

The user may select which digit to adjust by using the left/right scroll bar. The display 1302 may indicate which digit is adjusted by blinking the active digit. Moving off the digit to the next implies that the previously active digit value has been selected. Pressing the "SEL" button may also enable the user to finish the adjustment of a digit and the next to the right digit will become the active digit. If the right most digit was active, the leftmost digit will become active (i.e. wrap around). When using the left/right scroll bar the active digit may also wrap around depending on the direction. Pressing "Back" may return display 1302 to the Feed Setup menu 1322 or 1324. Pressing "Confirm" may confirm the feed rate and the display will invoke the next setup Feeding dialog screen.

Figure 13M:
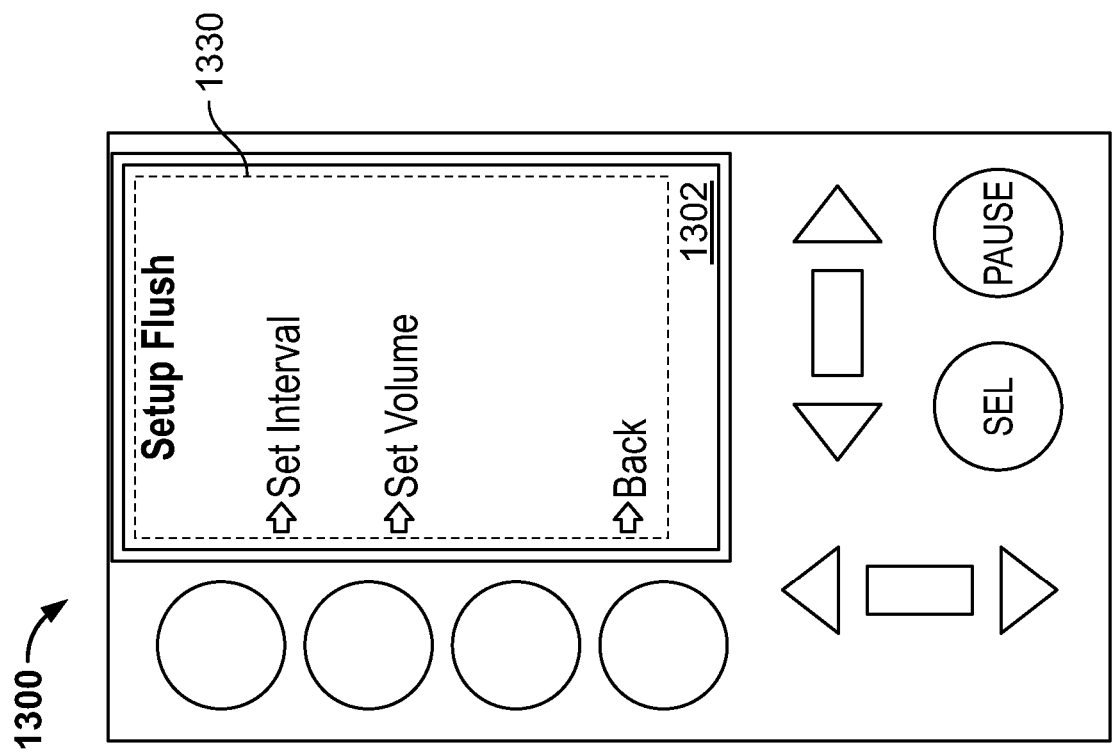
FIG. 13M illustrates a flush setup menu within the display in accordance with an embodiment of the present specification.
Figure 13L:
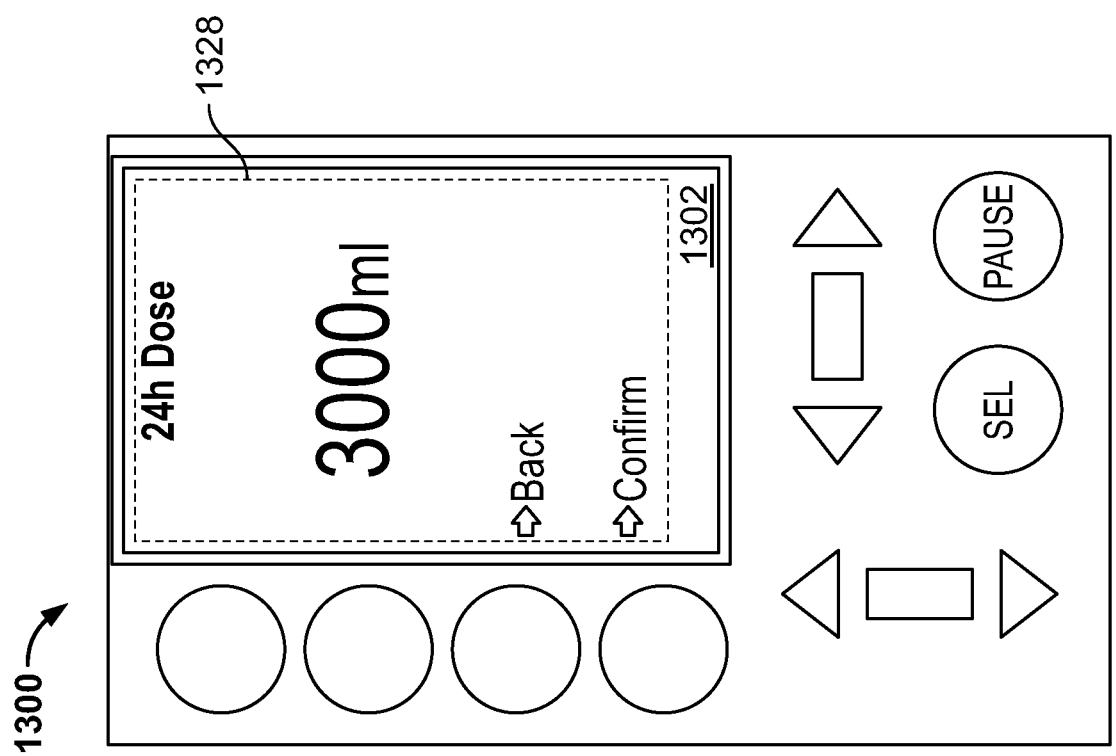
FIG. 13L illustrates a 24 hours dose menu within the display in accordance with an embodiment of the present specification.

At 13124, referring to FIG. 13L, a 24 hours dose menu 1328 is illustrated within display 1302 in accordance with an embodiment of the present specification. In some embodiments, the user may specify the desired total volume dose in a 24 hour feeding. In an embodiment, the 24 h dose is specified in a range of 50 ml to 3000 ml in units of 1 ml/h. Initially, leading zeros are displayed and may replace leading spaces to show four digits of total volume to adjust. The user may adjust each digit of the 24 h dose using the up/down scroll bar. Each digit may be set in a range of 0 to 9 except for the leftmost digit, which may be set in the range of 0 to 3. The digits may roll up or down depending if scrolling up or down. The adjusted digits may remain in the valid range and will automatically adjust to the maximum or minimum when those limits are exceeded. The user may select which digit to adjust by using the left/right scroll bar. The display may indicate which digit is adjusted by blinking the active digit. Moving off the digit to the next implies that the previously active digit value has been selected. Pressing the "SEL" button may also enable the user to finish the adjustment of a digit and the next to the right digit will become the active digit. If the right most digit was active, the leftmost digit may become active (i.e. wrap around). When using the left/right scroll bar the active digit may also wrap around depending on the direction. Pressing "Back" returns display 1302 to Feed Setup menu 1322 or 1324, depending on the feed set type. Pressing "Confirm" confirms the feed rate and the display will invoke the next setup Feeding dialog screen, or if done with Feeding Setup for the feed set type display will go on to a Priming Menu.

At 13126, referring to FIG. 13M, a flush setup menu 1330 is illustrated within display 1302 in accordance with an embodiment of the present specification. Flush setup menu 1330 may enable the user to specify the interval of time that a flush will occur. It does this by invoking a Flush Interval dialog. It also enables the user to specify the flush volume at each interval. It does this by invoking an Interval Volume dialog. Pressing "Back" returns display 1302 to the Feed Setup menu 1322.

Figure 13O:
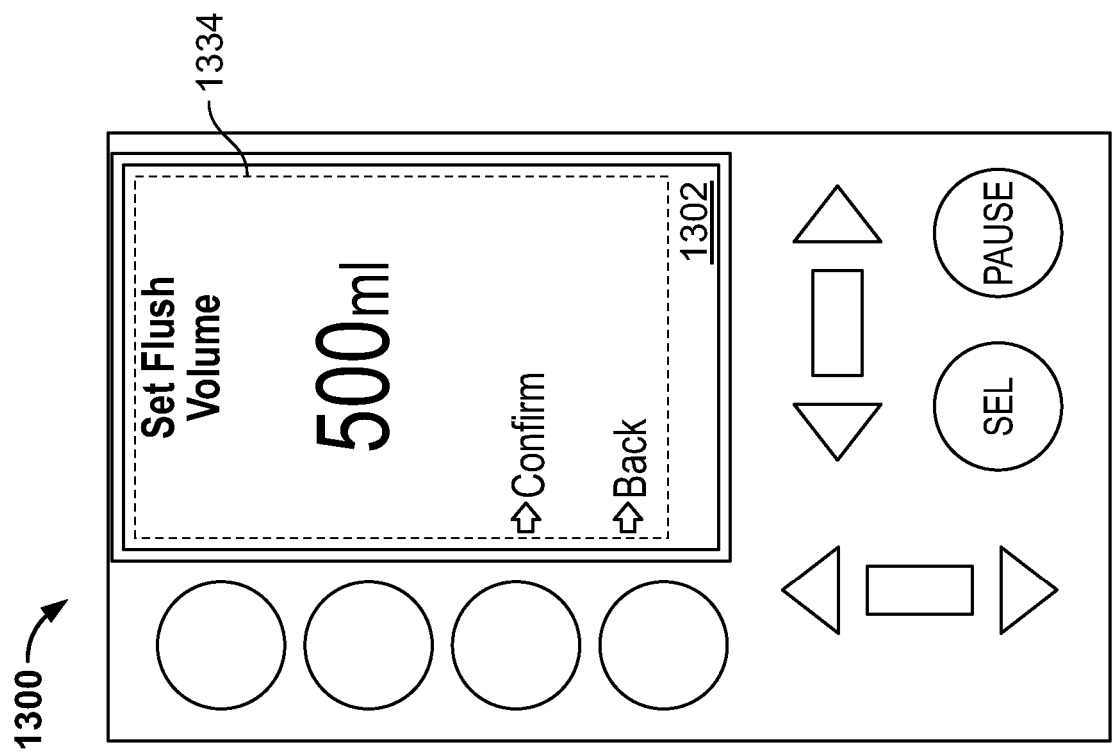
FIG. 13O illustrates a flush volume setup menu within the display in accordance with an embodiment of the present specification.
Figure 13N:
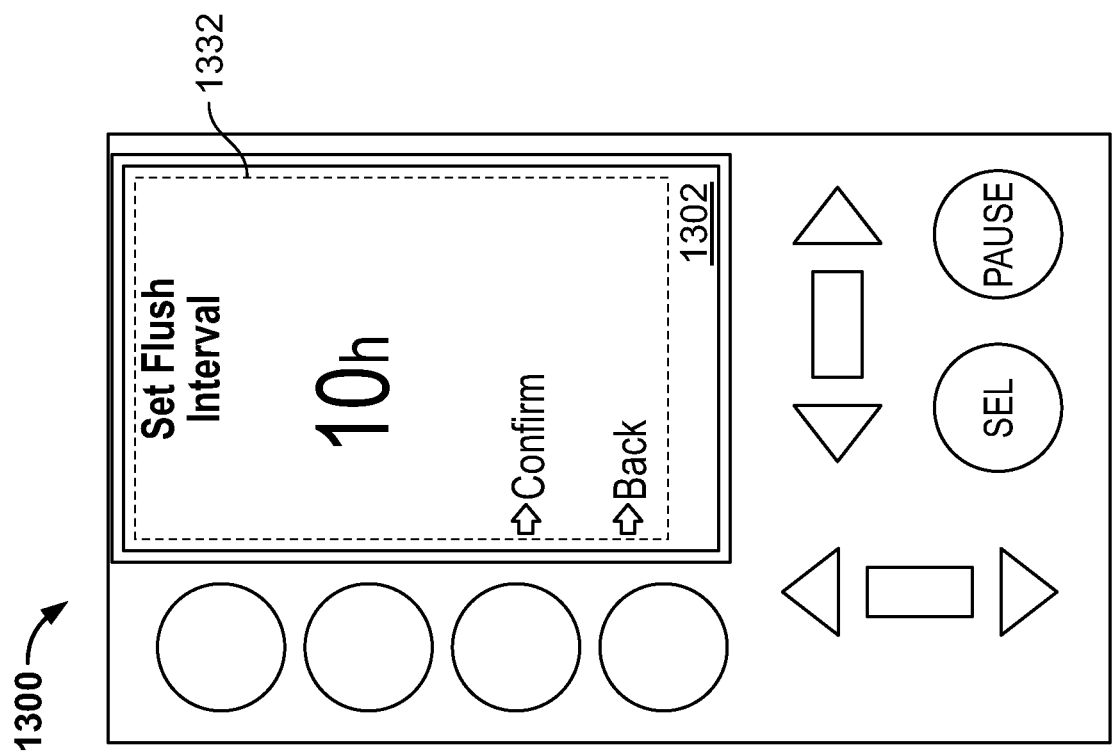
FIG. 13N illustrates a flush interval setup menu within the display in accordance with an embodiment of the present specification.

At 13128, referring to FIG. 13N, a flush interval setup menu 1332 is illustrated within display 1302 in accordance with an embodiment of the present specification. Menu 1332 may enable the user to specify the time interval between flushing. The feeding process is interrupted and flushing starts at the specified time interval. When the flush volume is achieved the feeding process restarts. In an embodiment, a range of the interval time is 1 to 24 hours in units of 1 hour. Initially, a leading zero may be displayed and will replace leading spaces to show two digits of time interval to adjust. The user may adjust each digit using the up/down scroll bar. Each digit may be set in the range of 0 to 9 except for the leftmost digit, which may be set in the range of 0 to 2. The digits may roll up or down depending on if scrolling up or down. The adjusted digits may remain in the valid range and will automatically adjust to the maximum or minimum when those limits are exceeded. The user may select which digit to adjust by using the left/right scroll bar. The display may indicate which digit is adjusted by blinking the active digit. Moving off the digit to the next implies that the previously active digit value has been selected. Pressing the "SEL" button may also allow the user to finish the adjustment of a digit and the next to the right digit will become the active digit. If the right most digit was active, the leftmost digit will become active (i.e. wrap around). When using the left/right scroll bar the active digit will also wrap around depending on the direction. A single flush of 50 ml may be delivered at the end of the feeding cycle, if the flush type feeding set is installed. Pressing "Confirm" confirms the interval specified. The Display will go on to the Set Flush Volume menu. Pressing "Back" will display the Flush Setup Menu 1330.

At 13130, referring to FIG. 13O, a flush volume setup menu 1334 is illustrated within display 1302 in accordance with an embodiment of the present specification. Flush volume setup menu 1334 may enable the user to specify a volume of flush at each flush interval. The feeding process in interrupted and flushing will start at the specified time interval. When the flush volume is achieved the feeding process restarts. In an embodiment, a range of flush volume is 10 ml to 500 ml in units of 1 ml. Initially, a leading zero may be displayed and will replace leading spaces to show three digits of volume to adjust. The user may adjust each digit using the up/down scroll bar. Each digit may be set in the range of 0 to 9 except for the leftmost digit, which may be set in the range of 0 to 5. The digits may roll up or down depending if scrolling up or down. The adjusted digits may remain in the valid range and will automatically adjust to the maximum or minimum when those limits are exceeded. The user may select which digit to adjust by using the left/right scroll bar. The display will indicate which digit is adjusted by blinking the active digit. Moving off the digit to the next implies that the previously active digit value has been selected. Pressing the "SEL" button may also allow the user to finish the adjustment of a digit and the next to the right digit will become the active digit. If the right most digit was active, the leftmost digit will become active (i.e. wrap around). When using the left/right scroll bar the active digit will also wrap around depending on the direction. Pressing "Confirm" confirms the flush volume specified. If the feeding setup is complete and the feed set is installed, the system may display the Priming Menu. If the system was pause during feeding, a Pause Feeding Menu may be displayed. If a new feed set is not installed, the display will show an Install Feed Set process. Pressing "Back" will display the Flush Setup Menu 1330.

Figures 13P, 13Q:
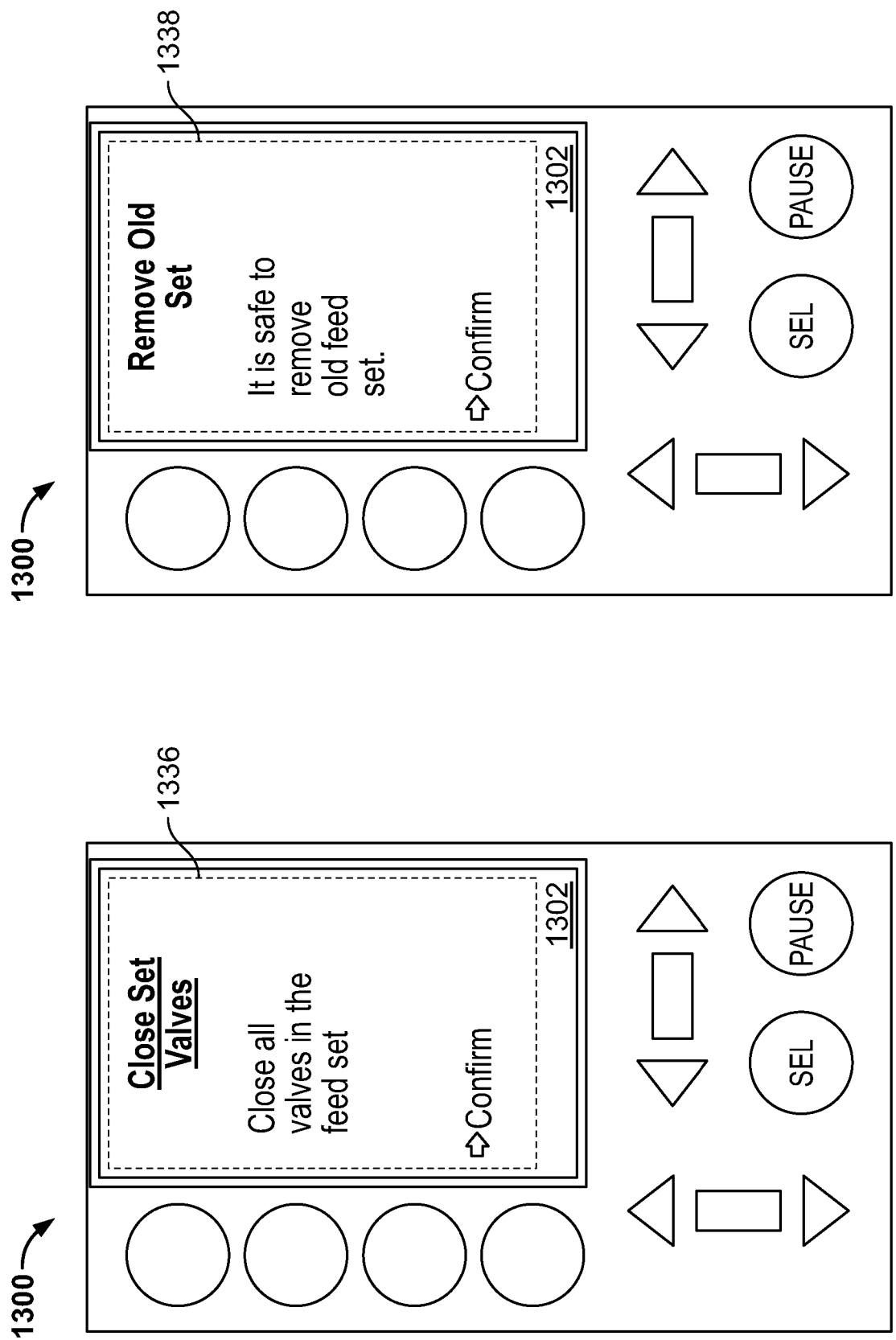
FIG. 13P illustrates a close feed-set valves dialog within the display in accordance with an embodiment of the present specification.
FIG. 13Q illustrates a remove old feed set prompt within the display in accordance with an embodiment of the present specification.

At 13132, referring to FIG. 13P, a close feed-set valves dialog 1336 is illustrated within display 1302 in accordance with an embodiment of the present specification. In embodiments, to install the feed set, it is necessary to have the pinch rotor valve open. Before an 'Install Feed Set' dialog is invoked, the mechanism is checked to see if the pinch valve is closed. If it is, the mechanism is checked to see if a feed set is installed (detected by the mechanism sensors). If a feed set is present, the display 1302 prompts the user to close the tube valves of the feed set. This is to insure no free flow occurs. When the user presses "Confirm", the mechanism will set the pinch rotor to open both tubes. Also, it will home the pump motor. If no feed set is present, the mechanism will set the pinch rotor to open both tubes. Also, it will home the pump motor and this prompt is not displayed. The mechanism is ready to install a feed set. Pressing "Confirm" will display a prompt to remove old Feed Set.

At 13134, referring to FIG. 13Q, a remove old feed set prompt 1338 is illustrated within display 1302 in accordance with an embodiment of the present specification. If the mechanism detects that a feed set is already installed, the user may be prompted to remove it by displaying this Remove Old Feed Set Prompt 1338. The user may ignore this prompt and confirm the present pump configuration as valid. Pressing "Confirm" may allow the user to dismiss this prompt and the Priming Menu may be displayed if a tube set is detected by the mechanism. If the user removes the feed set the pump will display the first install feed set screen.

Figure 13S:
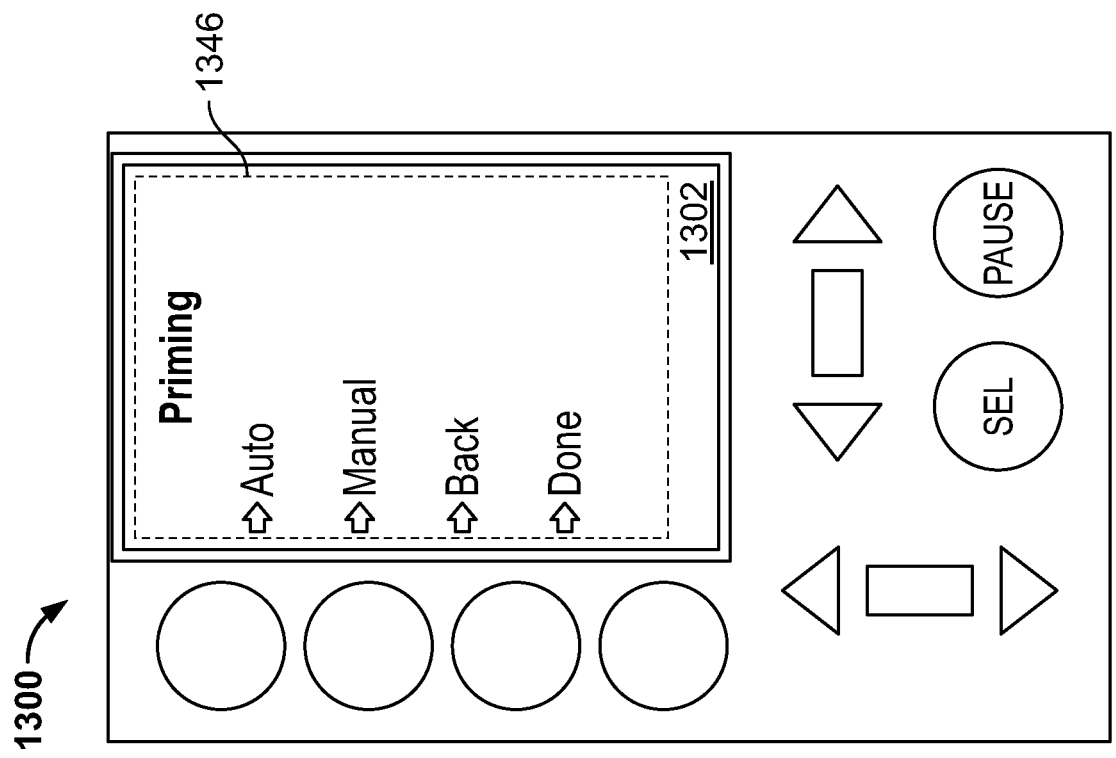
FIG. 13S illustrates a priming menu within the display in accordance with an embodiment of the present specification.
Figure 13R:
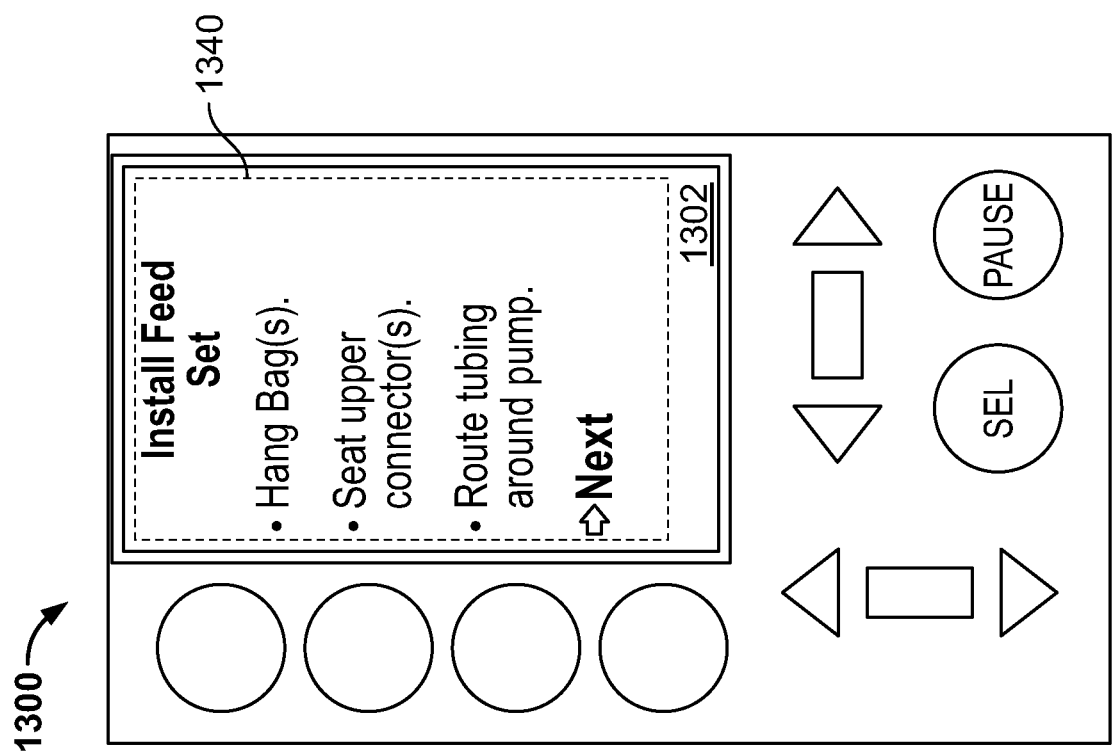
FIG. 13R illustrates an install feed set dialog within the display in accordance with an embodiment of the present specification.

At 13136, referring to FIG. 13R, an install feed set dialog 1340 is illustrated within display 1302 in accordance with an embodiment of the present specification. Dialog 1340 may be displayed if the mechanism is clear with no feed set installed. The mechanism will set the pinch rotor to open both tubes. It will also home the pump motor. This will allow the user to install the feed set. The Install Feed Set dialog 1340 may provide the user with an outline of steps to aid the user installing the feed set. The user may be reminded of the first steps and presses "Next". Pressing "Next" may display the next screen in the dialog.

An install feed set dialog may also be provided that is to remind of the steps to install the feed set is illustrated within display 1302 in accordance with an embodiment of the present specification. The Install Feed Set dialog may provide the user with an outline of steps to aid the user installing the feed set. The user is reminded of the last steps and presses "Done". Pressing "Done" may prompt the mechanism to detect the type of feed set that is installed. If the state of the system has the setup correct for the feed set install, the system will prompt the user to open the feed set valves. If the system state is not ready, the needed setup feed menu will be displayed to allow the user to revisit the feeding setup 1322.

Now referring to FIG. 13C, continuing from FIG. 13B, at 13138, an open feed set valves prompt may be provided within display 1302 in accordance with an embodiment of the present specification. If a feed and flush feed set (dual-use) is installed, the mechanism will open the flush pinch rotor valve. If the feed set is feed only (single use), then the mechanism will open the feed pinch rotor valve. The user is prompted by this screen to open the feed set valves. This is to prepare for the priming of the feed set.

At 13140, referring to FIG. 13S, a priming menu 1346 is illustrated within display 1302 in accordance with an embodiment of the present specification. In some embodiments, the user may initiate either an 'Auto Prime' feature, at 13142, or a 'Manual Prime' feature, at 13144. The 'Auto Prime' feature will prime a majority of the feed set including the patient tubing. It will stop short of the end to avoid spilling. The 'Manual Prime' feature may require user's interaction in the priming process. Pressing "Back" will display a previous menu. Pressing "Done" may display the 'Open Tube Valves' Prompt.

Figure 13T:
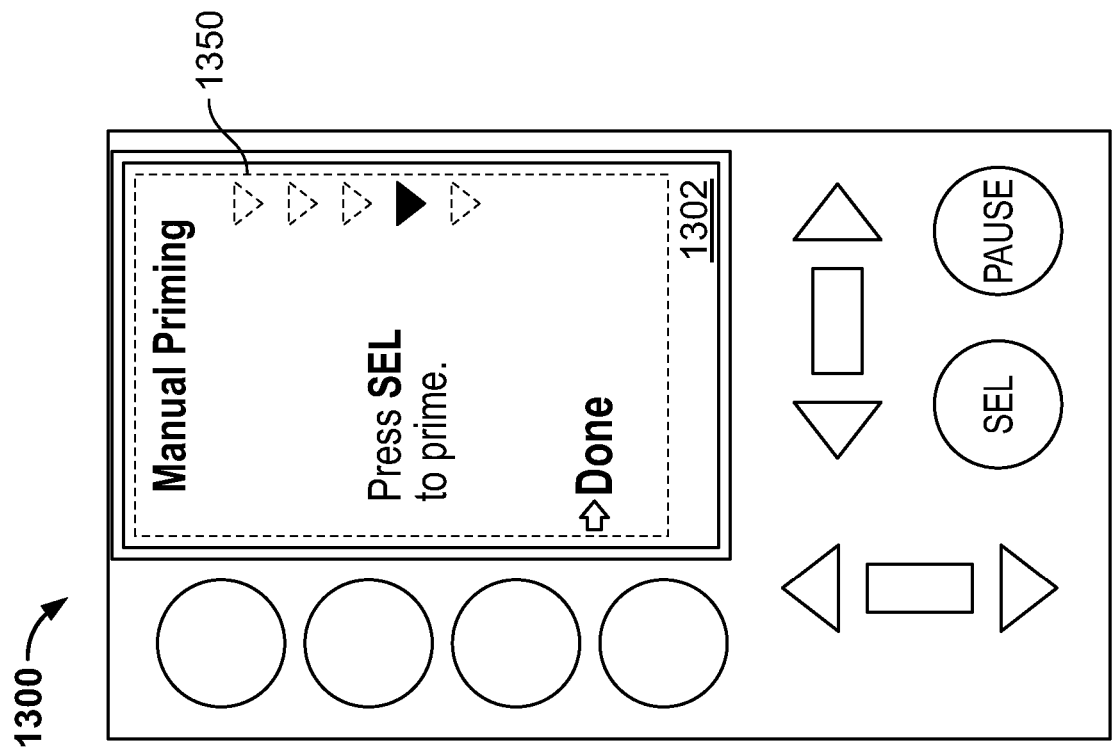
FIG. 13T illustrates an auto priming dialog within the display in accordance with an embodiment of the present specification.

At 13142, referring to FIG. 13T, an auto priming dialog 1348 is illustrated within display 1302 in accordance with an embodiment of the present specification. In some embodiments, auto priming dialog 1348 shows the user that auto priming is in progress. The user may stop auto priming by pressing "Pause". The user can know more about the process or continue from a Pause Auto Priming dialog. Pressing "Done" may end the dialog and go back to the Priming Menu 1346.

Figure 13U:
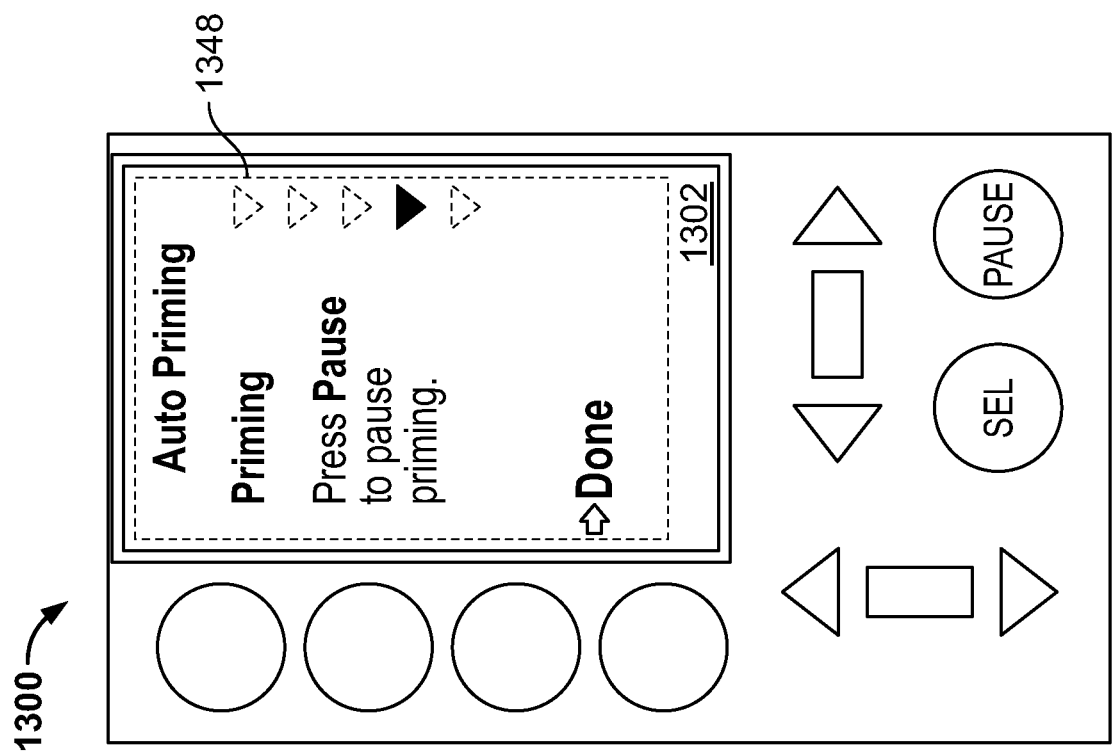
FIG. 13U illustrates a manual priming dialog within the display in accordance with an embodiment of the present specification.

At 13144, referring to FIG. 13U, a manual priming dialog 1350 is illustrated within display 1302 in accordance with an embodiment of the present specification. In some embodiments, the user may directly control the priming flow by pressing the "SEL" button. The user should prime to the end of the patient tube and may go past the end by a few drops. Pressing "Done" may end the dialog and go back to the Priming Menu 1346.

Figure 13W:
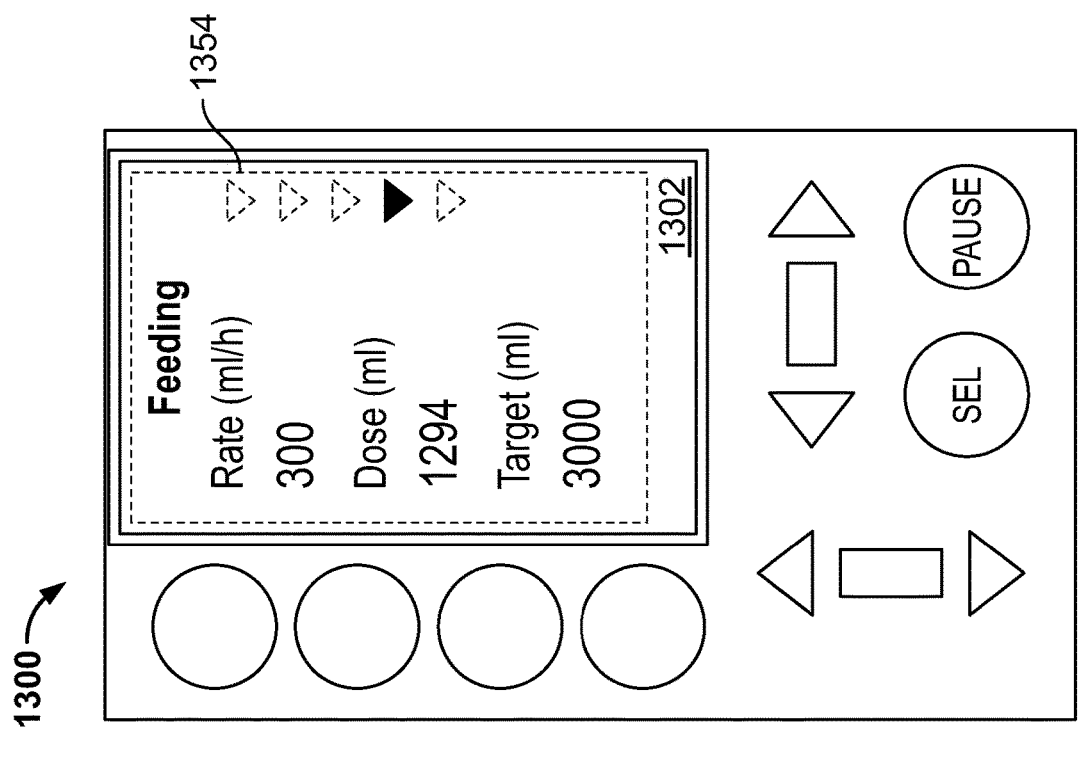
FIG. 13W illustrates a feeding screen within the display in accordance with an embodiment of the present specification.
Figure 13V:
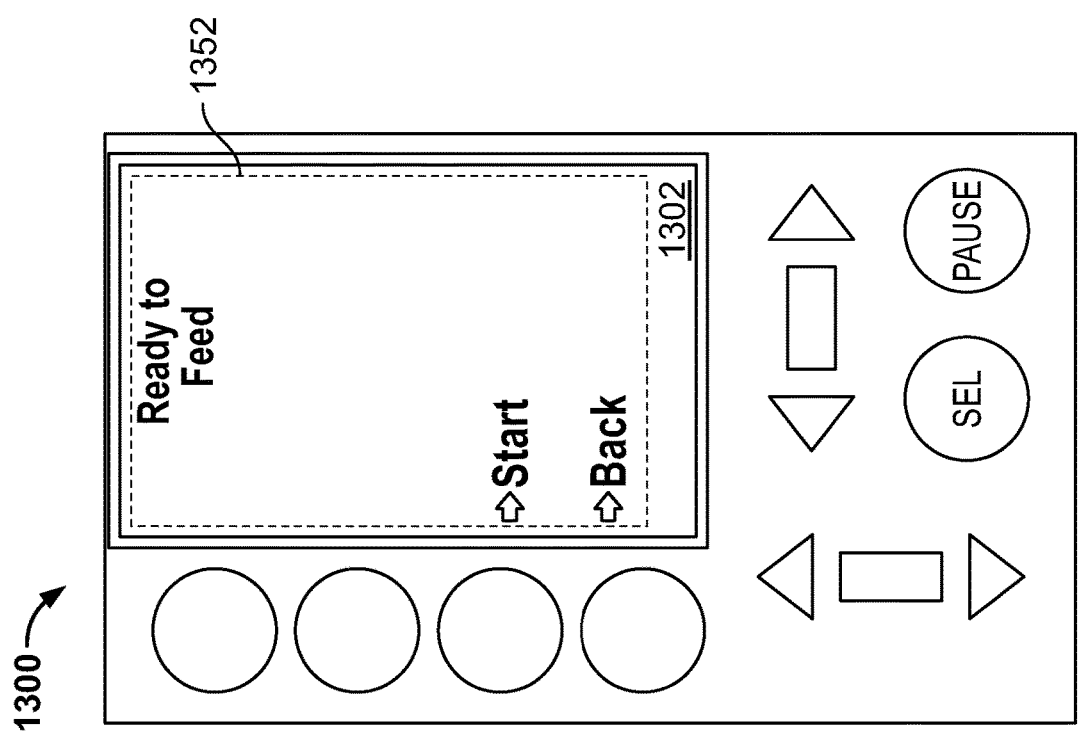
FIG. 13V illustrates a ready to feed dialog within the display in accordance with an embodiment of the present specification.

At 13146, referring to FIG. 13V, a ready to feed dialog 1352 is illustrated within display 1302 in accordance with an embodiment of the present specification. In embodiments, dialog 1352 may enable the user to start the patients feeding process.

At 13148, referring to FIG. 13W, a feeding screen 1354 is illustrated within display 1302 in accordance with an embodiment of the present specification. In some embodiments, screen 1354 provides the user with the feeding status.

Figure 13Y:
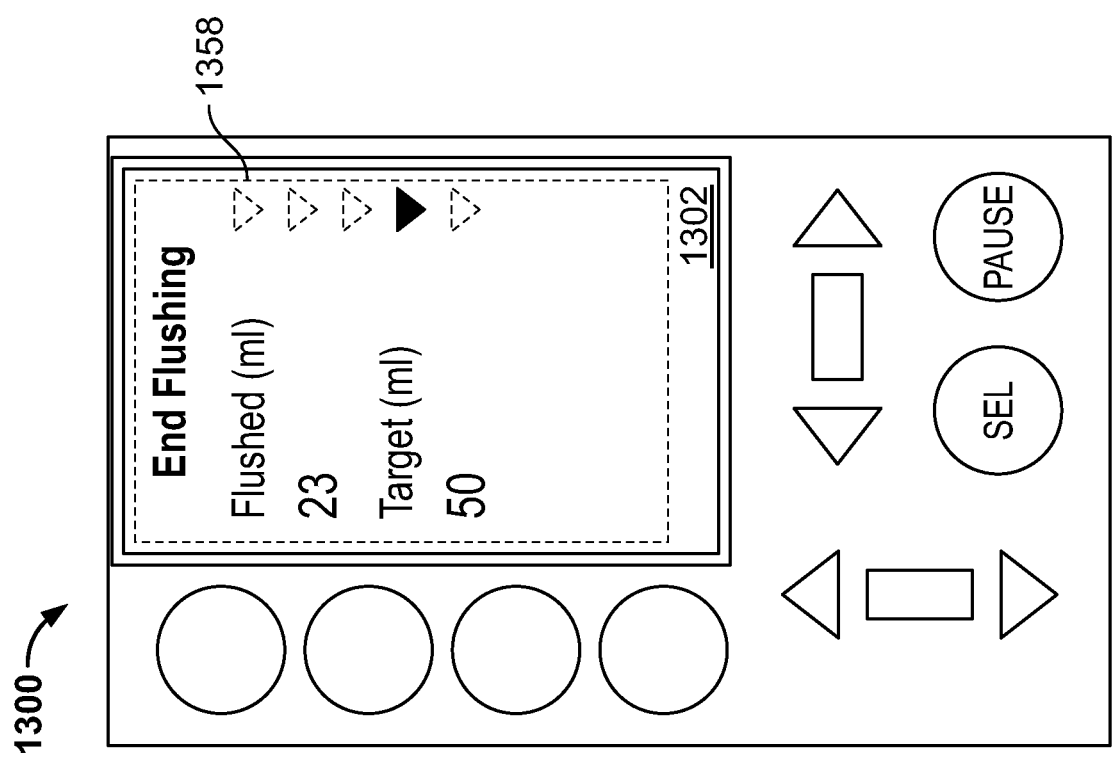
FIG. 13Y illustrates an end flush screen within the display in accordance with an embodiment of the present specification.
Figure 13X:
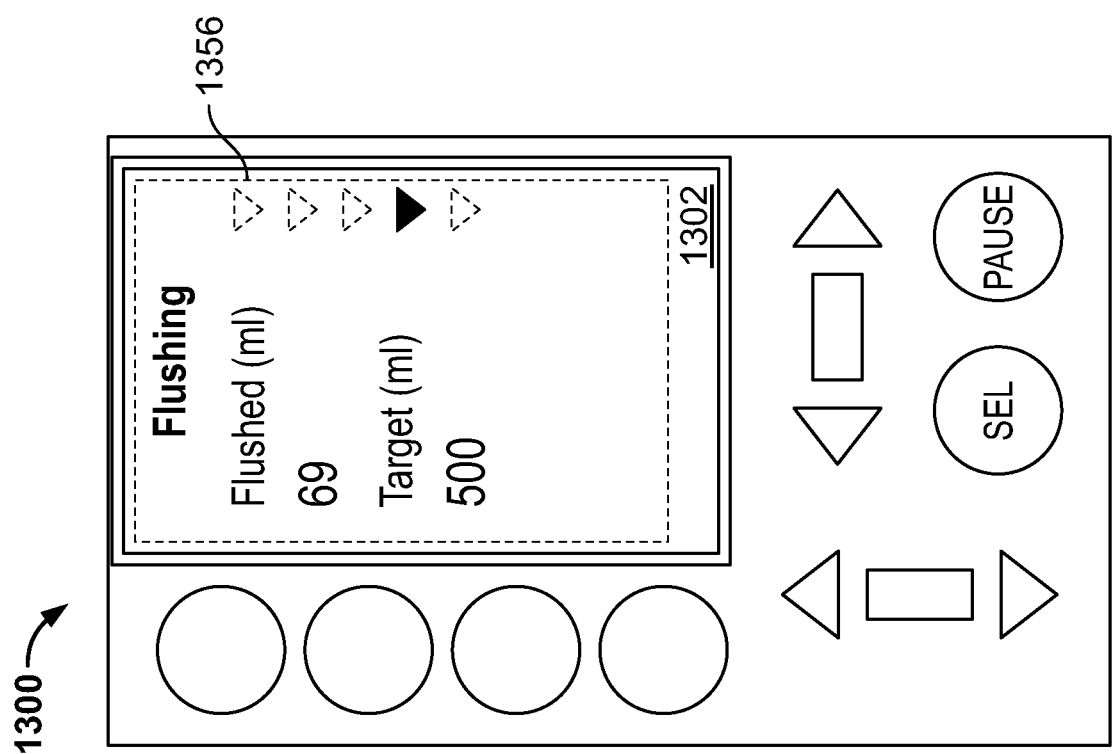
FIG. 13X illustrates a flushing screen within the display in accordance with an embodiment of the present specification.

At 13150, referring to FIG. 13X, a flushing screen 1356 is illustrated within display 1302 in accordance with an embodiment of the present specification. In some embodiments, screen 1356 provides the user with the flushing status.

At 13152, referring to FIG. 13Y, an end flush screen 1358 is illustrated within display 1302 in accordance with an embodiment of the present specification. In some embodiments, screen 1358 provides the user with the end flushing status.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. An enteral feeding system, comprising:
   a tubing set comprising two tube segments attached to a Y-connector, an outlet tube segment attached to a base of the Y-connector, a first rigid component attached to the inlets of the two tube segments, and a second rigid component attached to an outlet of the outlet tube segment; and
   an enteral feeding device comprising:
      a housing having a front surface;
      two vertical channels on the front surface, wherein each of the two vertical channels are configured to receive one of the two tube segments;
      a valve extending outwards from the front surface and positioned between the two vertical channels, wherein the valve is adapted to overlap at least partially with at least one of the two vertical channels;
      a pump extending outwards from the front surface, wherein the pump is configured to receive the outlet tube segment;
      a display positioned on the front surface, wherein the display is configured to present a user interface; and
      a first component receiver positioned at the top of the housing and configured to receive the first rigid component; and
      a second component receiver configured to receive the second rigid component.

2. The enteral feeding system of claim 1 wherein the housing further comprises a handle.

3. The enteral feeding system of claim 2 wherein the handle is configured on a side surface or top surface of the housing.

4. The enteral feeding system of claim 1 wherein the tubing set further comprises a third rigid component in physical communication with the Y connector.

5. The enteral feeding system of claim 4 wherein the enteral feeding device further comprises a third component receiver configured to receive the third rigid component.

6. The enteral feeding system of claim 5 wherein each of the first component receiver, the second component receiver, and the third component receiver are configured to detachably receive, in a friction fit, the first rigid component, second rigid component, and third rigid component respectively.

7. The enteral feeding system of claim 1 comprising a first sensor positioned within one of the two vertical channels and a second sensor positioned within one of the two vertical channels.

8. The enteral feeding system of claim 7 wherein the first sensor and the second sensor are optical sensors.

9. The enteral feeding system of claim 1, wherein the two vertical channels are parallel to each other.

10. The enteral feeding system of claim 1, wherein the two tube segments are parallel to each other.

11. The enteral feeding system of claim 1, wherein the valve is a pinch valve.

12. The enteral feeding system of claim 11, wherein the pinch valve is adapted rotate to overlap at least partially with at least one of the two vertical channels.

13. The enteral feeding system of claim 1, wherein the pump is a rotary pump.

14. The enteral feeding system of claim 1, wherein the two tube segments attached to the Y-connector comprise a first material having a first durometer value.

15. The enteral feeding system of claim 14, wherein the outlet tube segment comprises a second material having a second durometer value, wherein the first durometer value is less than the second durometer value.

16. The enteral feeding system of claim 1, further comprising at least one sensor in one of the two vertical channels.

17. The enteral feeding system of claim 16, wherein the at least one sensor is adapted to determine data indicative of whether the tubing set is properly mounted on the enteral feeding device.

18. The enteral feeding system of claim 16, wherein the at least one sensor is adapted to determine data indicative of whether the tubing set comprises occlusions.

19. The enteral feeding system of claim 16, wherein the at least one sensor is adapted to determine data indicative of a type of the tubing set.

20. The enteral feeding system of claim 16, wherein the at least one sensor is adapted to determine data indicative of a type of the tubing set to identify whether the tubing set is a single use disposable feeding tube for feeding purposes or a dual use disposable feeding tube for feeding and flushing purposes.

\* \* \* \* \*